United States Patent [19]
Massey et al.

[11] Patent Number: 5,866,434
[45] Date of Patent: Feb. 2, 1999

[54] GRAPHITIC NANOTUBES IN LUMINESCENCE ASSAYS

[75] Inventors: Richard J. Massey, Rockville; Mark T. Martin, Bethesda; Liwen Dong, Rockville; Ming Lu, Lanham; Alan Fischer, Cambridge; Fabian Jameison, Gaithersburg; Pam Liang, Rockville, all of Md.; Robert Hoch, Hensonville, N.Y.; Jonathan K. Leland, Silver Spring, Md.

[73] Assignee: Meso Scale Technology, Gaithersburg, Md.

[21] Appl. No.: 611,347

[22] Filed: Mar. 6, 1996

Related U.S. Application Data

[63] Continuation-in-part of Ser. No. 352,400, Dec. 8, 1994.
[51] Int. Cl.$^6$ ............... G01N 33/551; G01N 33/573; C12Q 1/32; C12Q 1/37
[52] U.S. Cl. ............... 436/526; 435/6; 435/7.4; 435/7.5; 435/7.92; 435/7.93; 435/7.94; 435/24; 435/26; 435/176; 435/182; 436/524; 436/535; 436/806; 530/391.1; 530/391.3; 530/391.5
[58] Field of Search ............... 435/7.4, 7.5, 24, 435/26, 6, 7.92, 7.93, 7.94, 176, 182; 436/524, 526, 535, 806; 530/391.1, 391.3, 391.5

[56] References Cited

U.S. PATENT DOCUMENTS

| | | | |
|---|---|---|---|
| 5,310,669 | 5/1994 | Richmond et al. | 435/174 |
| 5,547,748 | 8/1996 | Ruoff et al. | 428/323 |
| 5,554,751 | 9/1996 | Kampe | 544/338 |
| 5,582,955 | 12/1996 | Keana et al. | 427/581 |

*Primary Examiner*—Mary E. Ceperley
*Attorney, Agent, or Firm*—Whitman Breed Abbott & Morgan LLP

[57] ABSTRACT

Graphitic nanotubes, which include tubular fullerenes (commonly called "buckytubes") and fibrils, which are functionalized by chemical substitution, are used as solid supports in electrogenerated chemiluminescence assays. The graphitic nanotubes are chemically modified with functional group biomolecules prior to use in an assay. Association of electrochemiluminescent ruthenium complexes with the functional group biomolecule-modified nanotubes permits detection of molecules including nucleic acids, antigens, enzymes, and enzyme substrates by multiple formats.

19 Claims, 12 Drawing Sheets

GRAPHITIC NANOTUBES IN LUMINESCENCE ASSAYS

This application is a continuation-in-part of copending Fischer et al. application Ser. No. 08/352,400 entitled Functionalized Nanotubes, filed Dec. 8, 1994. The subject matter of this application is incorporated by reference.

FIELD OF THE INVENTION

This application relates generally to methods and apparatus for conducting binding assays, more particularly to those which measure the presence of an analyte of interest by measuring luminescence emitted by one or more labeled components of the assay system. More specifically, the invention relates to precise, reproducible, accurate homogeneous or heterogeneous specific binding assays of improved sensitivity in which the luminescent component is concentrated in the assay composition and collected on the detection system before being caused to electrochemiluminescence.

BACKGROUND OF THE INVENTION

Numerous methods and systems have been developed for the detection and quantitation of analytes of interest in biochemical and biological substances. Methods and systems which are capable of measuring trace amounts of microorganisms, pharmaceuticals, hormones, viruses, antibodies, nucleic acids and other proteins are of great value to researchers and clinicians.

A very substantial body of art has been developed based upon the well known binding reactions, e.g., antigen-antibody reactions, nucleic acid hybridization techniques, and protein-ligand systems. The high degree of specificity in many biochemical and biological binding systems has led to many assay methods and systems of value in research and diagnostics. Typically, the existence of an analyte of interest is indicated by the presence or absence of an observable "label" attached to one or more of the binding materials. Of particular interest are labels which can be made to luminesce through photochemical, chemical, and electrochemical means. "Photoluminescence" is the process whereby a material is induced to luminesce when it absorbs electromagnetic radiation. Fluorescence and phosphorescence are types of photoluminescence. "Chemiluminescent" processes entail the creation of luminescent species by chemical transfer of energy. "Electrochemiluminescence" entails creation of luminescent species electrochemically.

Chemiluminescent assay techniques where a sample containing an analyte of interest is mixed with a reactant labeled with a chemiluminescent label have been developed. The reactive mixture is incubated and some portion of the labeled reactant binds to the analyte. After incubation, the bound and unbound fractions of the mixture are separated and the concentration of the label in either or both fractions can be determined by chemiluminescent techniques. The level of chemiluminescence determined in one or both fractions indicates the amount of analyte of interest in the biological sample.

Electrochemiluminescent (ECL) assay techniques are an improvement on chemiluminescent techniques. They provide a sensitive and precise measurement of the presence and concentration of an analyte of interest. In such techniques, the incubated sample is exposed to a voltammetric working electrode in order to trigger luminescence. In the proper chemical environment, such electrochemiluminescence is triggered by a voltage impressed on the working electrode at a particular time and in a particular manner. The light produced by the label is measured and indicates the presence or quantity of the analyte. For a fuller description of such ECL techniques, reference is made to PCT published application US85/01253 (WO86/02734), PCT published application number US87/00987, and PCT published application U.S. 88/03947. The disclosures of the aforesaid applications are incorporated by reference.

It is desirable to carry out electrochemiluminescent assays without the need for a separation step during the assay procedure and to maximize the signal modulation at different concentrations of analyte so that precise and sensitive measurements can be made. Among prior art methods for nonseparation assays are those which employ microparticulate matter suspended in the assay sample to bind one or more of the binding components of the assay.

U.S. application Ser. No. 539,389 (PCT published application U.S. 89/04919) teaches sensitive, specific binding assay methods based on a luminescent phenomenon wherein inert microparticulate matter is specifically bound to one of the binding reactants of the assay system. The assays may be performed in a heterogeneous (one or more separation steps) assay format and may be used most advantageously in a homogeneous (nonseparation) assay format.

U.S. 89/04919 relates to a composition for an assay based upon a binding reaction for the measurement of luminescent phenomenon, which composition includes a plurality of suspended particles having a surface capable of binding to a component of the assay mixture. In another aspect, it is directed to a system for detecting or quantitating an analyte of interest in a sample, which system is capable of conducting the assay methods using the assay compositions of the inventions. The system includes means for inducing the label compound in the assay medium to luminesce, and means for measuring the luminescence to detect the presence of the analyte of interest in the sample.

It was found that the binding of that component of the assay system to which an electrochemiluminescent moiety has been linked, to suspended microparticulate matter, greatly modulates the intensity of the luminescent signal generated by the electrochemiluminescent moiety linked to that component, thereby providing a means of monitoring the specific binding reaction of the assay system. The suspended particles were found to have little or no effect on the intensity of the luminescent signal generated by the electrochemiluminescent moiety linked to the component of the system which remains unbound to the suspended microparticulate matter.

Thus, U.S. 89/04919 is directed to methods for the detection of an analyte of interest in a sample, which method includes the steps of (1) forming a composition comprising (a) a sample suspected of containing an analyte of interest, (b) an assay-performance-substance selected from the group consisting of (i) analyte of interest or analog of the analyte of interest, (ii) a binding partner of the analyte of interest or its said analog, and (iii) a reactive component capable of binding with (i) or (ii), wherein one of said substances is linked to a label compound having a chemical moiety capable of being induced to luminesce, and (c) a plurality of suspended particles capable of specifically binding with the analyte and/or a substance defined in (b)(i), (ii), or (iii); (2) incubating the composition to form a complex which includes a particle and said label compound; (3) inducing the label compound to luminesce; and (4) measuring the luminescence emitted by the composition to detect the presence of the analyte of interest in the sample. Those same methods may be used to quantify the amount of analyte in a sample by comparing the luminescence of the assay composition to the luminescence of a composition containing a known amount of analyte.

Analogs of the analyte of interest, which may be natural or synthetic, are compounds which have binding properties comparable to the analyte, but include compounds of higher or lower binding capability as well. Binding partners suitable for use in the present invention are well-known. Examples are antibodies, enzymes, nucleic acids, lectins, cofactors and receptors. The reactive components capable of binding with the analyte or its analog and/or with a binding partner thereof may be a second antibody or a protein such as Protein A or Protein G or may be avidin or biotin or another component known in the art to enter into binding reactions.

Advantageously, the luminescence arises from electrochemiluminescence (ECL) induced by exposing the label compound, whether bound or unbound to specific binding partners, to a voltammetric working electrode. The ECL reactive mixture is controllably triggered to emit light by a voltage impressed on the working electrode at a particular time and in a particular manner to generate light. Although the emission of visible light is an advantageous feature the composition or system may emit other types of electromagnetic radiation, such as infrared or ultraviolet light, X-rays, microwaves, etc. Use of the terms "electrochemiluminescence," "electrochemiluminescent" "electrochemiluminescence" "luminescence," "luminescent," and "luminesce" includes the emission of light and other forms of electromagnetic radiation.

The methods taught in U.S. 89/04919 permit the detection and quantitation of extremely small quantities of analytes in a variety of assays performed in research and clinical settings. The demands of researchers and clinicians makes it imperative, however, to lower the detection limits of assays performed by these methods to increase the sensitivities of those assays and to increase the speed at which they can be performed.

Various methods are known in the art for increasing the signal from labeled species by concentrating them before subjecting them to a measurement step. In U.S. Pat. No. 4,652,333, for example, particles labeled with fluorescent, phosphorescent or atomic fluorescent labels are concentrated by microfiltration before a measurement step is performed.

It is also known in the art to concentrate labeled immunochemical species prior to a measurement step, by, e.g., drawing magnetically responsive labeled particles to the surface of a measurement vessel. In U.S. Pat. Nos. 4,731,337, 4,777,145, and 4,115,535, for example, such particles are drawn to the vessel wall and then are irradiated to excite a fluorophoric emission of light.

In U.S. Pat. No. 4,945,045, particles are concentrated on a magnetic electrode. An electrochemical reaction takes place at the electrode facilitated by a labeled chemical mediator. The immunochemical binding reaction alters the efficiency of the mediator resulting in a modulated signal when binding takes place.

While not being bound by any particular mechanistic explanation of surface excitation, e.g., electrochemiluminescence, it is believed that the label on the solid-phase complex must be oxidized at the electrode. This requires that an electron move from the label to the electrode. It is believed that the electron makes this "jump" by a phenomenon known as tunneling in which the electron passes through space (a region where its potential energy is very high, e.g., the solution) without having to go "over" the potential energy barrier. It can tunnel through the energy barrier, and thus, move from one molecule to another or from one molecule to an electrode without additional energy input. However, this tunneling phenomenon can only operate for very short distances. The probability of the tunneling phenomenon falls off exponentially as the distance between the two species increases. The probability of the tunneling phenomenon occurring between two species is fairly high if the distance is less than 25 Angstroms (2.5 nm) but is fairly low if the distance is greater. The distance of 25 Å is a rule-of-thumb used by those skilled in the art but is not an absolute limitation.

Accordingly, only those ECL labels with 25 Å of the surface of the electrode can be expected to participate in the ECL process. The area of the particle which is within 25 Å of the surface of an electrode is typically extremely small.

Accordingly, one would not expect that ECL from a particle surface would be measurable to any significant degree. Moreover, the light which is produced by the ECL process must pass through the particle to get to the photomultiplier. Since the particles are essentially opaque (a concentrated suspension of them is black) one would not expect that, even if significant amounts of light could be produced by ECL, that the light could pass through the particle and be measured by the photomultiplier.

Since the 1970s graphitic nanotubes and fibrils have been identified as materials of interest for a variety of applications. Submicron graphitic fibrils are sometimes called vapor grown carbon fibers. Carbon fibrils are vermicular carbon deposits having diameters less than $1.0\mu$, preferably less than $0.5\mu$, and even more preferably less than $0.2\mu$. They exist in a variety of forms and have been prepared through the catalytic decomposition of various carbon-containing gases at metal surfaces. Such vermicular carbon deposits have been observed almost since the advent of electron microscopy. A good early survey and reference is found in Baker and Harris, *Chemistry and Physics of Carbon*, Walker and Thrower ed., Vol. 14, 1978, p. 83, hereby incorporated by reference. See also, Rodriguez, N., *J. Mater. Research*, Vol. 8, p. 3233 (1993), hereby incorporated by reference.

In 1976, Endo et al. (see Obelin, A. and Endo, M., *J. of Crystal Growth*, Vol. 32 (1976), pp. 335–349, hereby incorporated by reference) elucidated the basic mechanism by which such carbon fibrils grow. There were seen to originate from a metal catalyst particle, which, in the presence of a hydrocarbon containing gas, becomes supersaturated in carbon. A cylindrical ordered graphitic core is extruded which immediately, according to Endo et al., becomes coated with an outer layer of pyrolytically deposited graphite. These fibrils with a pyrolytic overcoat typically have diameters in excess of $0.1\mu$, more typically 0.2 to $0.5\mu$.

In 1983, Tennent, U.S. Pat. No. 4,663,230, hereby incorporated by reference, succeeded in growing cylindrical ordered graphite cores, uncontaminated with pyrolytic carbon. Thus, the Tennent invention provided access to smaller diameter fibrils, typically 35 to 700 Å (0.0035 to $0.070\mu$) and to an ordered, "as grown" graphitic surface. Fibrillar carbons of less perfect structure, but also without a pyrolytic carbon outer layer have also been grown.

Fibrils, buckytubes and nanofibers are distinguishable from continuous carbon fibers commercially available as reinforcement materials. In contrast to fibrils, which have, desirably large, but unavoidably finite aspect ratios, continuous carbon fibers have aspect ratios (L/D) of at least $10^4$ and often $10^6$ or more. The diameter of continuous fibers is also far larger than that of fibrils, being always >1.0$\mu$ and typically 5 to 7$\mu$ Continuous carbon fibers are made by the pyrolysis of organic precursor fibers, usually rayon, polyacrylonitrile (PAN) and pitch. Thus, they may include heteroatoms within their structure. The graphitic nature of "as made" continuous carbon fibers varies, but they may be subjected to a subsequent graphitization step. Differences in degree of graphitization, orientation and crystallinity of graphite planes, if they are present, the potential presence of heteroatoms and even the absolute difference in substrate diameter make experience with continuous fibers poor predictors of nanofiber chemistry.

Tennent, U.S. Pat. No. 4,663,230 describes carbon fibrils that are free of a continuous thermal carbon overcoat and have multiple graphitic outer layers that are substantially parallel to the fibril axis. As such they may be characterized as having their c-axes, the axes which are perpendicular to the tangents of the curved layers of graphite, substantially perpendicular to their cylindrical axes. They generally have diameters no greater than 0.1$\mu$ and length to diameter ratios of at least 5. Desirably they are substantially free of a continuous thermal carbon overcoat, i.e., pyrolytically deposited carbon resulting from thermal cracking of the gas feed used to prepare them.

Tennent, et al., U.S. Pat. No. 5,171,560, hereby incorporated by reference, describes carbon fibrils free of thermal overcoat and having graphitic layers substantially parallel to the fibril axes such that the projection of said layers on said fibril axes extends for a distance of at least two fibril diameters. Typically, such fibrils are substantially cylindrical, graphitic nanotubes of substantially constant diameter and comprise cylindrical graphitic sheets whose c-axes are substantially perpendicular to their cylindrical axis. They are substantially free of pyrolytically deposited carbon, have a diameter less than 0.1$\mu$ and a length to diameter ratio of greater than 5. These fibrils are of primary interest in the invention.

Further details regarding the formation of carbon fibril aggregates may be found in the disclosure of Snyder et al., U.S. patent application Ser. No. 149,573, filed Jan. 28, 1988, and PCT Application No. US89/00322, filed Jan. 28, 1989 ("Carbon Fibrils") WO 89/07163, and Moy et al., U.S. patent application Ser. No. 413,837 filed Sep. 28, 1989 and PCT Application No. US90/05498, filed Sep. 27, 1990 ("Fibril Aggregates and Method of Making Same") WO 91/05089, all of which are assigned to the same assignee as the invention here and are hereby incorporated by reference.

Moy et al., U.S. Ser. No. 07/887,307 filed May 22, 1992, hereby incorporated by reference, describes fibrils prepared as aggregates having various macroscopic morphologies (as determined by scanning electron microscopy) in which they are randomly entangled with each other to form entangled balls of fibrils resembling bird nests ("BN"); or as aggregates consisting of bundles of straight to slightly bent or kinked carbon fibrils having substantially the same relative orientation, and having the appearance of combed yarn ("CY") e.g., the longitudinal axis of each fibril (despite individual bends or kinks) extends in the same direction as that of the surrounding fibrils in the bundles; or, as, aggregates consisting of straight to slightly bent or kinked fibrils which are loosely entangled with each other to form an "open net" ("ON") structure. In open net structures the degree of fibril entanglement is greater than observed in the combed yarn aggregates (in which the individual fibrils have substantially the same relative orientation) but less than that of bird nests. CY and ON aggregates are more readily dispersed than BN making them useful in composite fabrication where uniform properties throughout the structure are desired.

When the projection of the graphitic layers on the fibril axis extends for a distance of less than two fibril diameters, the carbon planes of the graphitic nanofiber, in cross section, take on a herring bone appearance. These are termed fishbone fibrils. Geus, U.S. Pat. No. 4,855,091, hereby incorporated by reference, provides a procedure for preparation of fishbone fibrils substantially free of a pyrolytic overcoat. These fibrils are also useful in the practice of the invention.

Carbon nanotubes of a morphology similar to the catalytically grown fibrils described above have been grown in a high temperature carbon arc (Iijima, Nature 354 56 1991). It is now generally accepted (Weaver, Science 265 1994) that these arc-grown nanofibers have the same morphology as the earlier catalytically grown fibrils of Tennent. Arc grown carbon nanofibers are also useful in the invention.

OBJECTS OF THE INVENTION

It is therefore an object of this invention to provide luminescence assays using particles having a high surface area for immobilization of assay performance substances to achieve advantageously high light emission.

It is also an object of this invention to provide compositions and assays using graphitic nanotubes (fibrils) which can be labeled with compounds capable of being induced to luminesce.

It is further object to provide functionalized fibrils for use in such assays.

DESCRIPTION OF THE INVENTION

Definition of Terms

The term "ECL moiety," "metal-containing ECL moiety" "label," "label compound," and "label substance," are used interchangeably. It is within the scope of the invention for the species termed "ECL moiety," "metal-containing ECL moiety," "organo-metallic," "metal chelate," "transition metal chelate" "rare earth metal chelate," "label compound," "label substance" and "label" to be linked to molecules such as an analyte or an analog thereof, a binding partner of the analyte or an analog thereof, and further binding partners of such aforementioned binding partner, or a reactive component capable of binding with the analyte, an analog thereof or a binding partner as mentioned above. The above-mentioned species can also be linked to a combination of one or more binding partners and/or one or more reactive components. Additionally, the aforementioned species can also be linked to an analyte or its analog bound to a binding partner, a reactive component, or a combination of one or more binding partners and/or one or more reactive components. It is also within the scope of the invention for a plurality of the aforementioned species to be bound directly, or through other molecules as discussed above, to an analyte or its analog. For purposes of brevity, these ligands are referred to as an assay-performance-substance.

The terms detection and quantitation are referred to as "measurement", it being understood that quantitation may require preparation of reference compositions and calibrations.

The terms collection and concentration of complex may be used interchangeably to describe the concentration of complex within the assay composition and the collection of complex at, e.g., an electrode surface.

BRIEF DESCRIPTION OF THE INVENTION

Figure 1:
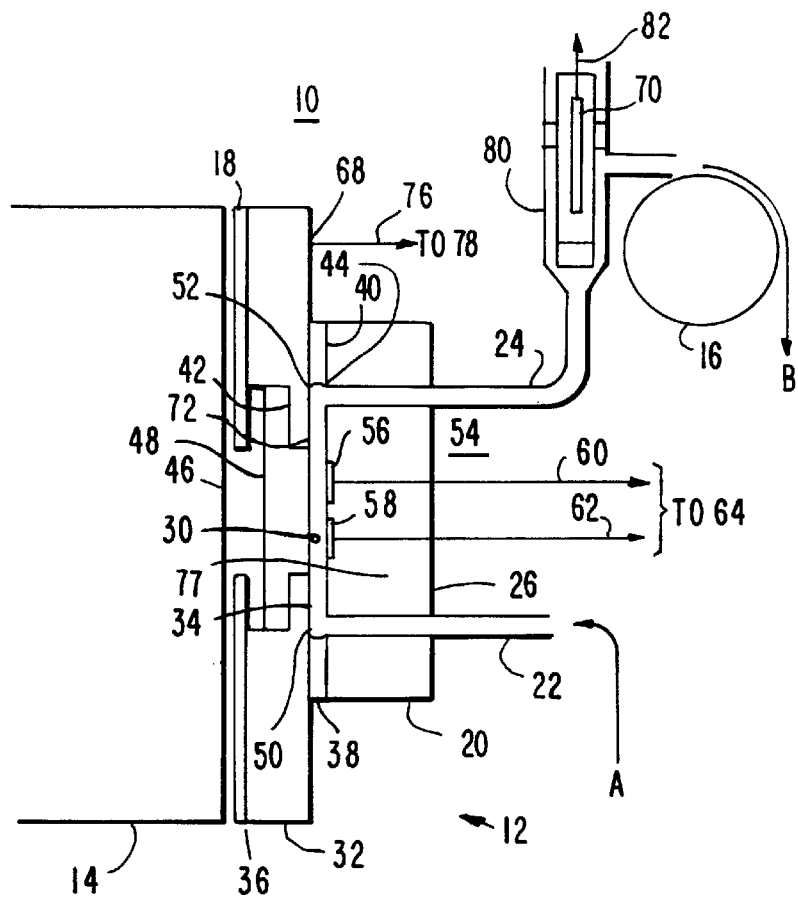
FIG. 1 is a schematic drawing of a cell for performing the microparticulate-based nonseparation and separation assays of the invention.

In its broadest embodiment, the invention is in a nanotube to which is attached a component linked to a label compound capable of being induced to luminesce. In particular, said nanotube is a graphitic nanotube and said luminescence is electrochemiluminescence. In one embodiment, said component is an enzyme biosensor.

The invention is also in a composition for the detection of an analyte of interest present in a sample, which composition comprises:

(i) a graphitic nanotube having a functional group and
(ii) an assay-performance-substance linked to said functional group, said assay-performance-substance being capable of binding, directly or indirectly, to the analyte.

In one embodiment, the assay-performance-substance being bound to said functional group is in turn bound to the analyte. The composition further comprises a second assay-performance-substance bound to the analyte, said second assay-performance-substance being linked to a label compound capable of being induced to luminesce.

The assay-performance-substance contains at least one substance selected from the group consisting of (i) added analyte of interest or added analogue of said analyte;

(ii) a binding partner of said analyte or a binding partner of said analogue; and
(iii) a reactive component capable of binding with (i) or (ii).

One of said substances (i), (ii) or (iii) is linked to a label compound having a chemical moiety capable of being induced to luminesce.

Broadly the particles are functionalized fibrils, i.e., fibrils whose surface has been reacted or contacted with one or more substances to provide active sites thereon for chemical substitution or physical adsorption of different chemical species. McCarthy et al., U.S. patent application Ser. No. 351,967 filed May 15, 1989, hereby incorporated by reference, describes processes for oxidizing the surface of carbon fibrils that include contacting the fibrils with an oxidizing agent that includes sulfuric acid ($H_2SO_4$) and potassium chlorate ($KClO_3$) under reaction conditions (e.g., time, temperature, and pressure) sufficient to oxidize the surface of the fibril. The fibrils oxidized according to the processes of McCarthy, et al. are non-uniformly oxidized, that is, the carbon atoms are substituted with a mixture of carboxyl, aldehyde, ketone, phenolic and other carbonyl groups.

Fibrils have also been oxidized non-uniformly by treatment with nitric acid. International Application PCT/US94/10168 discloses the formation of oxidized fibrils containing a mixture of functional groups. Hoogenvaad, M. S., et al. ("Metal Catalysts supported on a Novel Carbon Support", Presented at Sixth International Conference on Scientific Basis for the Preparation of Heterogeneous Catalysts, Brussels, Belgium, September 1994) also found it beneficial in the preparation of fibril-supported precious metals to first oxidize the fibril surface with nitric acid. Such pretreatment with acid is a standard step in the preparation of carbon-supported noble metal catalysts, where, given the usual sources of such carbon, it serves as much to clean the surface of undesirable materials as to functionalize it.

In published work, McCarthy and Bening (Polymer Preprints ACS Div. of Polymer Chem. 30 (1)420(1990)) prepared derivatives of oxidized fibrils in order to demonstrate that the surface comprised a variety of oxidized groups. The compounds they prepared, phenylhydrazones, haloaromaticesters, thallous salts, etc., were selected because of their analytical utility, being, for example, brightly colored, or exhibiting some other strong and easily identified and differentiated signal.

The particles are preferably functionalized fibrils which broadly have the formula

where n is an integer, L is a number less than 0.1n, m is a number less than 0.5n, each of R is the same and is selected from $SO_3H$, COOH, $NH_2$, OH, CHO, CN, COCl, halide, COSH, SH, COOR', SR', $SiR'_3$,

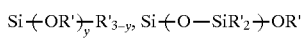

R", Li, $AlR'_2$, Hg—X, $TlZ_2$ and Mg—X, y is an integer equal to or less than 3, R' is alkyl, aryl, cycloalkyl or aralkyl, R" is fluoroalkyl, fluoroaryl, fluorocycloalkyl, fluoroaralkyl or cycloaryl, X is halide, and Z is carboxylate or trifluoroacetate.

The carbon atoms, $C_n$, are surface carbons of a substantially cylindrical, graphitic nanotube of substantially constant diameter. The nanotubes include those having a length to diameter ratio of greater than 5 and a diameter of less than $0.5\mu$, preferably less than $0.1\mu$. The nanotubes can also be substantially cylindrical, graphitic nanotubes which are substantially free of pyrolytically deposited carbon, more preferably those characterized by having a projection of the graphite layers on the fibril axis which extends for a distance of at least two fibril diameters and/or those having cylindrical graphitic sheets whose c-axes are substantially perpendicular to their cylindrical axis. These compositions are uniform in that each of R is the same.

The particles also include non-uniformly substituted nanotubes. These include compositions of the formula $$[C_nH_L \mathbin{+\!\!\!+} R_m]$$

where n, L, m, R and the nanotube itself are as defined above, provided that each of R does not contain oxygen, or, if each of R is an oxygen-containing group COOH is not present.

Functionalized nanotubes having the formula $$[C_nH_L \mathbin{+\!\!\!+} R_m]$$

where n, L, m, R and R' have the same meaning as above and the carbon atoms are surface carbon atoms of a fishbone fibril having a length to diameter ratio greater than 5, are also included as particles within the invention. These may be uniformly or non-uniformly substituted. Preferably, the nanotubes are free of thermal overcoat and have diameters less than $0.5\mu$.

Also included as particles in the invention are functionalized nanotubes having the formula $$[C_nH_L \mathbin{+\!\!\!+} [R'-R]_m]$$

where n, L, m, R' and R have the same meaning as above. The carbon atoms, $C_n$, are surface carbons of a substantially cylindrical, graphitic nanotube of substantially constant diameter. The nanotubes have a length to diameter ratio of greater than 5 and a diameter of less than $0.5\mu$, preferably less than $0.1\mu$. The nanotubes may be nanotubes which are substantially free of pyrolytically deposited carbon. More preferably, the nanotubes are those in which the projection of the graphite layers on the fibril axes extends for a distance of at least two fibril diameters and/or those having cylindrical graphitic sheets whose c-axes are substantially perpendicular to their cylindrical axis.

In both uniformly and non-uniformly substituted nanotubes, the surface atoms $C_n$ are reacted. Most carbon atoms in the surface layer of a graphitic fibril, as in graphite, are basal plane carbons. Basal plane carbons are relatively inert to chemical attack. At defect sites, where, for example, the graphitic plane fails to extend fully around the fibril, there are carbon atoms analogous to the edge carbon atoms of a graphite plane (See Urry, *Elementary Equilibrium Chemistry of Carbon*, Wiley, New York 1989.) for a discussion of edge and basal plane carbons).

At defect sites, edge or basal plane carbons of lower, interior layers of the nanotube may be exposed. The term surface carbon includes all the carbons, basal plane and edge, of the outermost layer of the nanotube, as well as carbons, both basal plane and/or edge, of lower layers that may be exposed at defect sites of the outermost layer. The edge carbons are reactive and must contain some heteroatom or group to satisfy carbon valency.

The substituted nanotubes described above may advantageously be further functionalized. Such compositions include compositions of the formula $$[C_nH_L \mathbin{+\!\!\!+} A_m]$$

where the carbons are surface carbons of a nanotube, n, L and m are as described above, A is selected from $$\overset{O}{\underset{\|}{C}}-OY, \ \overset{O}{\underset{\|}{C}}-NR'Y, \ \overset{O}{\underset{\|}{C}}-SY, \ \overset{O}{\underset{\|}{C}}-Y,$$

$-CR'_2-OY$, $N=Y$ or $C=Y$,

Y is an appropriate functional group of a protein, a peptide, an enzyme, an antibody, a nucleotide, an oligonucleotide, an antigen, or an enzyme substrate, enzyme inhibitor or the transition state analog of an enzyme substrate or is selected from $R'-OH$, $R'-NH_2$, $R'SH$, $R'CHO$, $R'CN$, $R'X$, $R'SiR'_3$, $R'Si(-OR')_y R'_{3-y}$, $R'Si(-O-SiR'_2-)OR'$, $R'-R''$, $R'-N-CO$, $(C_2H_4O-)_wH$, $(-C_3H_6O-)_wH$, $(-C_2H_4O)_w-R'$, $(C_3H_6O)_w-R'$ and $R'$, and w is an integer greater than one and less than 200.

The carbon atoms, $C_n$, are surface carbons of a substantially cylindrical, graphitic nanotube of substantially constant diameter. The nanotubes include those having a length to diameter ratio of greater than 5 and a diameter of less than $0.1\mu$, preferably less than $0.05\mu$. The nanotubes can also be substantially cylindrical, graphitic nanotubes which are substantially free of pyrolytically deposited carbon. More preferably they are characterized by having a projection of the graphite layers on the fibril axes which extends for a distance of at least two fibril diameters and/or they are comprised of cylindrical graphitic sheets whose c-axes are substantially perpendicular to their cylindrical axes. Preferably, the nanotubes are free of thermal overcoat and have diameters less than $0.5\mu$.

The functional nanotubes of structure $$[C_nH_L \mathbin{+\!\!\!+} [R'-R]_m]$$

may also be functionalized to produce compositions having the formula $$[C_nH_L \mathbin{+\!\!\!+} [R'-A]_m]$$

where n, L, m, R' and A are as defined above. The carbon atoms, $C_n$, are surface carbons of a substantially cylindrical, graphitic nanotube of substantially constant diameter. The nanotubes include those having a length to diameter ratio of greater than 5 and a diameter of less than $0.5\mu$, preferably less than 0.1μ. The nanotubes can also be substantially cylindrical, graphitic nanotubes which are substantially free of pyrolytically deposited carbon. More preferably they are characterized by having a projection of the graphite layers on the fibril axes which extends for a distance of at least two fibril diameters and/or by having cylindrical graphitic sheets whose c-axes are substantially perpendicular to their cylindrical axis. Preferably, the nanotubes are free of thermal overcoat and have diameters less than 0.5μ.

The particles of the invention also include nanotubes upon which certain cyclic compounds are adsorbed. These include compositions of matter of the formula

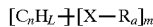

where n is an integer, L is a number less than 0.1n, m is less than 0.5n, a is zero or a number less than 10, X is a polynuclear aromatic, polyheteronuclear aromatic or metallopolyheteronuclear aromatic moiety and R is as recited above. The carbon atoms, $C_n$, are surface carbons of a substantially cylindrical, graphitic nanotube of substantially constant diameter. The nanotubes include those having a length to diameter ratio of greater than 5 and a diameter of less than 0.5μ, preferably less than 0.1μ. The nanotubes can also be substantially cylindrical, graphitic nanotubes which are substantially free of pyrolytically deposited carbon and more preferably those characterized by having a projection of the graphite layers on said fibril axes which extend for a distance of at least two fibril diameters and/or those having cylindrical graphitic sheets whose c-axes are substantially perpendicular to their cylindrical axes. Preferably, the nanotubes are free of thermal overcoat and have diameters less than 0.5μ.

Preferred cyclic compounds are planar macrocycles as described on p. 76 of Cotton and Wilkinson, *Advanced Organic Chemistry*. More preferred cyclic compounds for adsorption are porphyrins and phthalocyanines.

The adsorbed cyclic compounds may be functionalized. Such compositions include compounds of the formula

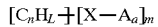

where m, n, L, a, X and A are as defined above and the carbons are surface carbons of a substantially cylindrical graphitic nanotube as described above.

The carbon fibrils functionalized as described above may be incorporated in a matrix. Preferably, the matrix is an organic polymer (e.g., a thermoset resin such as epoxy, bismaleimide, polyamide, or polyester resin; a thermoplastic resin; a reaction injection molded resin; or an elastomer such as natural rubber, styrene-butadiene rubber, or cis-1,4-polybutadiene); an inorganic polymer (e.g., a polymeric inorganic oxide such as glass), a metal (e.g., lead or copper), or a ceramic material (e.g., Portland cement).

Without being bound to a particular theory, the functionalized fibrils are better dispersed into polymer systems because the modified surface properties are more compatible with the polymer, or, because the modified functional groups (particularly hydroxyl or amine groups) are bonded directly to the polymer as terminal groups. In this way, polymer systems such as polycarbonates, polyurethanes, polyesters or polyamides/imides bond directly to the fibrils making the fibrils easier to disperse with improved adherence.

Functional groups are introduced onto the surface of carbon fibrils by contacting carbon fibrils with a strong oxidizing agent for a period of time sufficient to oxidize the surface of said fibrils and further contacting said fibrils with a reactant suitable for adding a functional group to the oxidized surface. Preferably, the oxidizing agent is comprised of a solution of an alkali metal chlorate in a strong acid. In other embodiments the alkali metal chlorate is sodium chlorate or potassium chlorate. In preferred embodiments the strong acid used is sulfuric acid. Periods of time sufficient for oxidation are from about 0.5 hours to about 24 hours.

A network of carbon fibrils are produced by contacting carbon fibrils with an oxidizing agent for a period of time sufficient to oxidize the surface of the carbon fibrils, contacting the surface-oxidized carbon fibrils with reactant suitable for adding a functional group to the surface of the carbon fibrils, and further contacting the surface-functionalized fibrils with a cross-linking agent effective for producing a network of carbon fibrils. A preferred cross-linking agent is a polyol, polyamine or polycarboxylic acid.

The functionalized fibrils may also be in the form of rigid networks of fibrils. A well-dispersed, three-dimensional network of acid-functionalized fibrils may, for example, be stabilized by cross-linking the acid groups (inter-fibril) with polyols or polyamines to form a rigid network.

The fibril particles also include three-dimensional networks formed by linking functionalized fibrils of the invention. These complexes include at least two functionalized fibrils linked by one or more linkers comprising a direct bond or chemical moiety. These networks comprise porous media of remarkably uniform equivalent pore size.

Although the interstices between these fibrils are irregular in both size and shape, they can be thought of as pores and characterized by the methods used to characterize porous media. The size of the interstices in such networks can be controlled by the concentration and level of dispersion of fibrils, and the concentration and chain lengths of the cross-linking agents.

The complex including the particles may be collected on, e.g., an electrode surface where it is excited and induced to electrochemiluminescence by impressing a voltage on the electrode. While the invention is preferably carried out by collecting the complex in a measurement zone, i.e., on a surface at which it can be caused to luminesce, the invention also embraces methods wherein the complex is collected in a measurement zone and thereafter means are brought to that zone or other steps taken to induce and measure luminescence.

The collection of the complex may be carried out by several different methods, including gravity settling, filtration, centrifugation and magnetic attraction of magnetically responsive particles which form part of the complex. The several embodiments are described in further detail below.

The invention is also in a method for performing a binding assay for an analyte of interest present in a sample comprising the steps of:
(a) forming a composition containing
  (i) said sample
  (ii) an assay-performance-substance which contains a component linked to a label compound capable of being induced to luminesce, and
  (iii) a plurality of functionalized graphitic nanotubes bound to an assay-performance-substance;
(b) incubating said composition to form a complex which includes said functionalized graphitic nanotube and said label compound;
(c) collecting said complex in a measurement zone;
(d) inducing the label compound in said complex to luminesce by surface selective excitation, and (e) measuring the emitted luminescence to measure the presence of the analyte of interest in the sample.

In particular, said complex is collected on the surface of means for inducing luminescence and measuring said luminescence.

The method is advantageously based upon measurement of electrochemiluminescence wherein said complex is collected at an electrode surface.

The invention is also in a method for performing a binding assay for an analyte of interest present in a sample based upon measurement of electrochemiluminescence at an electrode surface comprising the steps:

(a) forming a composition containing
  (i) said sample
  (ii) an assay-performance-substance which contains a component linked to a label compound capable of being induced to electrochemiluminescence, and
  (iii) a plurality of functionalized graphitic nanotubes bound to an assay-performance-substance;
(b) incubating said composition to form a complex which includes said functionalized graphitic nanotube and said label compound;
(c) collecting said complex;
(d) causing said collected complex to come in contact with an electrode surface and inducing the label compound in said complex to luminesce by impressing a voltage on said electrode; and
(e) measuring the emitted luminescence at the electrode surface to measure the presence of the analyte of interest in the sample.

The invention is further in a method for performing a binding assay for an analyte of interest present in a sample based upon measurement of electrochemiluminescence at an electrode surface comprising the steps:

(a) forming a composition containing
  (i) said sample
  (ii) an assay-performance-substance which contains a component linked to a label compound capable of being induced to electrochemiluminesce, and
  (iii) a plurality of magnetically responsive, suspended, functionalized, graphitic nanotubes bound to an assay-performance-substance;
(b) incubating said composition to form a complex which includes a graphitic nanotube and said label compound;
(c) collecting said complex by imposition of a magnetic field on said graphitic nanotubes;
(d) causing said collected complex to come in contact with an electrode surface and inducing the label compound in said complex to luminescence by imposing a voltage on said electrode; and
(e) measuring the emitted luminescence at the electrode surface to measure the presence of the analyte of interest in the sample.

The imposition of said magnetic field causes said complex to collect at the surface of said electrode.

In addition, the invention is in a composition of matter for use as a reagent in a microparticulate-based binding assay comprising functionalized graphitic nanotubes and at least one other component selected from the group consisting of:

(a) electrolyte;
(b) label compound containing an ECL moiety;
(c) analyte of interest or an analog of the analyte of interest;
(d) a binding partner of the analyte of interest or of its analog;
(e) a reactive component capable of reacting with (c) or (d);
(f) a reductant; and
(g) an electrochemiluminescent-reaction enhancer, provided; however, that no two components contained within any reagent composition are reactive with one another during storage so as to impair their function in the intended assay.

The reagent may contain magnetically responsive graphitic nanotubes.

The invention is also in an assay reagent for an assay based upon a binding reaction and the measurement of an electrochemiluminescent phenomenon comprising:

(a) an electrolyte;
(b) a plurality of magnetically responsive functionalized graphitic nanotubes having a surface bound to an assay-performance-substance; and
(c) a label substance having binding properties, said label substance including a chemical moiety having electrochemiluminescent properties.

The invention is further in a method for performing an assay for an analyte of interest present in a sample comprising the steps of:

(a) forming a composition containing
  (i) said sample, and
  (ii) a functionalized graphitic nanotube linked to an assay component linked to a label compound capable of being induced to luminesce, wherein said component is a substrate of the analyte of interest;
(b) incubating said composition under conditions to permit said analyte to cleave said component;
(c) separating said functionalized graphitic nanotube from said composition;
(d) inducing the label compound to luminesce; and
(e) measuring the emitted luminescence to measure the presence of the analyte of interest in the sample.

While batch assays can be performed, continuous or semi-continuous assays can be performed in flow cells. In a flow cell, the solid-phase remains in the measurement cell while the solution flows through and exits the cell. If the solid-phase (e.g., particles) are more dense than water, i.e., have a density greater than that of water, (more than 1.0 g/mL) the force of gravity upon the particles causes them to fall to the bottom of the cell. The cell can be constructed such that the particles settle to the bottom as the fluid flows through the cell or the cell can be constructed such that the majority of the sample is contained in the cell in a columnar compartment above the working electrode of an ECL system. Sufficient dwell time in the cell must be provided to permit the particles to settle on the surface of the electrode before inducing ECL.

In another embodiment of the invention, the assay composition containing suspended fibrils having a density greater than the balance of the assay composition may be subjected to centrifugation in order to remove the particles to a measurement zone where they are subsequently brought into contact with, e.g., an electrode to induce electrochemiluminescence or brought directly into contact with an electrode in the centrifugation step.

In this embodiment, the measurement cell is provided with means to rapidly rotate the sample and sample enclosure. Centrifugal force causes the fibrils in the sample to move outward from the axis of rotation of the sample enclosure and to collect on the outer surface of the sample enclosure. The outer surfaces of such sample enclosure may constitute the working electrode of an ECL measurement system.

In a third embodiment, the fibrils may be removed by filtration from the assay composition. In this embodiment the particles need not have a density greater than the balance of the assay composition. The fibrils are separated from the solution and concentrated by drawing the solution through a filter, e.g. pumping and collecting the particles on the surface of the filter. This surface of the filter is, for example, coated with a thin metal film which can serve as the working electrode in an ECL detection system.

In another embodiment, the suspended fibrils are magnetically responsive, e.g. they may be paramagnetic or ferromagnetic, and are collected in a measurement zone or, preferably, directly at the surface of an electrode, by imposition of a magnetic field on the particles. The measurement cell is equipped with a magnet. The magnetic field of the magnet applies a force on the particles as they reside in a batch cell or as they flow through a flow cell, causing them to separate from the bulk of the solution onto the surface of the cell which is in closest proximity to the magnet. If the magnet is placed in a proper orientation and in close proximity to the working electrode of an ECL detection system the particles will concentrate on the surface of the working electrode.

Several different heterogeneous and homogeneous formats for binding assays can be implemented using the methods described above to collect and concentrate the complex on the surface of an electrode. In a heterogeneous binding assay the complex is separated from the composition before measuring luminescence from the label. In homogeneous assays, no separation of the bound (to the solid phase) and unbound labeled reagents is made.

In a homogeneous assay, when the complex is concentrated on the surface of the working electrode, the measured signal from the label is much greater than it would be in the absence of a collection step. The signal from the uncomplexed labeled reagents, in contrast, is not changed. Hence, despite the presence of the uncomplexed labeled reagents in the measurement cell, the signal from the collected complex is stronger than in an assay without collection of complex. The detection limit for the binding assay is, much improved as a result of the collection procedure.

In a preferred embodiment of the invention, an in-situ separation step is included in the homogeneous binding assay procedure. After the assay composition, i.e., sample, assay performance substance and particles have been pumped into the measurement cell and the complex captured upon the working electrode, a second fluid is pumped through the cell which is free of label or labeled reagents, thereby performing an in-situ wash or separation of the complex from unbound components of the assay composition. This assay procedure is technically a heterogeneous binding assay. However, the ability to perform the separation inside the measurement cell is advantageous in that it does not require additional separation apparatus and the procedure is generally much faster than external separation methods.

Heterogeneous binding assays are conducted using the invention by mixing the components of the assay composition and allowing them to react for a predetermined length of time. The assay composition is then subjected to a separation step wherein the solution is separated from the particles. Electrochemiluminescence is then measured from either the complex or the solution. Measuring the ECL from the complex after a concentration step permits measurement of analyte with better accuracy and with a lower detection limit than is possible without concentration.

REPRESENTATIVE EXAMPLE

In one representative embodiment of the invention the functionalized fibril is further reacted with avidin (an assay-performance-substance) to prepare it for use in an ECL assay. The so-modified fibril is then reacted with a biotinylated oligonucleotide (an assay-performance-substance) to form a fibril-avidin-biotin-oligonucleotide complex for use in a DNA probe assay. This complex can be used as a probe for an oligonucleotide analyte of interest which is complementary to said probe in a sandwich assay in the presence of a second oligonucleotide complementary to said analyte of interest labeled with an ECL moiety.

DETAILED DESCRIPTION OF THE INVENTION

The invention, as well as other objects and features thereof, will be understood more clearly and fully from the following description of certain preferred embodiments.

The invention is broadly applicable to analytes of interest which are capable of entering into binding reactions. These reactions include, e.g., antigen-antibody, ligand receptor, DNA and RNA interactions, and other known reactions. The invention relates to different methods and assays for qualitatively and quantitatively detecting the presence of such analytes of interest in a multicomponent sample.

The Samples

The sample which may contain the analyte of interest, which may be in solid, emulsion, suspension, liquid, or gas form, may be derived from, for example, cells and cell-derived products, water, food, blood, serum, hair, sweat, urine, feces, tissue, saliva, oils, organic solvents or air. The sample may further comprise, for example, water, acetonitrile, dimethyl sulfoxide, dimethyl formamide, n-methyl-pyrrolidone or alcohols or mixtures thereof.

The Analytes

Typical analytes of interest are a whole cell or surface antigen, subcellular particle, virus, prion, viroid, antibody, antigen, hapten, fatty acid, nucleic acid, protein, lipoprotein, polysaccharide, lipopolysaccharide, glycoprotein, peptide, polypeptide, cellular metabolite, hormone, pharmacological agent, synthetic organic molecule, organometallic molecule, tranquilizer, barbiturate, alkaloid, steroid, vitamin, amino acid, sugar, lectin, recombinant or derived protein, biotin, avidin, streptavidin, or inorganic molecule present in the sample. Typically, the analyte of interest is present at a concentration of $10^{-3}$ molar or less, for example, as low as $10^{-12}$ molar or lower.

Assay-Performance-Substance

The assay-performance-substance which is combined with the sample containing the analyte of interest contains at least one substance selected from the group consisting of (i) added analyte of interest or its analog, as defined above, (ii) a binding partner of the analyte of interest or its said analog, and (iii) a reactive component, as defined above, capable of binding with (i) or (ii), wherein one of said substances is linked to a compound or moiety, e.g. an ECL moiety capable of being induced to luminesce. The labeled substance may be a whole cell or surface antigen, a subcellular particle, virus, prion, viroid, antibody, antigen, hapten, lipid, fatty acid, nucleic acid, polysaccharide, protein, lipoprotein, lipopolysaccharide, glycoprotein, peptide, polypeptide, cellular metabolite, hormone, pharmacological agent, tranquilizer, barbiturate, alkaloid, steroid, vitamin, amino acid, sugar, nonbiological polymer (preferably soluble), lectin, recombinant or derived protein, synthetic organic molecule, organometallic molecule, inorganic molecule, biotin, avidin or streptavidin. In one embodiment, the reagent is an electrochemiluminescent moiety conjugated to an antibody, antigen, nucleic acid, hapten, small nucleotide sequence, oligomer, ligand, enzyme, or biotin, avidin, streptavidin, Protein A, Protein G, or complexes thereof, or other secondary binding partner capable of binding to a primary binding partner through protein interactions.

Analogs of the analyte of interest, which can be natural or synthetic, are typically compounds which have binding properties comparable to the analyte, but can also be compounds of higher or lower binding capability. The reactive components capable of binding with the analyte or its analog, and/or with a binding partner thereof, and through which the ECL moiety can be linked to the analyte, is suitably a second antibody or a protein such as Protein A or Protein G, or avidin or biotin or another component known in the art to enter into binding reactions.

The Labels

Advantageously, the ECL moieties are metal chelates. The metal of that chelate is suitably any metal such that the metal chelate will luminesce under the electrochemical conditions which are imposed on the reaction system in question. The metal of such metal chelates is, for instance, a transition metal (such as a d-block transition metal) or a rare earth metal. The metal is preferably ruthenium, osmium, rhenium, iridium, rhodium, platinum, indium, palladium, molybdenum, technetium, copper, chromium or tungsten. Especially preferred are ruthenium and osmium.

The ligands which are linked to the metal in such chelates are usually heterocyclic or organic in nature, and play a role in determining whether or not the metal chelate is soluble in an aqueous environment or in an organic or other nonaqueous environment. The ligands can be polydentate, and can be substituted. Polydentate ligands include aromatic and aliphatic ligands. Suitable aromatic polydentate ligands include aromatic heterocyclic ligands. Preferred aromatic heterocyclic ligands are nitrogen-containing, such as, for example, bipyridyl, bipyrazyl, terpyridyl, and phenanthrolyl. Suitable substituents include for example, alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxysuccinimide. The chelate may have one or more monodentate ligands, a wide variety of which are known to the art. Suitable monodentate ligands include, for example, carbon monoxide, cyanides, isocyanides, halides, and aliphatic, aromatic and heterocyclic phosphines, amines, stilbenes, and arsines.

Examples of suitable chelates are bis [(4,4'-carbomethoxy)-2,2'-bipyridine] 2-[3-(4-methyl-2,2'-bipyridine-4-yl)propyl]-1,3-dioxolane ruthenium (II); bis (2,2'bipyridine) [4-(butan-1-al)-4'-methyl-2,2'-bipyridine] ruthenium (II); bis (2,2'-bipyridine) [4-(4'-methyl-2,2'-bipyridine-4'-yl)-butyric acid] ruthenium (II); tris (2,2'bipyridine) ruthenium (II); (2,2'-bipyridine) [bis-bis(1, 2-diphenylphosphino)ethylene] 2[3-(4-methyl-2,2'-bipyridine-4'-yl)propyl]-1,3-dioxolane osmium (II); bis (2,2'-bipyridine) [4-(4'-methyl-2,2'-bipyridine)-butylamine] ruthenium (II); bis (2,2'-bipyridine) [1-bromo-4(4'-methyl-2,2'-bipyridine-4-yl)butane] ruthenium (II); bis (2,2'-bipyridine)maleimidohexanoic acid, 4-methyl-2,2'-bipyridine-4'-butylamide ruthenium (II). Other ECL moieties are described in commonly assigned PCT published application US87/00987 and PCT published application 88/0394.

The function of the ECL moieties is to emit electromagnetic radiation as a result of introduction into the reaction system of electrochemical energy. In order to do this, they must be capable of being stimulated to an excited energy state and also capable of emitting electromagnetic radiation, such as a photon of light, upon descending from that excited state. While not wishing to be bound by theoretical analysis of the mechanism of the ECL moiety's participation in the electrochemiluminescent reaction, we believe that it is oxidized by the introduction of electrochemical energy into the reaction system and then, through interaction with a reductant present in the system, is converted to the excited state. This state is relatively unstable, and the metal chelate quickly descends to a more stable state. In so doing, the chelate gives off electromagnetic radiation, such as a photon of light, which is detectable.

The amount of metal chelate or other metal-containing ECL moiety incorporated in accordance with the invention will vary from system to system. Generally, the amount of such moiety utilized is that amount which is effective to result in the emission of a detectable, and if desired, quantitatable, emission of electromagnetic energy, from the aforementioned composition or system. The detection and/or quantitation of an analyte of interest is typically made from a comparison of the luminescence from a sample containing an analyte of interest and an ECL moiety to the luminescence emitted by a calibration standard developed with known amounts of the analyte of interest and ECL moiety. This assumes a homogeneous format. In the heterogeneous mode, a separation as discussed previously is carried out prior to ECL analysis.

As can be appreciated by one of ordinary skill in the art, the identity and amount of the metal-containing ECL moiety will vary from one system to another, depending upon prevailing conditions. The appropriate metal-containing ECL moiety, and sufficient amount thereof to obtain the desired result, can be determined empirically by those of ordinary skill in the art, once equipped with the teachings herein, without undue experimentation.

Graphitic Nanotubes

The nanotubes may be used as a solid support for analytical applications in various geometries including as dispersed, as aggregates, as mats or films, attached to larger supports including beads, or mixed with another material and used as a composite, for example in a porous column. Nanotubes primarily consist of chemically-modifiable graphitic carbon. They generally have diameters no greater than 0.1 $\mu$m and length to diameter ratios of at least 5. Typically, they have diameters of 0.01 $\mu$m and lengths of 1–10 $\mu$m.

Functionalized Nanotubes

Advantageously, the fibrils are functionalized fibrils, i.e. fibrils whose surfaces are uniformly or non-uniformly modified so as to have a functional chemical moiety associated therewith. The fibril surfaces may be functionalized by reaction with oxidizing or other chemical media. The fibril surfaces may be uniformly modified either by chemical reaction or by physical adsorption of species which themselves have a chemical reactivity. The fibril surfaces may be modified e.g. by oxidation and may be further modified by reaction with other functional groups. The fibril surfaces may be modified with a spectrum of functional groups so that the fibrils can be chemically reacted or physically bonded to chemical groups in a variety of substrates including binding components in electrochemiluminescence assays.

Complex structures of fibrils may be obtained by linking functional groups on the fibrils with one another by a range of linker chemistries.

Methods for chemical modification of fibril surfaces and methods for physically adsorbing species on the surfaces of fibrils are described so as to provide, in each case, a functional moiety associated with the surface of the fibril.

Functionalized Nanotubes Bound to Assay-Performance-Substances

The functionalized fibrils may be reacted with various biomolecules to prepare them for use in ECL assays. Various assay-performance-substances, e.g. antibodies, receptors, or other binding moieties, can be reacted with the functionalized fibrils to prepare them for use in ECL assays.

The Particles

Graphitic nanotubes may be covalently or noncovalently attached to larger solid phases, such as particles.

The particles advantageously comprise micro-particulate matter having a diameter of 0.05 $\mu$m to 200 $\mu$m, preferably 0.1 $\mu$m to 100 $\mu$m, most preferably 0.5 $\mu$m to 10 $\mu$m, and a surface component capable of binding to the analyte and/or one or more of the other substances defined in subparagraphs (b)(i), (b)(ii), or (b)(iii) above. For example, the microparticulate matter may be crosslinked starch, dextrans, cellulose, proteins, organic polymers, styrene copolymer such as styrene/butadiene copolymer, acrylonitrile/butadiene/styrene copolymer, vinylacetyl acrylate copolymer, or vinyl chloride/acrylate copolymer, inert inorganic particles, chromium dioxide, oxides of iron, silica, silica mixtures, and proteinaceous matter, or mixtures thereof. Desirably, the particles are suspended in the ECL system.

Assay Media

In order to operate a system in which an electrode introduces electrochemical energy, it is necessary to provide an electrolyte in which the electrode is immersed and which contains the ECL moiety. The electrolyte is a phase through which charge is carried by ions. Generally, the electrolyte is in the liquid phase, and is a solution of one or more salts or other species in water, an organic liquid or mixture of organic liquids, or a mixture of water and one or more organic liquids. However, other forms of electrolyte are also useful in certain embodiments of the invention. For example, the electrolyte may be a dispersion of one or more substances in a fluid—e.g., a liquid, a vapor, or a supercritical fluid—or may be a solution of one or more substances in a solid, a vapor or supercritical fluid.

The electrolyte is suitably a solution of a salt in water. The salt can be a sodium salt or a potassium salt preferably, but incorporation of other cations is also suitable in certain embodiments, as long as the cation does not interfere with the electrochemiluminescent interaction sequence. The salt's anion may be a phosphate, for example, but the use of other anions is also permissible in certain embodiments of the invention once—again, as long as the selected anion does not interfere with the electrochemiluminescent interaction sequence.

The composition may also be nonaqueous. While supercritical fluids can in certain instances be employed advantageously, it is more typical to utilize an electrolyte comprising an organic liquid in a nonaqueous composition. Like an aqueous electrolyte, the nonaqueous electrolyte is also a phase through which charge is carried by ions. Normally, this means that a salt is dissolved in the organic liquid medium. Examples of suitable organic liquids are acetonitrile, dimethylsulfoxide (DMSO), dimethylformamide (DMF), methanol, ethanol, and mixtures of two or more of the foregoing. Illustratively, tetraalkylammonium salts, such as tetrabutylammonium tetrafluoroborate, which are soluble in organic liquids can be used with them to form nonaqueous electrolytes.

The electrolyte is, in certain embodiments of the invention, a buffered system. Phosphate buffers are often advantageous. Examples are an aqueous solution of sodium phosphate/sodium chloride, and an aqueous solution of sodium phosphate/sodium fluoride.

Other Assay Components

As described PCT published application U.S. 89/04859 commonly assigned, entitled Electrochemiluminescent Reaction Utilizing Amine-Derived Reductant, the disclosure of which is incorporated by reference, it is desirable to include a reductant, typically an amine or amine moiety (of a larger molecule) which can be oxidized and spontaneously decomposed to convert it into a highly reducing species. It is believed that the amine or amine moiety is also oxidized by electrochemical energy introduced into the reaction system. The amine or amine moiety loses one electron, and then deprotonates, or rearranges itself, into a strong reducing agent. This agent interacts with the oxidized metal-containing ECL moiety and causes it to assume the excited state discussed above. In order to carry out its role, the amine or amine moiety preferably has a carbon-centered radical with an electron which can be donated from such carbon, and an alpha carbon which can then act as a proton donor during deprotonation in order to form the reductant. The amine-derived reductant provides the necessary stimulus for converting the metal-containing ECL moiety to its excited state, from which detectable electromagnetic radiation is emitted.

A wide range of amines and corresponding amine moieties can be utilized in practicing the present invention. Generally, the amine or amine moiety is chosen to suit the pH of the system which is to be electrochemiluminescently analyzed. Another relevant factor is that the amine or amine moiety should be compatible with the environment in which it must function during analysis, i.e., compatible with an aqueous or nonaqueous environment, as the case may be. Yet another consideration is that the amine or amine moiety selected should form an amine-derived reductant under prevailing conditions which is strong enough to reduce the oxidized metal-containing ECL moiety in the system.

Amines (and corresponding moieties derived therefrom) which are advantageously utilized in the present invention are aliphatic amines, such as primary, secondary and tertiary alkyl amines, the alkyl groups of each having from one to three carbon atoms, as well as substituted aliphatic amines. Tripropyl amine is an especially preferred amine as it leads to, comparatively speaking, a particularly high-intensity emission of electromagnetic radiation, which enhances the sensitivity and accuracy of detection and quantitation with embodiments in which it is used. Also suitable are diamines, such as hydrazine, and polymines, such as poly (ethyleneimine). Examples of other amines suitable for practicing the invention are triethanol amine, triethyl amine, 1,4-diazabicyclo-(2.2.2)-octane, 1-piperidine ethanol, 1,4-piperazine-bis-(ethane-sulfonic acid), tri-ispropyl amine and poly(ethyleneimine).

Typically, the metal-containing ECL moiety utilized in the present invention is the reaction-limiting constituent. Accordingly, it is also typical that the amine or amine moiety is provided in a stoichiometric excess with respect thereto. Illustratively, the amine or amine moiety is employed in a concentration of 50–150 mM. For utilization at a pH of approximately 7, a concentration of 100 mM is often advantageous. In certain embodiments, the upper limit on amine or amine moiety concentration is determined by the maximum solubility of the amine or moiety in the environment in which it is being used, for example in water. In general, the amount of amine or amine moiety employed is that which is sufficient to effect the transformation of the oxidized metal-containing ECL moiety into its excited state so that luminescence occurs. Those of ordinary skill in the art, equipped with the teachings herein, can determine empirically the amount of amine or amine moiety advantageously used for the particular system being analyzed, without undue experimentation.

As described in commonly assigned PCT published application US 89/04915, entitled Enhanced Electrochemiluminescent Reaction, the contents of which are incorporated by reference, the assays of the invention are desirably carried out in the presence of an enhancer, typically a compound of the formula

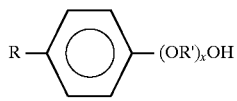

wherein R is hydrogen or $C_nH_{n2+1}$, R' is $C_nH_{2n}$, x is 0 to 70, and n is from 1 to 20. Specifically, n is from 1 to 4. Specific examples are a substance available in commerce under the name Triton X-100, of the formula

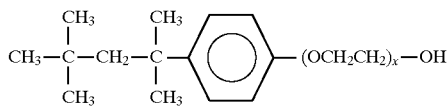

wherein x is 9–10, and a substance available in commerce under the name Triton N-401 (NPE-40), of the formula

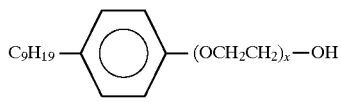

wherein x is 40. The enhancer is generally utilized in an amount sufficient so that in its presence the desired increase in emission of electromagnetic radiation occurs. Typically, the amount is 0.01% to 5.0%, more specifically 0.1% to 1.0%, v/v. The subject matter of this application is incorporated by reference.

The ECL moiety incorporated in accordance with the present invention is induced to emit electromagnetic radiation by stimulating it into an excited state. This is accomplished by exposing the system in which the ECL moiety is incorporated to electrochemical energy. The potential at which oxidation of the ECL moiety and the species forming a strong reductant occurs depends upon the exact chemical structures thereof, as well as factors such as the pH of the system and the nature of the electrode used to introduce electrochemical energy. It is well known to those of ordinary skill in the art how to determine the optimal potential and emission wavelength of an electrochemiluminescent system. Certain preferred methods of stimulating the ECL system are disclosed in commonly assigned PCT published application US 89/01814, the contents of which are incorporated herein by reference.

Apparatus for Measuring Electrochemiluminescence

Figure 2:
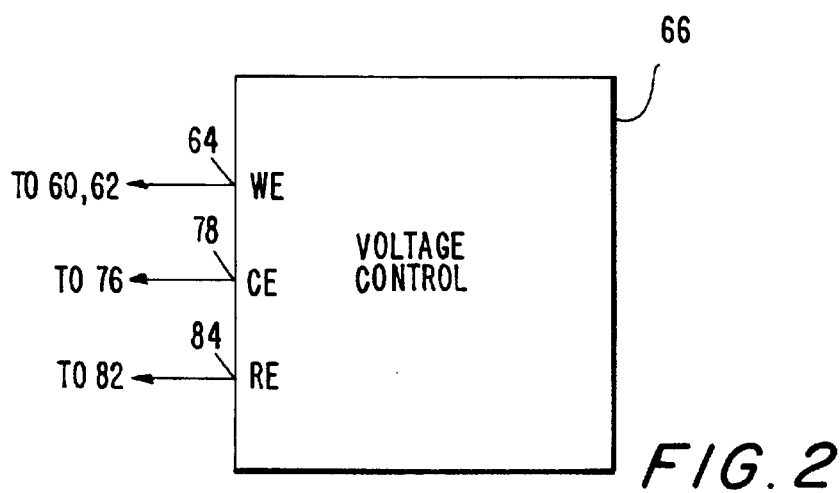
FIG. 2 is a simplified diagram of a voltage control apparatus for use with the cell of FIG. 1.

An apparatus for carrying out the assays of the invention is described in FIGS. 1 and 2. FIG. 1 discloses an advantageous ECL apparatus, but the methods of the present invention are not limited to application in apparatus 10, but rather may be employed in other types of ECL apparatus which include a working electrode or other triggering surface to provide electrochemical energy to trigger the ECL moiety into electrochemiluminescence. While the methods of the invention can be carried out in a static or flow-through mode, apparatus 10 includes a flow-through cell, which provides distinct advantages for many types of samples including binding-assay samples. Further details of apparatus for carrying out the ECL assays of the invention are disclosed in commonly assigned published PCT applications US 89/04854 and U.S. 90/01370.

Apparatus 10 includes an electrochemical cell 12, a light detection/measurement device 14, which may advantageously be a photomultiplier tube (PMT), photodiode, charge coupled device, photographic film or emulsion or the like, and a pump 16, which is advantageously a peristaltic pump, to provide for fluid transport to, through and from cell 12. Alternatively, a positive displacement pump may be used. A shutter mechanism 18 is provided between cell 12 and PMT 14 and is controllably operated to open only so far as to expose PMT 14 to cell 12 during ECL measurement periods. The shutter mechanism may be closed, for example, during maintenance. Also included in apparatus 10 but not illustrated in FIG. 1 is a lightproof housing intended to mount the various components therein and to shield PMT 14 from any external light during the ECL measurements.

Cell 12 itself includes a first mounting block 20 through which passes an inlet tube 22 and an outlet tube 24, which may be advantageously constructed of stainless steel. Mounting block 20 has a first, outer surface 26 and a second, inner surface 28 defining one side of a sample-holding volume 30 of cell 12 in which cell 12 holds the cleaning and/or conditioning and/or measurement solutions during corresponding operations of apparatus 10. Inlet and outlet tubes 22, 24 pass through mounting block 20 from outer surface 26 to inner surface 28 and open into sample-holding volume 30. A second mounting block 32, advantageously constructed of stainless steel also has a first, outer surface 34 and a second, inner surface 36. Second mounting block 32 is separated from first mounting block 20 by an annular spacer 38, advantageously constructed of Teflon or other non-contaminable material. Thus, outer surface 34 of mounting block 30 defines part of the second side of the sample-holding volume 30. Spacer 38 has an outer portion 40 and a central aperture 42 whose inner edge 44 defines the side wall of sample-holding volume 30. Outer portion 40 seals the inner surface 28 of first mounting block 20 to outer surface 34 of second mounting block 32 to prevent any solution from passing out from sample-holding volume 30 between the two surfaces 28, 34. Mounting block 32 further has a central aperture 46 in which a window 48 is seal-fitted to define the rest of the second side of sample-holding volume 30 as a continuation of outer surface 34. Window 48 is formed of a material which is substantially transparent at the wavelength of electrochemiluminescent light emitted by the ECL moiety. Window 48 is therefore advantageously formed of glass, plastic, quartz or the like.

Inlet tube 22 intersects sample-holding volume 30 at a first end 50 thereof adjacent to spacer 38 and outlet tube 24 intersects sample-holding volume 30 at a second end 52 thereof, adjacent spacer 38. The combination of inlet tube 22, sample-holding volume 30 and outlet tube 24 thereby provides a continuous flow path for the narrow, substantially laminar flow of a solution to, through and from cell 12.

Mounted on inner surface 28 of first mounting block 20 is a working electrode system 54 which, in the illustrated embodiment, includes first and second working electrodes 56 and 58. In other embodiments, a single working electrode may advantageously be provided, or only electrode 56 may be a working electrode. Working electrodes 56, 58 are where the electrochemical and ECL reactions of interest can take place. Working electrodes 56, 58 are solid voltammetric electrodes and may therefore be advantageously constructed of platinum, gold, carbons or other materials which are effective for this purpose. Wire connectors 60, 62 connected to working electrodes 56, 58, respectively, pass out through first mounting block 20.

Connectors 60, 62 are both connected to a first, "working electrode" terminal 64 of a voltage control 66, illustrated in FIG. 2. Voltage control 66 advantageously operates in the manner of a potentiostat to supply voltage signals to working electrodes 56, 58 and optionally to measure current flowing therefrom during an ECL measurement. Alternatively, connectors 60, 62 may be connected to separate terminals of voltage control 66 for individual operation.

The potentiostat operation of voltage control 66 is further effected through a counter electrode 68 and, optionally but advantageously, a reference electrode 70. In the illustrated embodiment, mounting block 32 is made of stainless steel and counter electrode 68 consists in exposed surfaces 72, 74 of mounting block 32. Counter electrode 72, 74 and working electrodes 56, 58 provide the interface to impress the potential on the solution within sample-holding volume 30 which energizes the chemical reactions and triggers electrochemiluminescence in the sample and/or provides energy for cleaning and conditioning the surfaces of cell 12. Counter electrode 72, 74 is connected by a wire connector 76 to a second, "counter electrode" terminal 78 of voltage control 66.

Reference electrode 70 provides a reference voltage to which the voltage applied by the working electrodes 56, 58 is referred, for example, +1.2 volts versus the reference. Reference electrode 70 is advantageously located in outlet tube 24 at a position 80 spaced from cell 12 and is connected through a wire connector 82 to a third "reference electrode" terminal 84 of voltage control 66. In the three electrode mode, current does not flow through reference electrode 70. Reference electrode 70 may be used in a three electrode mode of operation to provide a poised, known and stable voltage and is therefore advantageously constructed of silver/silver chloride (Ag/AgCl) or is a saturated calomel electrode (SCE). Voltage control 66 may be operable in a two electrode mode of operation using only working electrode 56 and electrode 58 as a counter/reference electrode. In this two electrode mode of operation, counter/reference electrode 58 is electrically connected to voltage control terminals 78 and 84 on voltage control 66. In this case, voltage control 66 operates essentially as a battery. Voltage control 66 supplies voltage signals to working and counter electrodes 56 and 58 and optionally measures the current flowing through the respective electrodes. Reference electrode 70 may alternatively be a so-called "quasi-reference" electrode constructed of platinum, gold, stainless steel or other material, which provides a less stable voltage, yet one that is measurable with respect to the solution in contact. In both the two and three electrode mode, the reference electrode 70 or 58 serves the purpose of providing a reference against which the voltage applied to working electrodes 56 is measured. The poised voltage reference is currently considered to be more advantageous. Voltage control 66 in its potentiostat operation controls the various electrodes by providing a known voltage at working electrodes 56, 58 with respect to reference electrode 70 while measuring the current flow between working electrodes 56, 58 and counter electrode 72, 74. Potentiostats for this purpose are well known, and the internal structure of voltage control 66 may therefore correspond to any of the conventional, commercially available potentiostats which produce the above-recited functions and so do not form a part of the present invention per se. Indeed, apparatus 10 may alternatively be constructed without an internal voltage control 66, and may be adapted to be connected to an external potentiostat which is separately controlled for providing the required voltage signals to electrodes 56, 58, 72, 74 and 70. These voltage signals, applied in a specific manner as described below, provide repeatable initial conditions for the surfaces of working electrodes 56, 58 and advantageously for the surfaces of cell 12 as a whole, a feature which contributes significantly to improved precision in ECL measurements.

Pump 16 is advantageously positioned at outlet tube 24 to "pull" solution from a sample volume in the direction of arrow A into inlet tube 22. The solution will flow through inlet tube 22, sample-holding volume 30 and outlet tube 24 past reference electrode 70 and out in the direction of arrow B. Alternatively, pump 16 may be positioned at inlet tube 22 to "push" the solution through apparatus 10. Advantageously, this same flow path through inlet tube 22, sample-holding volume 30 and outlet tube 24 is used for all solutions and fluids which pass through cell 12, whereby each fluid performs a hydrodynamic cleaning action in forcing the previous fluid out of cell 12. Pump 16 may be controlled to suspend its operation to hold a particular solution in cell 12 for any period of time.

The flow-through construction of apparatus 10 permits working electrodes to be impressed with a variable voltage or to be continuously held at a preoperative potential while being continuously exposed to one or more solutions without exposing working electrodes 56, 58 (or counter and reference electrodes 72, 74, 70 ) to air. Exposure to air, which opens the circuit to the reference electrode 70, permits unknown, random voltage fluctuations which destroy the reproducibility of surface conditions on working electrodes 56, 58. The flow-through construction permits the rapid alternation between initializing steps, in which electrode system 54 is cleaned and conditioned, and measurement steps, in which one or more measurement waveforms or sweeps trigger ECL.

The invention is also directed to reagent compositions. Broadly, the reagent compositions may be any one of the components of the assay systems of the invention, i.e., (a) electrolyte, (b) label compound containing an ECL moiety, (c) functionalized fibrils to which an assay-performance-substance is bound, optionally bound to particles, including magnetically responsive particles, (d) analyte of interest or an analog of the analyte of interest, (e) a binding partner of the analyte of interest or of its analog, (f) a reactive component capable of reacting with (d) or (e), (g) a reductant, or (h) an electrochemiluminescence-reaction enhancer. The reagents may be combined with one another for convenience of use, i.e., two component, three component, and higher multiple component mixtures may be prepared, provided that the components are not reactive with one another during storage so as to impair their function in the intended assay. Desirably, the reagents are two-component or multicomponent mixtures which contain particles as well as one or more other components.

The invention is also directed to kits. The kits may include vessels containing one or more of the components (a) to (h) recited above or the kits may contain vessels containing one or more reagent compositions as described above comprising mixtures of those components, all for use in the assay methods and systems of the invention.

METHODS OF FUNCTIONALIZING FIBRILS

The functionalized fibrils of the invention can be directly prepared by sulfonation, electrophilic addition to deoxygenated fibril surfaces or metallation. When arc grown nanofibers are used, they may require extensive purification prior to functionalization. Ebbesen et al. (Nature 367 519 (1994)) give a procedure for such purification.

Preferably, the carbon fibrils are processed prior to contacting them with the functionalizing agent. Such processing may include dispersing the fibrils in a solvent. In some instances the carbon fibrils may then be filtered and dried prior to further contact.

1. SULFONATION

Background techniques are described in March, J. P., *Advanced Organic Chemistry*, 3rd Ed. Wiley, New York 1985; House, H., *Modern Synthetic Reactions*, 2nd Ed., Benjamin/Cummings, Menlo Park, Calif. 1972.

Activated C—H (including aromatic C—H) bonds can be sulfonated using fuming sulfuric acid (oleum), which is a solution of conc. sulfuric acid containing up to 20% $SO_3$. The conventional method is via liquid phase at T~80° C. using oleum; however, activated C—H bonds can also be sulfonated using $SO_3$ in inert, aprotic solvents, or $SO_3$ in the vapor phase. The reaction is: p1 —C—H+$SO_3$→—C—$SO_3$H Over-reaction results in formation of sulfones, according to the reaction:

2—C—H+$SO_3$→—C—$SO_2$—C—+$H_2O$

Preparation A

Activation of C—H Bonds Using Sulfuric Acid

Reactions were carried out in the gas phase and in solution without any significant difference in results. The vapor phase reaction was carried out in a horizontal quartz tube reactor heated by a Lindberg furnace. A multi-neck flask containing 20% $SO_3$ in conc. $H_2SO_4$ fitted with gas inlet/outlet tubes was used as the $SO_3$ source.

A weighed sample of fibrils (BN or CC) in a porcelain boat was placed in the 1" tube fitted with a gas inlet; the outlet was connected to a conc. $H_2SO_4$ bubbler trap. Argon was flushed through the reactor for 20 min to remove all air, and the sample was heated to 300° C. for 1 hour to remove residual moisture. After drying, the temperature was adjusted to reaction temperature under argon.

When the desired temperature was stabilized, the $SO_3$ source was connected to the reactor tube and an argon stream was used to carry $SO_3$ vapors into the quartz tube reactor. Reaction was carried out for the desired time at the desired temperature, after which the reactor was cooled under flowing argon. The fibrils were then dried at 90° C. at 5" Hg vacuum to obtain the dry weight gain. Sulfonic acid (—$SO_3$H) content was determined by reaction with 0.100N NaOH and back-titration with 0.100N HCl using pH 6.0 as the end point.

The liquid phase reaction was carried out in conc. sulfuric acid containing 20% $SO_3$ in a multi-neck 100 cc flask fitted with a thermometer/temperature controller and a magnetic stirrer. A fibril slurry in conc. $H_2SO_4$ (50) was placed in the flask. The oleum solution (20 cc) was preheated to ~60° C. before addition to the reactor. After reaction, the acid slurry was poured onto cracked ice, and diluted immediately with 1 l DI water. The solids were filtered and washed exhaustively with DI water until there was no change in pH of the wash effluent. Fibrils were dried at 100° C. at 5" Hg vacuum. Due to transfer losses on filtration, accurate weight gains could not be obtained. Results are listed in Table I.

TABLE I

| | | | Summary of Reactions | | | | | |
|---|---|---|---|---|---|---|---|---|
| X. | RUN # | REACT | SAMPLE Wt. g | FIBRIL TYPE | T°C. | TIME | DRY Wt GAIN | $SO_3H$ CONC meq/g |
| 1A | 118-60A | Vap | 0.20 | CY | 110 | 15 m | 9.3% | 0.50 |
| 1B | 118-61A | Vap | 0.20 | BN | 100 | 30 m | 8.5% | 0.31 |
| 1C | 118-61B | Vap | 0.20 | BN | 65 | 15 m | 4.2% | 0.45 |
| 1D | 118-56A | Liq | 1.2 | CY | 50 | 10 m | | 0.33 |
| 1E | 118-56B | Liq | 1.0 | CY | 25 | 20 m | | 0.40 |

There was no significant difference in sulfonic acid content by reaction in the vapor phase or liquid phase. There was a temperature effect. Higher temperature of reaction (vapor phase) gives higher amounts of sulfones. In 118-61B, the 4.2% wt gain agreed with the sulfonic acid content (theoretical was 0.51 meq/g). Runs 60A and 61A had too high a wt gain to be accounted for solely by sulfonic acid content. It was therefore assumed that appreciable amounts of sulfones were also made.

2. ADDITIONS TO OXIDE-FREE FIBRIL SURFACES

Background techniques are described in Urry, G., *Elementary Equilibrium Chemistry of Carbon*, Wiley, New York 1989.

The surface carbons in fibrils behave like graphite, i.e., they are arranged in hexagonal sheets containing both basal plane and edge carbons. While basal plane carbons are relatively inert to chemical attack, edge carbons are reactive and must contain some heteroatom or group to satisfy carbon valency. Fibrils also have surface defect sites which are basically edge carbons and contain heteroatoms or groups.

The most common heteroatoms attached to surface carbons of fibrils are hydrogen, the predominant gaseous component during manufacture; oxygen, due to its high reactivity and because traces of it are very difficult to avoid; and $H_2O$, which is always present due to the catalyst. Pyrolysis at ~1000° C. in a vacuum will deoxygenate the surface in a complex reaction with unknown mechanism, but with known stoichiometry. The products are CO and $CO_2$, in a 2:1 ratio. The resulting fibril surface contains radicals in a $C_1$–$C_4$ alignment which are very reactive to activated olefins. The surface is stable in a vacuum or in the presence of an inert gas, but retains its high reactivity until exposed to a reactive gas. Thus, fibrils can be pyrolized at ~1000° C. in vacuum or inert atmosphere, cooled under these same conditions and reacted with an appropriate molecule at lower temperature to give a stable functional group. Typical examples are:

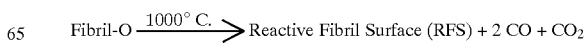

Fibril-O $\xrightarrow{1000° C.}$ Reactive Fibril Surface (RFS) + 2 CO + $CO_2$ followed by:

Fibril-R'COX  X = OH, —Cl, —NH$_2$, —H

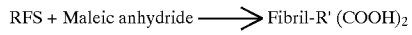

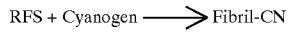

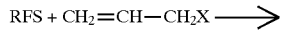

Fibril-R'CH$_2$X

X = —NH$_2$, —OH, —Halogen

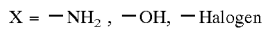

where R' is a hydrocarbon radical (alkyl, cycloalkyl, etc.)

Preparation B

Preparation of Functionalized Fibrils by Reacting Acrylic Acid with Oxide-Free Fibril Surfaces One gram of BN fibrils in a porcelain boat is placed in a horizontal 1" quartz tube fitted with a thermocouple and situated in a Lindberg tube furnace. The ends are fitted with a gas inlet/outlets. The tube is purged with dry, deoxygenated argon for 10 minutes, after which the temperature of the furnace is raised to 300° C. and held for 30 minutes. Thereafter, under a continued flow of argon, the temperature is raised in 100° C. increments to 1000° C., and held there for 16 hours. At the end of that time, the tube is cooled to room temperature (RT) under flowing argon. The flow of argon is then shunted to pass through a multi-neck flask containing neat purified acrylic acid at 50° C. and fitted with gas inlet/outlets. The flow of acrylic acid/argon vapors is continued at RT for 6 hours. At the end of that time, residual unreacted acrylic acid is removed, first by purging with argon, then by vacuum drying at 100° C. at <5" vacuum. The carboxylic acid content is determined by reaction with excess 0.100N NaOH and back-titrating with 0.100N HCl to an endpoint at pH 7.5.

Preparation C

Preparation of Functionalized Fibrils by Reacting Acrylic Acid with Oxide-Free Fibril Surfaces The procedure is repeated in a similar manner to the above procedure, except that the pyrolysis and cool-down are carried out at 10$^{-4}$ Torr vacuum. Purified acrylic acid vapors are diluted with argon as in the previous procedure.

Preparation D

Preparation of Functionalized Fibrils by Reacting Maleic Acid with Oxide-Free Fibril Surfaces The procedure is repeated as in Preparation B, except that the reactant at RT is purified maleic anhydride (MAN) which is fed to the reactor by passing argon gas through a molten MAN bath at 80° C.

Preparation E

Preparation of Functionalized Fibrils by Reacting Acryloyl Chloride with Oxide-Free Fibril Surfaces The procedure is repeated as in Preparation B, except that the reactant at RT is purified acryloyl chloride, which is fed to the reactor by passing argon over neat acryloyl chloride at 25° C. Acid chloride content is determined by reaction with excess 0.100N NaOH and back-titration with 0.100N HCl.

Pyrolysis of fibrils in vacuum deoxygenates the fibril surface. In a TGA apparatus, pyrolysis at 1000° C. either in vacuum or in a purified Ar flow gives an average wt loss of 3% for 3 samples of BN fibrils. Gas chromatographic analyses detected only CO and CO$_2$, in ~2:1 ratio, respectively. The resulting surface is very reactive and activated olefins such as acrylic acid, acryloyl chloride, acrylamide, acrolein, maleic anhydride, allyl amine, allyl alcohol or allyl halides will react even at room temperature to form clean products containing only that functionality bonded to the activated olefin. Thus, surfaces containing only carboxylic acids are available by reaction with acrylic acid or maleic anhydride; surf only acid chloride by reaction with acryloyl chloride; only aldehyde from acrolein; only hydroxyl from allyl alcohol; only amine from allyl amine, and only halide from allyl halide.

3. METALLATION

Background techniques are given in March, *Advanced Organic Chemistry*, 3rd ed., p. 545.

Aromatic C—H bonds can be metallated with a variety of organometallic reagents to produce carbon-metal bonds (C—M). M is usually Li, Be, Mg, Al, or Tl; however, other metals can also be used. The simplest reaction is by direct displacement of hydrogen in activated aromatics:

1. Fibril-H+R-Li→Fibril-Li+RH

The reaction may require additionally, a strong base, such as potassium t-butoxide or chelating diamines. Aprotic solvents are necessary (paraffins, benzene).

2. Fibril-H+AlR$_3$→Fibril-AlR$_2$+RH

3. Fibril-H+Tl(TFA)$_3$→Fibril-Tl(TFA)$_2$+HTFA  TFA= Trifluoroacetate HTFA=Trifluoroacetic acid The metallated derivatives are examples of primary singly-functionalized fibrils. However, they can be reacted further to give other primary singly-functionalized fibrils. Some reactions can be carried out sequentially in the same apparatus without isolation of intermediates.

4.

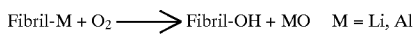   M = Li, Al

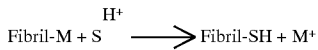

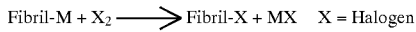   X = Halogen

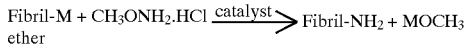

-continued

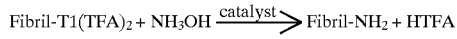

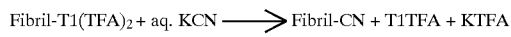

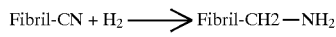

Preparation F

Preparation of Fibril-Li

One gram of CC fibrils is placed in a porcelain boat and inserted into a 1" quartz tube reactor which is enclosed in a Lindberg tube furnace. The ends of the tube are fitted with gas inlet/outlets. Under continuous flow of $H_2$, the fibrils are heated to 700° C. for 2 hours to convert any surface oxygenates to C—H bonds. The reactor is then cooled to RT under flowing $H_2$.

The hydrogenated fibrils are transferred with dry, de-oxygenated heptane (with $LiAlH_4$) to a 1 liter multi-neck round bottom flask equipped with a purified argon purging system to remove all air and maintain an inert atmosphere, a condenser, a magnetic stirrer and rubber septum through which liquids can be added by a syringe. Under an argon atmosphere, a 2% solution containing 5 mmol butyllithium in heptane is added by syringe and the slurry stirred under gentle reflux for 4 hours. At the end of that time, the fibrils are separated by gravity filtration in an argon atmosphere glove box and washed several times on the filter with dry, deoxygenated heptane. Fibrils are transferred to a 50 cc r.b. flask fitted with a stopcock and dried under $10^{-4}$ torr vacuum at 50° C. The lithium concentration is determined by reaction of a sample of fibrils with excess 0.100N HCl in DI water and back-titration with 0.100N NaOH to an endpoint at pH 5.0.

Preparation G

Preparation of Fibril-Tl(TFA)$_2$

One gram of CC fibrils are hydrogenated as in Preparation E and loaded into the multi-neck flask with HTFA which has been degassed by repeated purging with dry argon. A 5% solution of 5 mmol $Tl(TFA)_3$ in HTFA is added to the flask through the rubber septum and the slurry is stirred at gentle reflux for 6 hours. After reaction, the fibrils are collected and dried as in Preparation A.

Preparation H

Preparation of Fibril-OH (Oxygenated derivative containing only OH functionalization)

One half g of lithiated fibrils prepared in Preparation F are transferred with dry, deoxygenated heptane in an argon-atmosphere glove bag to a 50 cc single neck flask fitted with a stopcock and magnetic stirring bar. The flask is removed from the glove bag and stirred on a magnetic stirrer. The stopcock is then opened to the air and the slurry stirred for 24 hours. At the end of that time, the fibrils are separated by filtration and washed with aqueous MeOH, and dried at 50° C. at 5" vacuum. The concentration of OH groups is determined by reaction with a standardized solution of acetic anhydride in dioxane (0.252M) at 80° C. to convert the OH groups to acetate esters, in so doing, releasing 1 equivalent of acetic acid/mole of anhydride reacted. The total acid content, free acetic acid and unreacted acetic anhydride, is determined by titration with 0.100N NaOH to an endpoint at pH 7.5.

Preparation I

Preparation of Fibril-NH$_2$

One gram of thallated fibrils is prepared as in Preparation G. The fibrils are slurried in dioxane and 0.5 g triphenyl phosphine dissolved in dioxane is added. The slurry is stirred at 50° C. for several minutes, followed by addition at 50° C. of gaseous ammonia for 30 min. The fibrils are then separated by filtration, washed in dioxane, then DI water and dried at 80° C. at 5" vacuum. The amine concentration is determined by reaction with excess acetic anhydride and back-titration of free acetic acid and unreacted anhydride with 0.100N NaOH.

4. DERIVATIZED POLYNUCLEAR AROMATIC, POLYHETERONUCLEAR AROMATIC AND PLANAR MACROCYCLIC COMPOUNDS

The graphitic surfaces of fibrils allow for physical adsorption of aromatic compounds. The attraction is through van der Waals forces. These forces are considerable between multi-ring heteronuclear aromatic compounds and the basal plane carbons of graphitic surfaces. Desorption may occur under conditions where competitive surface adsorption is possible or where the adsorbate has high solubility.

Preparation J

Adsorption of Porphyrins and Phthalocyanines onto Fibrils

The preferred compounds for physical adsorption on fibrils are derivatized porphyrins or phthalocyanines which are known to adsorb strongly on graphite or carbon blacks. Several compounds are available, e.g., a tetracarboxylic acid porphyrin, cobalt (II) phthalocyanine or dilithium phthalocyanine. The latter two can be derivatized to a carboxylic acid form.

The loading capacity of the porphyrin or phthalocyanines can be determined by decoloration of solutions when they are added incrementally. The deep colors of the solutions (deep pink for the tetracarboxylic acid porphyrin in MeOH, dark blue-green for the Co(II) or the dilithium phthalocyanine in acetone or pyridine) are discharged as the molecules are removed by adsorption onto the black surface of the fibrils.

Loading capacities were estimated by this method and the footprints of the derivatives were calculated from their approximate measurements (~140 sq. Angstroms). For an average surface area for fibrils of 250 $m^2/g$, maximum loading will be ~0.3 mmol/g.

The tetracarboxylic acid porphyrin was analyzed by titration. The integrity of the adsorption was tested by color release in aqueous systems at ambient and elevated temperatures.

The fibril slurries were initially mixed (Waring blender) and stirred during loading. Some of the slurries were ultrasounded after color was no longer discharged, but with no effect.

After loading, Runs 169-11, -12, -14 and -19-1 (see Table II) were washed in the same solvent to remove occluded pigment. All gave a continuous faint tint in the wash effluent, so it was difficult to determine the saturation point precisely. Runs 168-18 and -19-2 used the calculated amounts of pigment for loading and were washed only very lightly after loading.

The tetracarboxylic acid porphyrin (from acetone) and the Co phthalocyanine (from pyridine) were loaded onto fibrils for further characterization (Runs 169-18 and -19-2, respectively).

Analysis of Tetracarboxylic Acid Porphyrin

Addition of excess base (pH 11–12) caused an immediate pink coloration in the titrating slurry. While this did not interfere with the titration, it showed that at high pH, porphyrin desorbed. The carboxylic acid concentration was determined by back titration of excess NaOH using Ph 7.5 as end-point. The titration gave a loading of 1.10 meq/g of acid, equivalent to 0.275 meq/g porphyrin.

Analysis of Cobalt or Dilithium Phthalocyanine

The concentrations of these adsorbates were estimated from decoloration experiments only. The point where the blue-green tint did not fade after 30 min was taken as the saturation-point.

A number of substituted polynuclear aromatic or polyheteronuclear aromatic compounds were adsorbed on fibril surfaces. For adhesion, the number of aromatic rings should be greater than two per rings/pendant functional group. Thus, substituted anthracenes, phenanthrenes, etc., containing three fused rings, or polyfuntional derivatives containing four or more fused rings can be used in place of the porphyrin or phthalocayanine derivatives. Likewise, substituted aromatic heterocycles such as the quinolines, or multiply substituted heteroaromatics containing four or more rings can be used.

Table II summarizes the results of the loading experiments for the three porphyrin/phthalocyanine derivatives.

TABLE II

Summary of Adsorption Runs

| EX. | RUN # | Adsorbate | Wgt. Fib, g | Solv. | Loading g/g | Form | meq/g Titration |
|---|---|---|---|---|---|---|---|
| 10A | 169-11 | TCAPorph | 19.6 mg | Acet | 0.18 g/g | Acid | na |
| 10B | 169-12 | TCAPorph | 33.3 mg | H$_2$O | 0.11 | Na Salt | na |
| 10C | 169-14 | DiLiPhth | 119.0 mg | Acet | 0.170 | Li | na |
| 10D | 16g-19-1 | CoPhth | 250.0 mg | Pyr | 0.187 | Co | 0.335 (cal) |
| 10E | 169-18 | TCAPorph | 1.00 g | Acet | 0.205 | Acid | 1.10 (T) |
| 10F | 169-19-2 | CoPhth | 1.40 g | Pyr | 0.172 | Co | 0.303 (cal) |

TCAPorph = Tetracarboxylic Acid Porphyrin (cal) = calculated
DiLiPhth = Dilithium Phthalocyanine (T) = Titration
CoPhth = Cobalt (II) Phthalocyanine

5. CHLORATE OR NITRIC ACID OXIDATION

Literature on the oxidation of graphite by strong oxidants such as potassium chlorate in conc. sulfuric acid or nitric acid, includes R. N. Smith, *Quarterly Review* 13, 287 (1959); M. J. D. Low, *Chem. Rev.* 60, 267 (1960)). Generally, edge carbons (including defect sites) are attacked to give mixtures of carboxylic acids, phenols and other oxygenated groups. The mechanism is complex involving radical reactions.

Preparation K

Preparation of Carboxylic Acid-Functionalized Fibrils Using Chlorate.

The sample of CC fibrils was slurried in conc. H$_2$SO$_4$ by mixing with a spatula and then transferred to a reactor flask fitted with gas inlet/outlets and an overhead stirrer. With stirring and under a slow flow of argon, the charge of NaClO$_3$ was added in portions at RT over the duration of the run. Chlorine vapors were generated during the entire course of the run and were swept out of the reactor into a aqueous NaOH trap. At the end of the run, the fibril slurry was poured over cracked ice and vacuum filtered. The filter cake was then transferred to a Soxhlet thimble and washed in a Soxhlet extractor with DI water, exchanging fresh water every several hours. Washing was continued until a sample of fibrils, when added to fresh DI water, did not change the pH of the water. The fibrils were then separated by filtration and dried at 100° C. at 5" vacuum overnight.

The carboxylic acid content was determined by reacting a sample with excess 0.100N NaOH and back-titrating with 0.100$^n$ HCl to an endpoint at pH 7.5. The results are listed in Table III.

TABLE III

Summary of Direct Oxidation Runs

| | | Components, g | | | Time | | Rec | Acid, |
|---|---|---|---|---|---|---|---|---|
| Ex. | RUN # | Fibrils | NaClO$_3$ cc | H$_2$SO$_4$ | hours | Wash Ph | Wgt | meq/g |
| 11A | 168-30 | 10.0 | 8.68 | 450 | 24 | 5.7 | 10.0 | 0.78 |
| 11B | 168-36 | 12.0 | 13.9 | 600 | 24 | 5.9 | 13.7 | 0.75 |

Preparation L

Preparation of Carboxylic Acid-Functionalized Fibrils Using Nitric Acid.

A weighed sample of fibrils was slurried with nitric acid of the appropriate strength in a bound bottom multi-neck indented reactor flask equipped with an overhead stirrer and a water condenser. With constant stirring, the temperature was adjusted and the reaction carried out for the specified time. Brown fumes were liberated shortly after the temperature exceeded 70° C., regardless of acid strength. After the reaction, the slurry was poured onto cracked ice and diluted with DI water. The slurry was filtered and excess acid removed by washing in a Soxhlet extractor, replacing the reservoir with fresh DI water every several hours, until a slurried sample gave no change in Ph from DI water. The fibrils were dried at 100° C. at 5" vacuum overnight. A weighed portion of fibrils was reacted with standard 0.100N NaOH and the carboxylic acid content determined by back-titration with 0.100N HCl. Surface oxygen content was determined by XPS. Dispersibility in water was tested at 0.1 wt % by mixing in a Waring Blender at high for 2 min. Results are summarized in Table IV.

Soc. 86, 1839 (1964), using N-Hydroxysuccinimide (NHS) to activate carboxylic acids for amidation were used.

Preparation M

Preparation of Secondary Derivatives of Functionalized Fibrils

N, N'-Carbonyl Diimidazole

Clean, dry, aprotic solvents (e.g., toluene or dioxane) are required for this procedure. Stoichiometric amounts of reagents are sufficient. For esters, the carboxylic acid compound is reacted in an inert atmosphere (argon) in toluene with a stoichiometric amount of CDI dissolved in toluene at R.T. for 2 hours. During this time, $CO_2$ is evolved. After two hours, the alcohol is added along with catalytic amounts of Na ethoxide and the reaction continued at 80° C. for 4 hr. For normal alcohols, the yields are quantitative. The reactions are:

TABLE IV

Summary of Direct Oxidation Runs

| | | COMPONENTS | | | | | | ESCA, at % | | Disp |
|---|---|---|---|---|---|---|---|---|---|---|
| | Gms. | cc | Acid | Temp. | | Wgt. | COOH | | | |
| Ex. | Fibrils | Acid | Conc. | °C. | Time | Loss | meq/g | C | O | H2O |
| 12A | 1 (BN) | 300 | 70% | RT | 24 hr | 0 | <0.1 | 98 | 2 | P |
| 12B | 1 (BN) | 300 | 15 | rflx | 48 | <5% | <0.1 | not analyzed | | P |
| 12C | 20 (BN) | 1.0 1 | 70 | rflx | 7 | 25% | 0.8 | not analyzed | | G |
| 12D | 48 (BN) | 1.0 1 | 70 | rflx | 7 | 20% | 0.9 | not analyzed | | G |

P = Poor;
G = Good

6. SECONDARY DERIVATIVES OF FUNCTIONALIZED FIBRILS

Carboxylic Acid-functionalized Fibrils

The number of secondary derivatives which can be prepared from just carboxylic acid is essentially limitless. Alcohols or amines are easily linked to acid to give stable esters or amides. If the alcohol or amine is part of a di- or poly-functional molecule, then linkage through the O- or NH- leaves the other functionalities as pendant groups. Typical examples of secondary reagents are:

| GENERAL FORMULA | PENDANT GROUP | EXAMPLES |
|---|---|---|
| HO—R, R = alkyl, aralkyl, aryl, fluoroethanol, polymer, SiR'$_3$ | R— | Methanol, phenol, trifluorocarbon, OH-terminated Polyester, silanols |
| H$_2$N—R R = same as above | R— | Amines, anilines, fluorinated amines, silylamines, amine terminated polyamides |
| Cl—SiR$_3$ | SiR$_3$— | Chlorosilanes |
| HO—R—OH, R = alkyl, aralkyl, CH$_2$O— | HO— | Ethyleneglycol, PEG, Pentaerythritol, bis-Phenol A |
| H$_2$N—R—NH$_2$, R = alkyl, aralkyl | H$_2$N— | Ethylenediamine, polyethyleneamines |
| X—R—Y, R = alkyl, etc; X = OH or NH$_2$; Y = SH, CN, C=O, CHO, alkene, alkyne, aromatic, heterocycles | Y— | Polyamine amides, Mercaptoethanol |

The reactions can be carried out using any of the methods developed for esterifying or aminating carboxylic acids with alcohols or amines. Of these, the methods of H. A. Staab, Angew. Chem. Internat. Edit., (1), 351 (1962) using N,N'-carbonyl diimidazole (CDI) as the acylating agent for esters or amides, and of G. W. Anderson, et al., J. Amer. Chem.

1. R—COOH+Im—CO—Im→R—CO—Im+HIm+$CO_2$, Im=Imidazolide, HIm=Imidazole

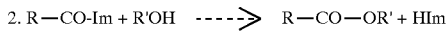

Amidation of amines occurs uncatalyzed at RT. The first step in the procedure is the same. After evolution of $CO_2$, a stoichiometric amount of amine is added at RT and reacted for 1–2 hours. The reaction is quantitative. The reaction is:

3. R—CO—Im+R'NH$_2$→R—CO—NHR+HIm

N-Hydroxysuccinimide

Activation of carboxylic acids for amination with primary amines occurs through the N-hydroxysuccinamyl ester; carbodiimide is used to tie up the water released as a substituted urea. The NHS ester is then converted at RT to the amide by reaction with primary amine. The reactions are:

1. R—COOH+NHS+CDI→R—CONHS+Subst. Urea
2. R—CONHS+R'NH$_2$→R—CO—NHR'

Silylation

Trialkylsilylchlorides or trialkylsilanols react immediately with acidic H according to:

R—COOH+Cl—SiR'$_3$→R—CO—SiR'$_3$+HCl

Small amounts of Diaza-1,1,1-bicyclooctane (DABCO) are used as catalysts. Suitable solvents are dioxane and toluene.

Preparation N

Preparation of Ester/Alcohol Derivatives from Carboxylic Acid-Functionalized Fibrils The carboxylic acid functionalized fibrils were prepared as in Preparation K. The carboxylic acid content was 0.75 meq/g. Fibrils were reacted with a stoichiometric amount of CDI in an inert atmosphere with toluene as solvent at R.T. until $CO_2$ evolution ceased. Thereafter, the slurry was reacted at 80° C. with a 10-fold molar excess of polyethyleneglycol (MW 600) and a small amount of NaOEt as catalyst. After two hours reaction, the fibrils were separated by filtration, washed with toluene and dried at 100° C.

Preparation O

Preparation of Amide/Amine Derivatives from Carboxylic Acid-Functionalized Fibrils (177-041-1)

0.242 g of chlorate-oxidized fibrils (0.62 meq/g) was suspended in 20 ml anhydrous dioxane with stirring in a 100 ml RB flask fitted with a serum stopper. A 20-fold molar excess of N-Hydroxysuccinimide (0.299 g) was added and allowed to dissolve. This was followed by addition of 20-fold molar excess of 1-ethyl-3-(3-dimethylaminopropyl)-carbodiimide (EDAC) (0.510 g), and stirring was continued for 2 hr at RT. At the end of this period stirring was stopped, and the supernatant aspirated and the solids were washed with anhydrous dioxane and MeOH and filtered on a 0.45 micron polysulfone membrane. The solids were washed with additional MeOH on the filter membrane and vacuum-dried until no further weight reduction was observed. Yield of NHS-activated oxidized fibrils was 100% based on the 6% weight gain observed.

100 μl ethylenediamine (en) was added to 10 ml 0.2M $NaHCO_3$ buffer. An equivalent volume of acetic acid (HOAC) was added to maintain the pH near 8. NHS-activated oxidized fibrils (0.310 g) was added with vigorous stirring and reacted for 1 hr. An additional 300 μl of en and 300 μl HOAc was added for an additional 10 min. The solution was filtered on 0.45 micron polysulfone membrane and washed successively with $NaHCO_3$ buffer, 1% HCl, DI water and EtOH. The solids were dried under vacuo overnight. The HCl salt was converted back to the free amine by reaction with NaOH (177-046-1) for further analysis and reactions.

ESCA was carried out to quantify the amount of N present on the aminated fibrils ($GF/NH_2$). ESCA analysis of 177-046-1 showed 0.90 at % N (177-059). To further assess how much of this N is present as both accessible and reactive amine groups, a derivative was made by the gas phase reaction with pentafluorobenzaldehyde to produce the corresponding Schiff Base linkages with available primary amine groups. ESCA analysis still showed the 0.91 at % N, as expected, and 1.68 at % F. This translates into a 0.34 at % of N present as reactive primary amine on the aminated fibrils (5 F per pentafluorobenzaldehyde molecule). A level of 0.45 at % N would be expected assuming complete reaction with the free ends of each N. The observed level indicates a very high yield from the reaction of N with NHS-activated fibril and confirms the reactivity of the available free amine groups.

At the level of 0.34 at % N present as free amine calculated from the ESCA data, there would be almost complete coverage of the fibrils by the free amine groups allowing coupling of other materials.

Preparation P

Preparation of Silyl Derivative from Carboxylic Acid-Functionalized Fibrils

Acid functionalized fibrils prepared as in Preparation K were slurried in dioxane in an inert atmosphere. With stirring, a stoichiometric amount of chlorotriethyl silane was added and reacted for 0.5 hr, after which several drops of a 5% solution of DABCO in dioxane was added. The system was reacted for an additional hour, after which the fibrils were collected by filtration and washed in dioxane. The fibrils were dried at 100° C. in V" vacuum overnight.

Table V summarizes the secondary derivative preparations. The products were analyzed by ESCA for C, O, N, Si and F surface contents.

TABLE V

Summary of Secondary Derivative Preparations

| | | ESCA ANALYSIS, ATOM % | | | | |
|---|---|---|---|---|---|---|
| REACTANT | PENDANT GROUP | S | C | N | O | Si | F |
| As Grown | — | — | 98.5 | — | 1.5 | — | — |
| Chlorate Oxidized | —COOH, C=O, C—OH | — | 92.4 | — | 7.6 | — | — |
| $H_2N$—$C_2H_4$—$NH_2$ | —$CONHC_2H_4NH_2$ | — | 99.10 | 0.90 | — | — | — |
| | —$CONHC_2H_4N = OC_6F_5$ | — | 97.41 | 0.91 | — | — | 1.68 |

Preparation Q

Preparation of silyl Derivative from Carboxylic Acid-Functionalized Fibrils

Acid functionalized fibrils prepared as in Preparation K are slurried in dioxane in an inert atmosphere. With stirring, a stoichiometric amount of chlorotriethyl silane is added and reacted for 0.5 hr, after which several drops of a 5% solution of DABCO in dioxane is added. The system is reacted for an additional hour, after which the fibrils are collected by filtration and washed in dioxane. The fibrils are dried at 100° C. in 5" vacuum overnight.

Table VI summarizes the secondary derivative preparations. Products are analyzed by ESCA. The analysis confirms the incorporation of the desired pendant groups. The products are analyzed by ESCA for C, O, N, Si and F surface contents.

TABLE VI

Summary of Secondary Derivative Preparations

| | | ESCA ANALYSIS, ATOM % | | | | |
|---|---|---|---|---|---|---|
| REACTANT | PENDANT GROUP | S | C | N | O | Si | F |
| $CF_3CH_2OH$ | —$COOCH_2CF3$ | NOT ANALYZED | | | | | |
| PolyEG-600 | —CO—($OC_2H_4O$—)H | NOT ANALYZED | | | | | |
| HO—$C_2H_4$—SH | —$COOC_2H4SH$ | | | | | | |
| Cl—$SiEt_3$ | —$COSiEt_3$ | | | | | | |

Sulfonic Acid-Functionalized Fibrils

Aryl sulfonic acids, as prepared in Preparation A can be further reacted to yield secondary derivatives. Sulfonic acids can be reduced to mercaptans by $LiAlH_4$ or the combination of triphenyl phosphine and iodine (March, J.P., p. 1107). They can also be converted to sulfonate esters by reaction with dialkyl ethers, i.e., Fibril-$SO_3H$+R—O—R→Fibril-$SO_2$OR+ROH Fibrils Functionalized by Electrophilic Addition to Oxygen-Free Fibril Surfaces or by Metallization The primary products obtainable by addition of activated electrophiles to oxygen-free fibril surfaces have pendant —COOH, —COCl, —CN, —$CH_2NH_2$, —$CH_2$OH, —$CH_2$— Halogen, or HC=O. These can be converted to secondary derivatives by the following:

Fibril-COOH→see above. Fibril-COCl (acid chloride)+ HO—R—Y→F—COO—R—Y (Sec. 4/5)

Fibril-COCl+$NH_2$—R—Y→F—CONH—R—Y

Fibril-CN+$H_2$→F—$CH_2$—$NH_2$

Fibril-$CH_2NH_2$+HOOC—R—Y→F—$CH_2$NHCO—R—Y

Fibril-$CH_2NH_2$+O=CR—R'Y→F—$CH_2$N=CR—R'—Y

Fibril-$CH_2$OH+O(COR—Y)$_2$→F—$CH_2$OCOR—Y

Fibril-$CH_2$OH+HOOC—R—Y→F—$CH_2$OCOR—Y

Fibril-$CH_2$-Halogen+$Y^-$→F—$CH_2$—Y+$X^-Y^-$=$NCO^{31}$, —OR $^-$Fibril-C=O+$H_2$N—R—Y→F—C=N—R—Y Fibrils Functionalized by Adsorption of Polynuclear or Polyheteronuclear Aromatic or Planar Macrocyclic Compounds Dilithium phthalocyanine: In general, the two $Li^+$ ions are displaced from the phthalocyanine (Pc) group by most metal (particularly multi-valent) complexes. Therefore, displacement of the $Li^+$ ions with a metal ion bonded with non-labile ligands is a method of putting stable functional groups onto fibril surfaces. Nearly all transition metal complexes will displace $Li^+$ from Pc to form a stable, non-labile chelate. The point is then to couple this metal with a suitable ligand.

Cobalt (II) Phthalocyanine

Cobalt (II) complexes are particularly suited for this. $Co^{++}$ ion can be substituted for the two $Li^+$ ions to form a very stable chelate. The $Co^{++}$ ion can then be coordinated to a ligand such as nicotinic acid, which contains a pyridine ring with a pendant carboxylic acid group and which is known to bond preferentially to the pyridine group. In the presence of excess nicotinic acid, Co(II)Pc can be electrochemically oxidized to Co(III)Pc, forming a non-labile complex with the pyridine moiety of nicotinic acid. Thus, the free carboxylic acid group of the nicotinic acid ligand is firmly attached to the fibril surface.

Other suitable ligands are the aminopyridines or ethylenediamine (pendant $NH_2$), mercaptopyridine (SH), or other polyfunctional ligands containing either an amino- or pyridyl- moiety on one end, and any desirable function on the other.

7. 3-DIMENSIONAL STRUCTURES

The oxidized fibrils are more easily dispersed in. aqueous media than unoxidized fibrils. Stable, porous 3-dimensional structures with meso- and macropores (pores >2 nm) are very useful as catalysts or chromatography supports. Since fibrils can be dispersed on an individualized basis, a well-dispersed sample which is stabilized by cross-links allows one to construct such a support. Functionalized fibrils are ideal for this application since they are easily dispersed in aqueous or polar media and the functionality provides cross-link points. Additionally, the functionality provides points to support the catalytic or chromatographic sites. The end result is a rigid, 3-dimensional structure with its total surface area accessible with functional sites on which to support the active agent.

Typical applications for these supports in catalysis include their use as a highly porous support for metal catalysts laid down by impregnation, e.g., precious metal hydrogenation catalysts. Moreover, the ability to anchor molecular catalysts by tether to the support via the functionality combined with the very high porosity of the structure allows one to carry out homogeneous reactions in a heterogeneous manner. The tethered molecular catalyst is essentially dangling in a continuous liquid phase, similar to a homogeneous reactor, in which it can make use of the advantages in selectivities and rates that go along with homogeneous reactions. However, being tethered to the solid support allows easy separation and recovery of the active, and in many cases, very expensive catalyst.

These stable, rigid structures also permits carrying out heretofore very difficult reactions, such as asymmetric syntheses or affinity chromatography by attaching a suitable enantiomeric catalyst or selective substrate to the support. Derivatization through Metallo-Pc or Metallo-porphyrin complexes also allows for retrieval of the ligand bonded to the metal ion, and furthermore, any molecule which is bonded to the ligand through the secondary derivatives. For example, in the case where the 3-dimensional structure of functionalized fibrils is an electrode, or part of an electrode, and the functionalization has resulted from adsorption of Co(II)Pc, electrochemical oxidation of Co(II) to Co(III) in the presence of nicotinic acid will produce a non-labile Co(III)-pyridyl complex with a carboxylic acid as the pendent group. Attaching a suitable antigen, antibody, catalytic antibody, or other site-specific trapping agent will permit selective separations of molecules (affinity chromatography) which are otherwise very difficult to achieve. After washing the electrode to remove occluded material, the Co(III) complex containing the target molecule can be electrochemically reduced to recover the labile Co(II) complex. The ligand on Co(II) containing the target molecule can then be recovered by mass action substitution of the labile CO(II) ligand, thereby effecting a separation and recovery of molecules which are otherwise very difficult or expensive to perform (e.g., chiral drugs).

Another example of 3-dimensional structures are fibril-ceramic composites.

Preparation R

Preparation of Alumina-Fibril Composites (185-02-01)

One g of nitric acid oxidized fibrils (185-01-02) was highly dispersed in 100 cc DI water using and U/S disintegrator. The fibril slurry was heated to 90° C. and a solution of 0.04 mol aluminum tributoxide dissolved in 20 cc propanol was slowly added. Reflux was continued for 4 hr, after which the condenser was removed to drive out the alcohol. After 30 min the condenser was put back and the slurry refluxed at 100° C. overnight. A black sol with uniform appearance was obtained. The sol was cooled to RT and after one week, a black gel with a smooth surface was formed. The gel was heated at 300° C. in air for 12 hr.

The alumina-fibril composites were examined by SEM. Micrographs of cracked surfaces showed a homogeneous dispersion of fibrils in the gel.

Preparation S

Preparation of Silica-Fibril Composites (173-85-03)

Two g of nitric acid oxidized fibrils (173-83-03) were highly dispersed on 200 cc ethanol using ultrasonification. A solution of 0.1 mol tetraethoxysilane dissolved in 50 cc ethanol was slowly added to the slurry at RT, followed by 3 cc conc. HCL. The mixture was heated to 85° C. and maintained at that temperature until the volume was reduced to 100 cc. The mixture was cooled and set aside until it formed a black solid gel. The gel was heated at 300° C. in air.

The silica-fibril composites were examined by SEM. Micrographs of cracked surfaces showed a homogeneous dispersion of fibrils in the gel.

Similar preparations with other ceramics, such as zirconia, titania, rare earth oxides as well as ternary oxides can be prepared.

As illustrated by the foregoing description and examples, the invention has application in the formulation of a wide variety of functionalized nanotubes.

The terms and expressions which have been employed are used as terms of description and not of limitations, and there is no intention in the use of such terms or expressions of excluding any equivalents of the features shown and described as portions thereof, its being recognized that various modifications are possible within the scope of the invention

DESCRIPTION OF PREFERRED EMBODIMENTS OF THE INVENTION

While a wide range of nanotubes can be employed in the assays of the invention, generally the nanotubes have a density of from 1.0 to 5.0 g/mL and preferably have a density of from 1.1 to 2 g/mL. Choice of the optimum density is within the skill of the art, the rate of settling in gravity-driven assays being a trade-off between the speed of the assay and the desire to create a uniform layer of complex on the electrode surface.

Nanotubes having a wide range of mean diameters can also be employed. Particles having a mean diameter of from 0.001 to 100 $\mu$m can be used and preferably the particles have a mean diameter of from 0.01 to 10 $\mu$m. Lengths of the nanotubes are at least five times the diameter.

Wide ranges of concentration of particles in the assay composition can also be employed. For example, the concentration can range from $1\times10^{-9}$ to $1\times10^{-2}$ g/mL to preferably from $1\times10^{-8}$ to $1\times10^{-3}$ g/mL. Desirably, the density of the particles, their size and their concentration is selected such that the particles settle at a rate of at least 0.5 mm/min and preferably at a faster rate.

In the filtration mode of performing the invention, the filtration means desirably has a pore size, measured as mean diameter, from broadly 0.01 to 90% of the mean diameter of the particles and preferably from 10% to 90% of that diameter.

The nanotubes may be paramagnetic or ferromagnetic and may be coated with various materials to which binding compounds are coupled so that the magnetic particle can be used in assays. Desirably the magnetic nanotubes used in the invention have a susceptibility of at least 0.001 cgs units and desirably the susceptibility is at least 0.01 cgs units. The magnetic nanotubes may have a broad range of densities, i.e. from substantially less than that of water, 0.01, to 5 g/mL and preferably from 0.5 to 2 g/mL. The particle sizes can range from 0.001 to 100 $\mu$m and preferably from 0.01 to 10 $\mu$m. The concentration of the particles may range broadly from $1\times10^{-9}$ to $1\times10^{-2}$ g per mL and preferably is from $1\times10^{-8}$ to $1\times10^{-3}$ g per mL.

Desirably the magnetic nanotubes which are used have a low magnetic remanence, as described for example EP 0,180,384, so that after the magnetic field is removed from the electrode surface, the nanotubes demagnetize and can be swept out of the assay cell. Desirably the density, concentration and size of the magnetic nanotubes is chosen such that the settling time is at least 0.5 mm/min and desirably it is above that rate. In operation of the magnetic cell it is often desirable to remove the magnet means from the electrode surface prior to inducing electrochemiluminescence in order not to interfere with the operation of the photomultiplier tube.

Assays

A variety of assays can be performed using the methods of the invention. An assay was conducted using functionalized carbon nanotubes. The assay involved an ECL detection of hydrolytic enzymes using carbon nanotubes (fibrils). Carbon nanotubes (fibrils) were chemically modified with substrates of hydrolytic enzymes. On the end of the substrate farthest from the fibril was attached a derivative of $Ru(bpy)_3^{2+}$. The general structure of the solid phase was as follows: fibril-substrate (scissile bond)-$Ru(bpy)_3^{2+}$. If an enzyme is present that cleaves the scissile bond, the $Ru(bpy)_3^{2+}$ end of the substrate is released into solution by the action of the enzyme. Following mixture and incubation of the fibrils with the enzyme, the fibrils are removed from the solution (by filtration or centrifugation). The ECL of the remaining solution is measured. If the enzyme was present, the $Ru(bpy)_3^{2+}$ end of the substrate will be present in the solution and will emit light. Thus, presence of the specific enzyme results in light emission from the solution phase of the mixture. The assay is a novel ECL assay for proteases because it does not involve antibodies (it is not an immunoassay). Thus, it has the advantage of being an assay for enzyme activity rather than an assay for the enzyme's presence (the enzyme may be inactive). Moreover, the assay uses fibrils as a solid support. Fibrils are attractive because of their high surface area and amenability in attaching biomolecules such as enzyme substrates. In addition, the functionalized fibrils may be formed into a flow through membrane (mat). The enzyme mixture could rapidly flow through to release $Ru(bpy)_3^{2+}$ and make the assay rapid and convenient.

A DNA probe assay using fibrils and ECL was conducted. Carbon nanotubes (fibrils) were used as a solid support in DNA probe assays as a separation media to separate analyte from complex mixtures which may include biological fluids and added reagents. Fibrils were modified with avidin (or streptavidin), either by covalent attachment (via NHS ester) or by adsorption to alkyl fibrils. Biotinylated ssDNA (the "analyte") bound to the avidin fibrils and was detected by the ECL of a complementary single stranded oligonucleotide which had been labeled with $Ru(bpy)_3^{2+}$.

One format for detecting a natural (non-biotinylated) DNA fragment is a competitive format where the $Ru(bpy)_3^{2+}$-labeled oligo can bind to either the natural DNA or to an introduced biotinylated DNA. Thus, the more analyte that is present (non-biotinylated DNA), the less labeled oligo remains to bind to the biotinylated DNA, which when captured on avidin fibrils gives an ECL signal.

This represents the first time carbon nanotubes have been used in DNA analysis. The advantages are: (1) carbon nanotubes have a very high surface area which means that less solid support is necessary than with other solid supports. (2) Fibrils are electrically conductive, which is an attractive property for a solid support in ECL applications, in which the solid support rests against an electrode. Being electrically conductive, more of the surface area is in electrochemical contact than with other supports which are not conductive.

An ECL-based immunoassay using immobilized antibodies on carbon nanotubes (fibrils) would be advantageous. Antibody fibrils could be used in ECL applications in a competitive immunoassay format (where there is a competition between the analyte and $Ru(bpy)_3^{2+}$-labeled analyte for binding to the antibody fibrils) or in a sandwich format (where a $Ru(bpy)_3^{2+}$-labeled secondary antibody binds to the antibody fibril-analyte complex). In both cases, ECL light emission signals the presence or absence of the analyte of interest. Antibody can be immobilized on fibrils by several different methods, by covalent or non-covalent means. For non-covalent immobilization, antibody is adsorbed onto unmodified fibrils or onto fibrils modified to enhance adsorption characteristics. Such modified fibrils have hydrophobic appendages (alkyl chains or phenyl-alkyl chains). Covalent immobilization of antibodies onto fibrils can be achieved by three different methods: by NHS ester activation of carboxylated fibrils, by reductive amination of antibody carbohydrate groups, and by sulfhydryl/maleimido fibrils reacting with reduced or maleimido-modified antibodies. The immobilization of antibodies on carbon fibrils is advantageous. Antibody fibrils have a number of unique properties compared with other solid supports for antibodies. These advantages include high surface area per weight, electrical conductivity (especially in ECL applications), and chemical and physical stability.

Carbon nanotubes were used as ECL-based biosensors. Bifunctional fibrils were prepared wherein a derivative of the enzyme cofactor NAD+ was attached to one functional group and a derivative of $Ru(bpy)_3^{2+}$ was attached to the other functional group (COOH). The biosensor fibrils were mixed with a solution that contained the analyte (a dehydrogenase, in this case G6PDH) and the substrate of the dehydrogenase was added (in this case, glucose-6-phosphate). Following a time suitable for the enzyme to react with its substrate and convert the NAD+ groups on the fibrils to NADH, the ECL of the fibrils were measured in an ECL instrument. A change in the ECL properties of the biosensor fibrils indicated the presence of the enzyme, G6PDH. The following advantages were found: (1) The close proximity of the NAD+ and $Ru(bpy)_3^{2+}$ coreactants results in an intramolecular ECL reaction which is more efficient than intermolecular ECL reactions. (2) The ECL active reagents (the NAD+ and $Ru(bpy)_3^{2+}$ coreactants) are immobilized on fibrils, which allows them to settle or be magnetically drawn to the ECL electrode, resulting in enhanced light emission. (3) Fibrils have an extremely high surface area, such that large amounts of the coreactants (NAD+ and $Ru(bpy)_3^{2+}$ can be immobilized, theoretically enhancing light output during detection of dehydrogenases. (4) Fibrils are electrically conductive - when the biosensors reach the electrode, much of their surface area which is not in actual contact with the electrode can receive voltage and participate in ECL reactions. (5) The biosensor is designed to detect dehydrogenases that use either NAD+ or NADH as a cofactor. Many of these enzymes exist and could be detected using this invention.

Carbon fibrils were used as a solid support for an enzyme biosensor. Because the enzyme biosensor is water soluble, it can only be used once, unless it is immobilized (immobilization allows it to be recovered from the analyte solution). U.S. application Ser. No. 08/467,712 discusses and claims immobilization to a solid support and to a (solid) electrode. The present application demonstrates the use of carbon fibrils as the solid support. The enzyme biosensor can be attached to fibrils by adsorption. The fibrils may either be unmodified fibrils or, preferably, chemically modified fibrils. Chemical modification of the fibrils is preferably by alkylation. Adsorption of the biosensor is carried out by incubation with mixing of the enzyme biosensor and the alkylated fibrils. Fibrils as a solid support are novel and attractive because: (1) they have a high surface area of immobilization resulting in potentially high light emission, (2) proteins such as the biosensor can be conveniently adsorbed without covalent chemistry, (3) fibrils are electrically conductive which may enhance ECL when in contact with an electrode, (4) fibrils themselves may be made into electrodes, in which case the electrode itself if a biosensor support.

Magnetically-susceptible particles are useful as devices for separations. Separations of, for example, a specific analyte from a complex mixture are useful in the diagnostics industry where an analyte may be present in a complex mixture such as blood. Because the complex mixture may interfere with the analysis of the analyte, it is desirable to bind the analyte to a solid surface so that the complete mixture can be washed away from the analyte, thus allowing its determination. If the desired analyte can specifically bind to a magnetically-susceptible particle, that particle can be held by a magnet, allowing washing of the complex mixture away from the analyte, which can then be detected. Because fibrils are particles that can specifically and efficiently bind biomolecules, magnetically-susceptible fibrils advantageously are used as solid phase separation devices, especially in ECL analyses. Fibrils were made magnetically-susceptible by performing treatments, such as chemical reactions or changes of the solvent that they are suspended in (for example, from water to DMF). It is speculated that such manipulations cause changes in the physical aggregation of multiples of fibrils. Because fibrils have some (approximately 0.5% by weight) iron in them, they have the ability, once aggregated, to be substantially magnetically susceptible. Several treatments were carried out which increase the magnetic susceptibility of fibrils. These treatments are postulated to cause changes in the aggregation of fibrils, which in turn, cause them to be efficiently drawn to a magnet. Magnetically-susceptible fibrils have at least two unique advantages. First, they have a very high surface area per weight. Thus, less fibrils need to be used (as compared to for example Dynal beads) to achieve the same result. Secondly, fibrils are electrically conductive. Thus, they have an advantage in applications such as ECL where the magnetically susceptible particles are held to an electrode. Thus, being electrically conductive, they actually become part of the electrode, enhancing the light output efficiency.

EXAMPLES (1) Instrumentation

A flow-through apparatus, employing three electrodes, as described in FIGS. 1 and 2, was used.

Working Electrode—Au disk, 3 mm diameter

Counter Electrode—Au disk, 3 mm diameter

Reference Electrode—Ag/AgCl

Teflon Gasket (0.15"thick)

Plexiglas Faceplate

Inlet Tubing=0.042" id polypropylene

Aspiration Rates:variable from 0.01 to 5 mL/min

Potentiostat: microprocessor controlled Luminometer using Hamamatsu R374 PMT (low gain red sensitive tube); PMT Voltage variable 0–1400 V (2) ECL Measurement Cycle (three electrode cell operation)

The ECL measurement cycle consists of three steps: (1) preconditioning, (2) measuring, and (3) cleaning. The preconditioning step involves the application of a voltage triangle wave of 0.0 V to +2.2 V to −1.0 V to +0.6 V at 2.0 V/sec. The measurement step involves the application of a triangle waveform from +0.6 to +2.8 V to +2.0 V at 1.0 V/s. The cleaning step involves the application of a voltage square wave from +0.0 V to +3.0 V to −0.5 V to 0.0 V. All voltages are relative to the Ag/AgCl reference electrode.

EXAMPLE 1

Ruthenium Tag Peptide Fibril Synthesis

This example shows the synthesis of an enzyme detection reagent in ECL Analyzer. Ruthenium peptide fibrils synthesis: Tetrapeptide of FmocNH-Gly-Lys($N^\epsilon$-CBZ)-Phe-Gly-COOH was synthesized by conventional solution phase methods and this peptide (71 mg, 0.093 mmol) was reacted with a primary amine derivatized version of Ru(bpy)$_3^{2+}$ (IGEN, Inc., Gaithersburg, Md.) (73 mg, 0.078 mmol), EDC (17.8 mg, 0.093 mmol) was used as a activating reagent, and HOBT (12.58 mg, 0.093 mmol) as a catalyst. The product FmocNH-Gly-Lys(NE-CBZ)-Phe-Gly-CO-NH-Tag (170 mg, 0.223 mmol) was deprotected with piperidine (96 ml) and methylene chloride (1.1 ml). The structure of the tetrapeptide-Ru(bpy)$_3^{2+}$ compound was confirmed by 1H-NMR. To the solution of tetrapeptide-Ru(bpy)$_3^{2+}$ (5 mg, 0.003 mmol) in methylene chloride (2 ml) was added carboxyl fibrils (54 mg). Then EDC (5.8 mg, 0.03 mmol) and HOBT (4 mg, 0.03 mmol) were added. The reaction mixture was stirred overnight. The fibrils were extensively washed with water, methanol, acetonitrile and methylene chloride. The product fibrils were treated with trimethylsilyl iodide (TMSI, 1 ml) in acetonitrile (4 ml) for 3 hours at 40° C. The final product fibrils were extensively washed with water, methanol, acetonitrile, IGEN standard ECL assay buffer (IGEN, Inc., Gaithersburg, Md.) and methylene chloride.

EXAMPLE 2

Figure 3:
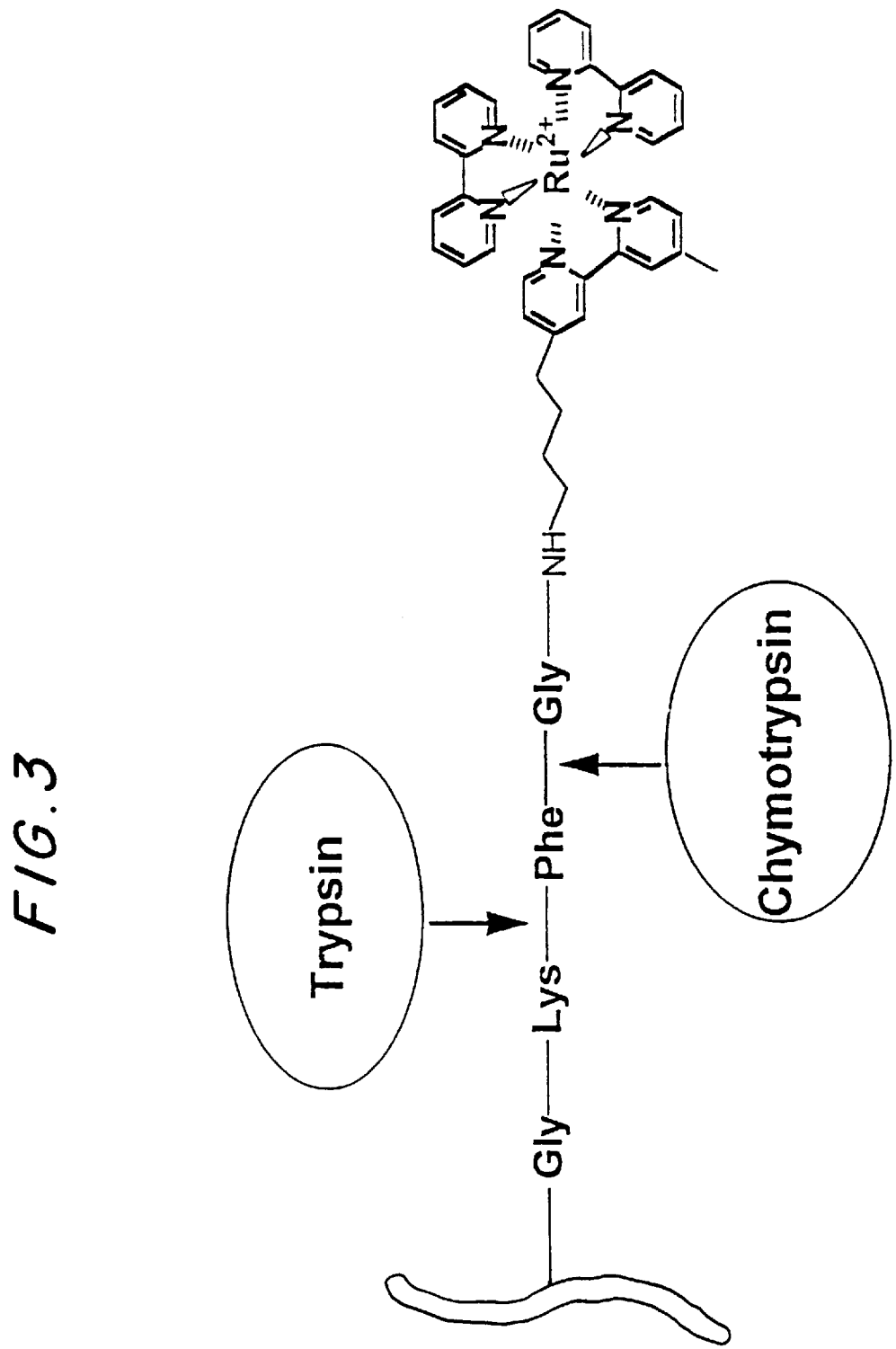
FIG. 3 is a schematic representation showing the specific enzyme hydrolysis sites on $Ru(bpy)_3^{2+}$-labeled peptide fibrils.

ECL Assay of Trypsin and Chymotrypsin Activity Using Ru(bpy)$_3^{2+}$-Labeled Peptide Fibrils A Ru(bpy)$_3^{2+}$-labeled tetrapeptide (NH$_2$-Gly-Lys-Phe-Gly-Ru(bpy)$_3^{2+}$) was conjugated to carboxylated fibrils as described in Example 1. The Ru(bpy)$_3^{2+}$-labeled peptide fibrils (RPF) were used to detect the activity of the hydrolytic enzymes trypsin and chymotrypsin. In brief, the RPF were added to an aqueous solution containing either or both of the enzymes. Because the peptide was designed to contain specific cleavage sites for both trypsin and chymotrypsin (FIG. 3), and because fibrils are a solid, the action of the enzymes would liberate either Phe-Gly-Ru(bpy)$_3^{2+}$ (trypsin) or Gly-Ru(bpy)$_3^{2+}$ (chymotrypsin) into the solution. Following a suitable incubation time for the enzymes to cleave the solid phase peptide, the aqueous solution was separated from the fibrils by standard means such as centrifugation, filtration, or removal of the fibrils with a magnet. The liberated Phe-Gly-Ru(bpy)$_3^{2+}$ or Gly-Ru(bpy)$_3^{2+}$ in the aqueous solution is then detected by ECL.

Although assays of trypsin and chymotrypsin are shown here, other hydrolytic enzymes could be detected using fibrils conjugated to the appropriate Ru(bpy)$_3^{2+}$-labeled enzyme substrate. Such enzymes (and modified fibrils) include: nucleases (using fibrils conjugated to Ru(bpy)$_3^{2+}$-labeled RNA, single stranded DNA, or double stranded DNA), glycosidases (using fibrils conjugated to Ru(bpy)$_3^{2+}$-labeled sugars, oligosaccharides, or polysaccharides), or lipases (using fibrils conjugated to Ru(bpy)$_3^{2+}$-labeled lipids).

EXAMPLE 3

ECL Detection of Trypsin Using Fibrils

To 2.97 ml suspensions of RPF (Fibrils-Gly-LysPhe-Gly-Ru(bpy)$_3^{2+}$) (2.2 mg/mL) in standard ECL Assay Buffer (IGEN, Inc., Gaithersburg, Md.) was added either 30 μL of 58.9 μM trypsin (final concentration=0.59 μM) in 1 mM HCl or 30 μl of 1 mM HCl. The two suspensions were then rotated at room temperature. Periodically, the rotation was stopped, the suspension was quickly centrifuged, and the ECL of the aqueous supernatant was measured. The ECL results after 30 minutes of incubation showed that the ECL ratios of the samples (ECL with trypsin/ECL without trypsin) was 1.29. After 44 hours, the ECL ratio was 2.05. These results demonstrated that trypsin could be detected by its ability to hydrolytically liberate an electrochemiluminescent ruthenium label from fibrils.

EXAMPLE 4

ECL Detection of Chymotrypsin Using Fibrils

To 2.97 ml suspensions of RPF (Fibrils-Gly-LysPhe-Gly-Ru(bpy)$_3^{2+}$) (0.15 mg/mL) in standard ECL Assay Buffer (IGEN, Inc., Gaithersburg, Md.) was added either 30 μl of 34.2 μM chymotrypsin (final concentration=0.34 μM) in 1 mM HCl or 30 μl of 1 mM HCl. The suspensions were rotated at room temperature. Periodically, the rotation was stopped, the suspension was quickly centrifuged, and the ECL of the aqueous supernatant was measured. The ECL results showed that initially (time=0) the ECL ratio of the samples (ECL with chymotrypsin/ECL without chymotrypsin) was 1.06. After 30 minutes of incubation, the ratio rose to 1.25, and after 23 hours of incubation, the ratio rose to 1.85. These data show that chymotrypsin activity could be detected by the ability of the enzyme to liberate an electrochemiluminescent label, Ru(bpy)$_3^{2+}$, from a fibril solid support.

EXAMPLE 5

Covalent Attachment of Proteins to Fibrils Via NHS Ester

To demonstrate that protein can be covalently linked to fibrils via NHS ester, streptavidin, avidin and trypsin were attached to fibrils as follows.

0.5 mg of NHS-ester fibrils were washed with 5 mM sodium phosphate buffer (pH=7.1) and the supernatant was discarded. 200 μl streptavidin solution (1.5 mg in the same buffer) was added to the fibrils and the mixture was rotated at room temperature for 5.5 hours. The fibrils were then washed with 1 ml of the following buffers in sequence: 5 mM sodium phosphate (pH=7.1), PBS (0.1M sodium phosphate, 0.15M NaCl, pH=7.4), ORIGEN assay buffer (IGEN, Inc., Gaithersburg, Md.) and PBS. The streptavidin fibrils were stored in PBS buffer for further use.

2.25 mg NHS-ester fibrils were sonicated in 500 μl of 5 mM sodium phosphate buffer (pH=7.1) for 40 minutes and the supernatant was discarded. The fibrils were suspended in 500 μl of 5 mM sodium phosphate buffer (pH=7.1) and 300 μl of avidin solution made in the same buffer containing 2 mg avidin (Sigma, A-9390) was added. The mixture was rotated at room temperature for two hours, stored at 4° C. overnight and rotated at room temperature for another hour. The fibrils were washed with 1 ml of 5 mM sodium phosphate buffer (pH=7.1) four times and PBS buffer twice. The avidin fibrils were suspended in 200 μl PBS buffer for storage.

Trypsin fibrils were prepared by mixing 1.1 mg NHS-ester fibrils (treated as in avidin fibrils) and 200 μl of 1.06 mM trypsin solution made in 5 mM sodium phosphate buffer (pH=7.1) and rotating at room temperature for 6.5 hours.

The trypsin fibrils were then washed by 1 ml of 5 mM sodium phosphate buffer (pH=7.1) three times and suspended in 400 µl of the same buffer for storage.

EXAMPLE 6

DNA Probe Assay Using ECL Analyzer

To eliminate non-specific binding of analyte on streptavidin (or avidin) bound fibrils in ECL assay, these fibrils were blocked by 4 mg/ml BSA (bovine serum albumin) solution for 6 hours at room temperature and overnight at 4° C.

Figure 4:
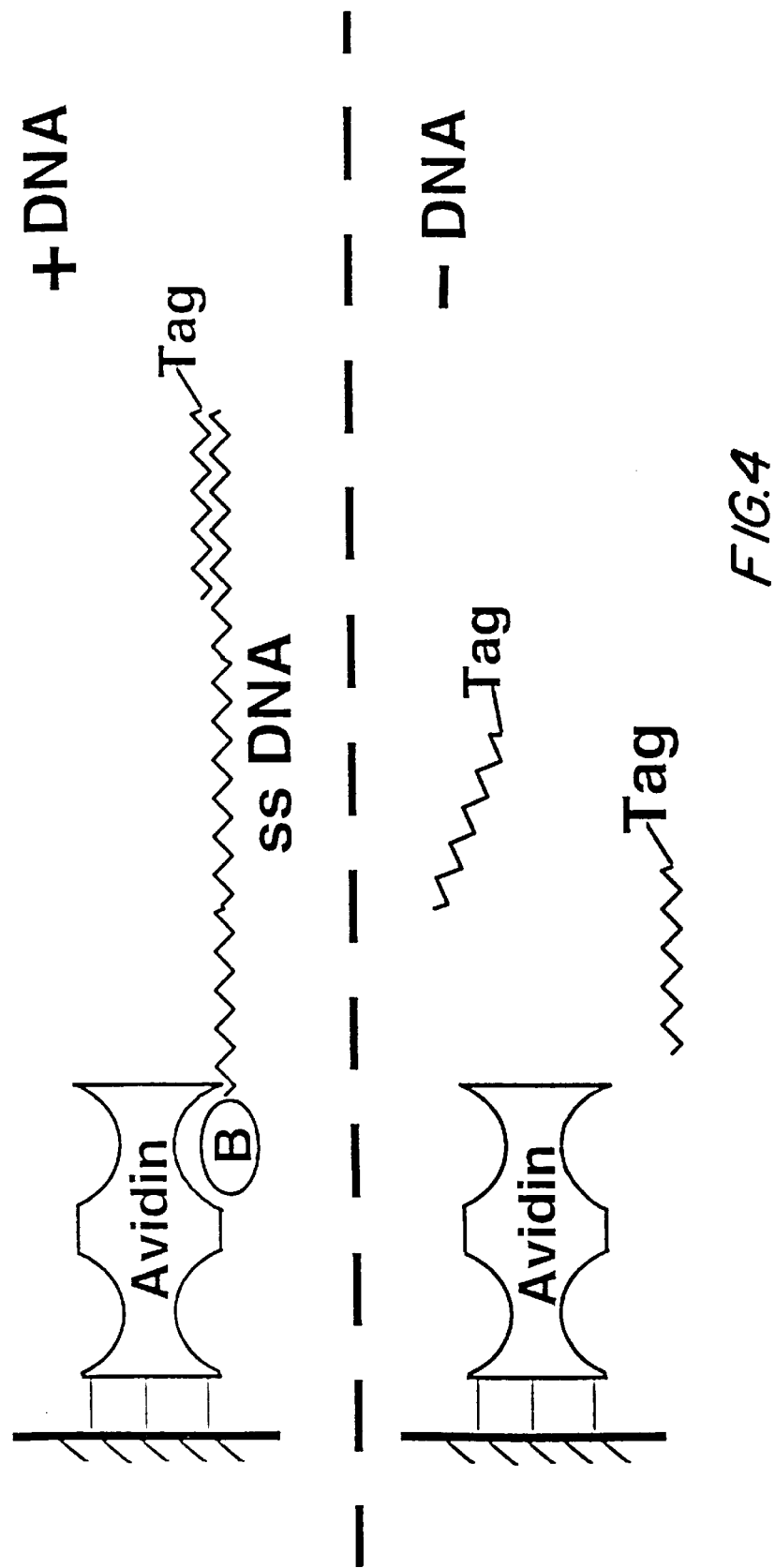
FIG. 4 is a schematic representation of a DNA probe assay using avidin-fibrils.

The DNA probe assay is depicted in FIG. 4. The experiment was started with washing 115 µg of BSA blocked avidin-fibrils and streptavidin fibrils (from Example 5) twice with 5 mM sodium phosphate buffer (pH=7.1). Each fibril was aliquoted into two tubes with ~57 µg in 100 µl of the same buffer. One tube of (strept)avidin fibrils was mixed with 4 µl of 4 nM biotinylated DNA (70 nucleotides) that was bound to a ruthenium tag labeled oligomer. The other tube was added with 4 µl of ruthenium tag labeled oligomer (same concentration as in the biotinylated DNA sample) only for a control assay. The reaction mixtures were incubated at room temperature for 15 minutes and washed seven times with 300 µl of ORIGEN assay buffer (IGEN, Inc., Gaithersburg, Md.). The fibrils were then suspended in 600 µl ORIGEN assay buffer and aliquoted to two tubes for duplicate ECL counting, using gravity capture of the fibrils. The result of the ECL assay were summarized as follows:

| sample | ECL count |
| --- | --- |
| avidin fibrils (control) | 161 |
| avidin fibrils (DNA probe) | 2212 |
| streptavidin fibrils (control) | 885 |
| streptavidin fibrils (DNA probe) | 4248 |

The same assay of avidin fibrils was also carried out using magnetic capture of the fibrils. The experimental procedure was the same as above except for no washing after DNA binding to fibrils. The sample was washed in the ECL analyzer with programmed steps. The ECL count was 3835 for avidin fibril DNA probe verses 205 for the control.

Avidin adsorbed on C8-fibrils were also examined by the DNA probe assay using magnetic capture of the fibrils as described above. The ECL count was 15,792 for avidin fibril DNA probe verses 205 for the control.

EXAMPLE 7

Covalent Immobilization of Antibodies on Carbon Nanotubes

The object of the example is to immobilize antibodies on the surfaces of carbon nanotubes. Such antibody-modified nanotubes can be used in various applications including immunoassay detection of specific analytes and biospecific affinity separations. Immunoassays could be carried out using antibody-modified nanotubes as a solid support. Use of a solid support allows for washing steps if the solid support is either fixed, or otherwise separated from the solution phase (by for instance, filtration, centrifugation, or magnetism). Use of wash steps would permit the use of antibody-modified nanotubes in many types of electrochemiluminescence-based immunoassays. The antibody-modified nanotubes could be used as replacements of the conventionally-used magnetic beads, or as a suspendible support capable of capture by filtration, or as a permanently-fixed support ion a disposable cartridge.

Fibril-Antibody coupling Between Primary Amine and Carboxyl Groups

Formation of NHS Ester Fibrils

A suspension of 148.4 mg of carbon fibrils (Hyperion Catalysis International, Cambridge, Mass.) in a $CH_2Cl_2$/dioxane mixture was mixed with 239 mg of N-hydroxysuccinimide (NHS) and 399 mg of EDC and the reaction was allowed to proceed for 4 hours. The yield of the resulting NHS ester-modified fibrils (NHS-Fibrils) was 214.7 mg.

Formation of Antibody-Modified Fibrils

NHS ester fibrils (84.5 mg) were pre-treated with 1.0 mL coupling buffer (0.2M $NaHCO_3$, pH 8.1), then suspended in another 1.0 mL of coupling buffer (0.1M sodium phosphate, 0.5M NaCl, pH 7.5). Monoclonal antibody (anti-glucose oxidase) (1.5 mg in 2.0 mL of coupling buffer) was added to the fibrils and the suspension was rotated for 1 hour to allow the NHS fibrils to react with the antibody (primarily with lysine sidechains of the antibody). The resulting fibrils were filtered and repeatedly washed with coupling buffer.

Binding of Glucose Oxidase to Antibody-Modified Fibrils

Non-antibody coated sites on antibody-modified fibrils were blocked by rotation for 10 minutes with 1% BSA dissolved in phosphate-buffered saline solution, pH 6.0. Glucose oxidase was dissolved in the BSA solution and this solution was mixed with the fibrils for 1.5 hours. Finally, the fibrils were washed with neutral pH phosphate buffer until no protein was observed to elute by spectrophotometrically monitoring the effluents at 280 nm.

Detection of Antibody on Antibody-Modified Fibrils

Functional antibody molecules on the fibrils were quantitated by the catalytic activity of bound antigen, glucose oxidase. Glucose oxidase activity was spectrophotometrically-determined by adding a sample of the enzyme (either free enzyme or enzyme specifically bound to antibody-modified fibrils) to a cuvette containing 0.1M sodium phosphate (pH 6.0), 20 µM glucose, 183 nM horseradish peroxidase, and 30 µM 2,2'-azino-bis(3-ethylbenzthiazoline-6-sulfonic acid (ABTS). The activity of glucose oxidase was measured by spectrophotometrically determining the rate of absorbance increase at 414 nm at 25° C. (formation of green color). Quantitation of the bound enzyme indicated that there was 1.52 µmoles of functional antibody per gram of fibrils.

Fibril-Antibody Coupling Between Primary Amine and Carbohydrate Groups

Formation of Amino Fibrils

A suspension of NHS-fibrils (214.7 mg) in freshly prepared 0.2M $NaHCO_3$, pH 8.1 was mixed with 1,2-diaminoethane (100 µL) at room temperature. The suspension was stirred for approximately 5 hours. The mixture was then suction filtered in a Buchner funnel and washed with water (3×10 mL) and methanol (3×10 mL) and dried in vacuo overnight. The yield of amino fibrils was 144 mg. Ninhydrin testing demonstrated that diaminoethane (non-conjugated) was still absorbed to the fibrils. Fibrils were resuspended in water and sonicated for 90 minutes. Ninhydrin testing indicated that the fibrils were sufficiently free of non-covalently bound amine.

Formation of Antibody-Modified Fibrils

A NAP-5 column was equilibrated with 100 mM acetate, pH 5.5 and monoclonal antibody (anti-glucose oxidase, 1.5 mg in 300 µL buffer) was added and eluted with buffer (1 mL). This solution was allowed to react with 50 µL of 20 mM NaIO$_4$ (final NaIO$_4$ concentration of 1 mM) at room temperature for 2 hours. The reaction was terminated by addition to a pre-equilibrated NAP-10 (0.15M KH$_2$PO$_4$, pH 6.0) and eluted with the same buffer. The eluent was collected in a 10-mL tube containing amino fibrils and the suspension was allowed to react for 2–3 hours. The fibrils were then washed with reaction buffer and stored in 5 mL KH$_2$PO$_4$, pH 5.5.

Detection of Antibody on Antibody-Modified Fibrils

Functional antibody molecules on the fibrils were quantitated by the catalytic activity of bound antigen, glucose oxidase as described above. Quantitation of the bound enzyme indicated that there was 0.36 μmoles functional antibody per gram of fibrils.

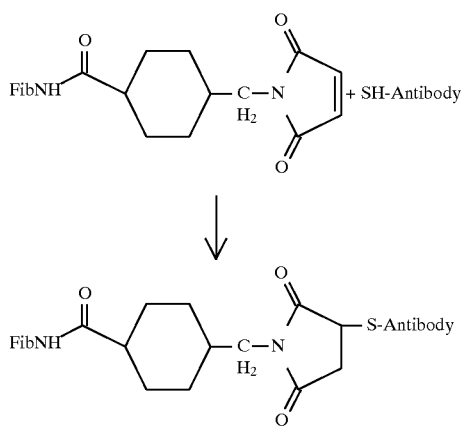

Reduction of Mouse Monoclonal Antibody

To an antibody solution (24.7 mg, in 2.9 ml) was added dithiothreitol (DTT, 25 mg, 0.16 mmol) and the mixture was incubated for 1 hour at room temperature. The reduced antibody was purified using a PD-10 disposable gel filtration column (Pharmacia).

Covalent Coupling of Antibody and Maleimide Fibrils

Maleimide fibrils (0.18 mg) and plain fibrils (0.15 mg) were sonicated for 15 minutes at room temperature and incubated for 30 minutes at 40° C. The fibrils were then centrifuged and the supernatant was removed. Fibrils were then incubated with reduced antibody (12.4 mg) in sodium phosphate buffer (0.1M, pH 7.2, 1.1 ml) for 4 hours at room temperature.

Quantitation of Antibody on Antibody Fibrils Using Horseradish Peroxidase (HRP)-Labeled Goat Anti-Mouse Antibody Mouse antibody fibrils were pre-incubated with 0.1% PEG in sodium phosphate buffer (0.1M, pH 7.5, 1 ml) for 30 minutes at 40° C. They were then centrifuged and the supernatant was removed. Mouse antibody fibrils were incubated with HRP-labeled goat anti-mouse antibody (0.01mg) in sodium phosphate buffer (0.1M, pH 7,5, 500 ml) containing 0.1% PEG for 2 hours at room temperature. The fibrils were then washed five times with 0.1% PEG in sodium phosphate buffer (0.1M, pH 7.5, 1 ml). The amount of bound HRP was determined by spectrophotometrically measuring the catalytic activity of the bound enzyme. The enzyme reaction is shown below:

$H_2O_2$ + ABTS $\xrightarrow{HRP}$ $2H_2O$ + Product (414 nm)

The results showed that the density of the mouse antibody on the fibrils was 1.84 mg antibody per gram of fibrils and the density of the mouse antibody on plain (control) fibrils was 0.48 mg antibody per gram of fibrils (the extent of nonspecific binding was about 26%).

EXAMPLE 8

Preparation of Bifunctional Fibrils by Addition of Lysine

Figure 5:
FIG. 5 is a schematic representation of a reaction scheme for the preparation of bifunctional fibrils by the addition of $N_\epsilon$-(tert-butoxycarbonyl)-L-lysine.

Synthesis of N$_\alpha$-CBZ-L-lysine benzyl ester:

The reaction sequence is shown in FIG. 5. N$_\epsilon$-(tert-butoxycarbonyl)-L-lysine (2 g, 8.12 mmol) was dissolved in methanol (40 ml) and water (40 ml), and the pH was adjusted to 8 with triethylamine. A solution of N-(benzyloxycarbonyl-oxy)succinimide in dioxane (2.4 g, 9.7 mmol in 20 ml) was added to the above mixture and the pH was maintained at 8–9 with triethylamine. The reaction mixture was stirred overnight. The solvent was removed by rotary evaporation to obtain crude N$_\alpha$-CBZ-N$_\epsilon$-(tert-butoxycarbonyl)-L-lysine. N$_\alpha$-CBZ-N$_\epsilon$-(tert-butoxycarbonyl)-L-lysine was treated with 0.2M calcium carbonate (4 ml) and the aqueous layer was removed to obtain a white solid. The solid was resuspended in N,N-dimethylformamide(40 ml) and benzyl bromide (1.16 ml). The reaction mixture was stirred overnight at room temperature. The reaction mixture was worked up with ethyl acetate and water, and the organic layer was dried over magnesium sulphate. The solvent was removed to obtain crude N$_\alpha$-CBZ-N$_\epsilon$-(tert-butoxycarbonyl)-L-lysine benzyl ester which was purified by silica gel chromatography using 25% hexane in ethyl acetate as a solvent. To N$_\alpha$-CBZ-N$_\epsilon$-(tert-butoxycarbonyl)-L-lysine benzyl ester (1 g, 2.2 mmol) in methylene chloride (10 ml) was added trifloroacetic acid at 0° C. The reaction mixture was stirred for 10 minutes at 0° C., then stirred for further 2.5 hr at room temperature. The solvent was removed and the crude product was obtained. Pure N$_\alpha$-CBZ-L-lysine benzyl ester was obtained by silica gel chromatography.

Synthesis of N$_\alpha$-CBZ-L-lysine benzyl ester fibrils:

To a suspension of carboxyl fibrils (300 mg) in methylene chloride (18 ml) was added a solution of N$_\alpha$-CBZ-L-lysine benzyl ester (148 mg, 0.32 mmol in 20 ml methylene chloride and 176 μl triethylamine). HOBT (43.3 mg, 0.32 mmol) and EDC (61.3 mg, 0.32 mmol) were then added. The reaction mixture was stirred overnight at room temperature to obtain the crude product. The product fibrils were extensively washed with methanol, methylene chloride, and water, then dried under vacuum.

Synthesis of bifunctional fibrils Fib-Lys(COOH)NH$_2$:

To N$_\alpha$-CBZ-L-lysine benzyl ester fibrils (113 mg) in methanol (4 ml) was added sodium hydroxide (1 N, 4 ml) and the reaction mixture was stirred overnight. The product N$_\alpha$-CBZ-L-lysine fibrils was extensively washed with water and methanol and the fibrils were dried under vacuum. To a suspension of N$_\alpha$-CBZ-L-lysine fibrils (50 mg) in acetonitrile (4 ml) was added trimethyl silyl iodide (1 ml). The mixture was stirred for 3 hours at 40° C. The final bifunctional fibrils were extensively washed with water, methanol, 0.5N sodium hydroxide, acetonitrile and methylene chloride. Amino acid analysis showed 0.3 μmols lysine per gram of fibrils.

Hydroxyl and carboxyl (or amino) bifunctional fibrils can be made by a similar method to that described here by using serine, threonine, or tyrosine. Thiolated and carboxyl (or amino) bifunctional fibrils can be made using cysteine. Carboxyl and amino bifunctional fibrils can be made using aspartic or glutamic acid.

EXAMPLE 9

Carbon Nanotube as ECL-Based Biosensors

Figure 6:
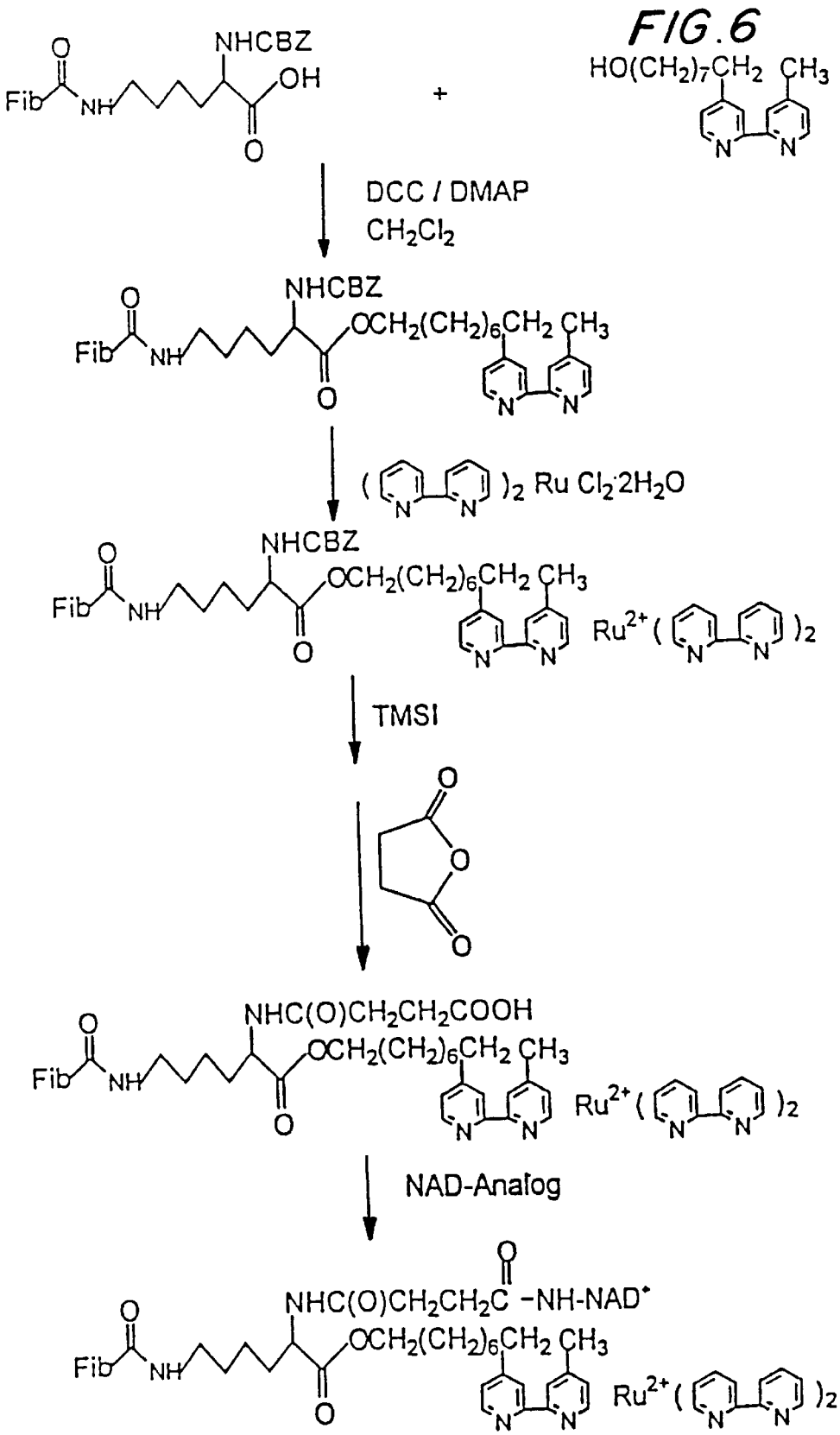
FIG. 6 is a schematic representation of a reaction scheme for synthesizing the ECL-based, bifunctional biosensor fibril.

To a suspension of bifunctional fibril (113 mg) in methylene chloride (8 ml) were added 4-dimethylaminopyridine (DMAP, 19.5 mg, 0.16 mmol) and 1,3 dicyclohexylcarbodiimide (DCC, 33 mg, 0.16 mmol) (FIG. 6). The mixture was stirred for 5 minutes, then 4-methyl-4'-(8-hydroxyoctyl) 2,2'-bipyridine (47 mg, 0.16 mmol) was added. The reaction mixture was stirred overnight at room temperature. The resulting product fibrils were extensively washed sequentially with DMF, 50% dioxane in water, methanol, and water. The fibrils were suspended in a mixture of ethanol (4 ml) and water (4 ml) and cis-dichlorobis (2,2'-bipyridine) ruthenium (II) dihydrate (45.2 mg, 0.087 mmol) was added. The mixture was refluxed for 5.5 hours at 110° C. The ruthenium complex-modified fibrils were extensively washed with water, standard ECL assay buffer (IGEN, Inc., Gaithersburg, Md.), toluene, 50% dioxane in water, then sequentially refluxed in acetonitrile, ethylene glycol and methanol. The ruthenium complex-modified fibrils were reacted with TMSI (4 ml) in acetonitrile (4 ml) for 4 hours at 40° C. to deprotect the CBZ group, then washed with methanol, water, and sodium hydroxide (1N). The final produce was dried under vacuum. The fibrils were then suspended in methylene chloride (5 ml) and triethylamine (5 drops) was added. To the suspension was added succinic anhydride (40 mg). The reaction mixture was stirred overnight at room temperature and the product was washed with methylene chloride, methanol, and water, then dried under vacuum. The carboxylic acid/ruthenium complex-modified fibrils were resuspended in dioxane (5 ml), then N-hydroxysuccinimide (100 mg) and EDC (167 mg) were added. The reaction mixture was stirred for 4 hours at room temperature. The resulting NHS ester/ruthenium complex-modified fibrils were washed with dioxane and methanol. The NHS ester/ruthenium complex-modified fibrils were resuspended in dioxane (2 ml) and a solution of NAD analog in sodium bicarbonate (75 ml in 2 ml of 0.2M pH 8.6 NaHCO$_3$) was added. The reaction mixture was stirred overnight at room temperature. The fibrils were then extensively washed with water, sodium bicarbonate (0.2M), and methanol, then dried under the vacuum to obtain the biosensor fibrils.

EXAMPLE 10

Use of Carbon Nanotubes as ECL-Based Biosensors

Figure 7:
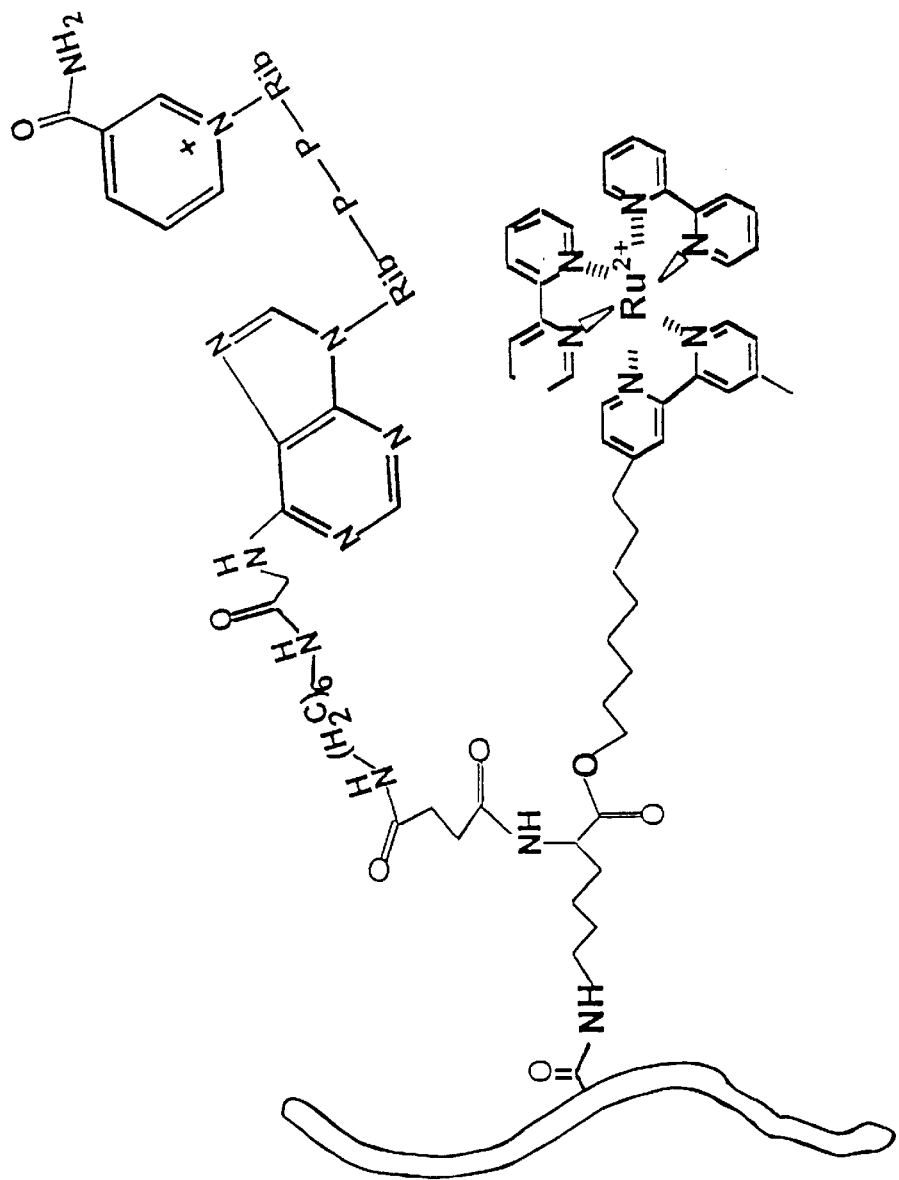
FIG. 7 is a schematic representation of bifunctional ECL-based biosensor fibril.

An ECL-based biosensor was prepared by chemical modification of fibrils. The modified fibrils were prepared using NH$_2$/COOH bifunctional fibrils (Example 8). To one functional group (NH$_2$) was added an NAD$^+$ analog and to the other functional group (COOH) was added a derivative of Ru(bpy)$_3^{2+}$. The structure of the biosensor fibrils is shown in FIG. 7.

Figure 8:
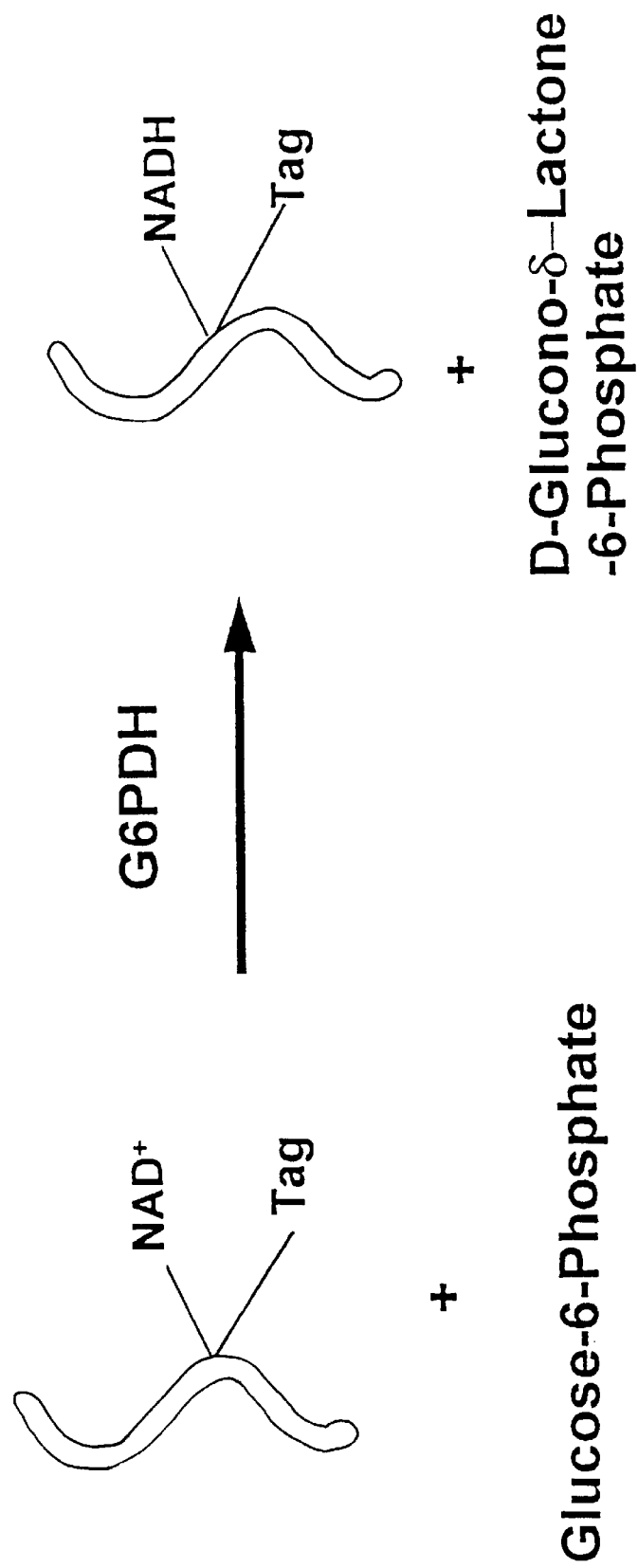
FIG. 8 is a schematic representation of the reaction catalyzed by D-glucose-6-phosphate dehydrogenase.

The biosensor was designed to facilitate detection of dehydrogenase enzymes that accept NAD(P)$^+$/NAD(P)H as a cofactor and substrates of dehydrogenase enzymes that accept NAD(P)$^+$/NAD(P)H as a cofactor. It is known (E. Jameison et al., Analytical Chemistry, in press) that NAD (P)$^+$ and NAD(P)H have dramatically different abilities to promote Ru(bpy)$_3^{2+}$ ECL. Thus, the activity of a dehydrogenase can be detected by its ability to reduce/oxidize NAD(P)$^+$/NAD(P)H, which is observable by differences in the abilities of NAD(P)$^+$ and NAD(P)H to cause Ru(bpy)$_3^{2+}$ electrochemiluminescence (FIG. 8). Similarly, because the action of dehydrogenases on their substrates is stoichiometrically accompanied by conversion of NAD(P)$^+$ to NAD (P)H or NAD(P)H to NAD(P)$^+$, the presence of their substrates can also be detected by electrochemiluminescence.

To use the fibril supported ECL-based biosensor, the biosensor is mixed with an aqueous solution containing a dehydrogenase and an unknown quantity of the dehydrogenase's substrate (the substrate is the analyte) or an aqueous solution containing a dehydrogenase substrate and an unknown quantity of dehydrogenase (the dehydrogenase is the analyte). After a suitable incubation time to allow the enzyme reaction to proceed and the NAD(P)$^+$ or NAD(P)H immobilized on the fibrils to be reduced or oxidized, the fibrils are drawn into an ECL instrument and the ECL of the fibrils is measured. ECL measurement is carried out in a buffer that does not contain appreciable concentrations of tripropylamine (because NAD(P)$^+$/NAD(P)H are tripropylamine replacements in this invention).

The attractive features of this ECL-based biosensor are: the close proximity of NAD(P)$^+$/NAD(P)H and Ru(bpy)$_3^{2+}$ on the same bifunctional group on the fibrils which enhances the efficiency of electron transfer in the electrochemical ECL mechanism (intramolecular electron transfer is more efficient than intermolecular electron transfer); the ECL active reagents, NAD(P)$^+$/NAD(P)H and Ru(bpy)$_3^{2+}$ are both supported on fibrils which can be magnetically held on the ECL instrument electrode which will increase light emission; fibrils have extremely high surface areas which permit immobilization of a high density (per weight) of NAD(P)$^+$/NAD(P)H and Ru(bpy)$_3^{2+}$ which will allow more light to be emitted; the biosensor is versatile in that it can detect many different analytes (any dehydrogenase that accepts NAD(P)$^+$ or NAD(P)H as a cofactor, or the substrates of these enzymes).

EXAMPLE 11

Figure 9:
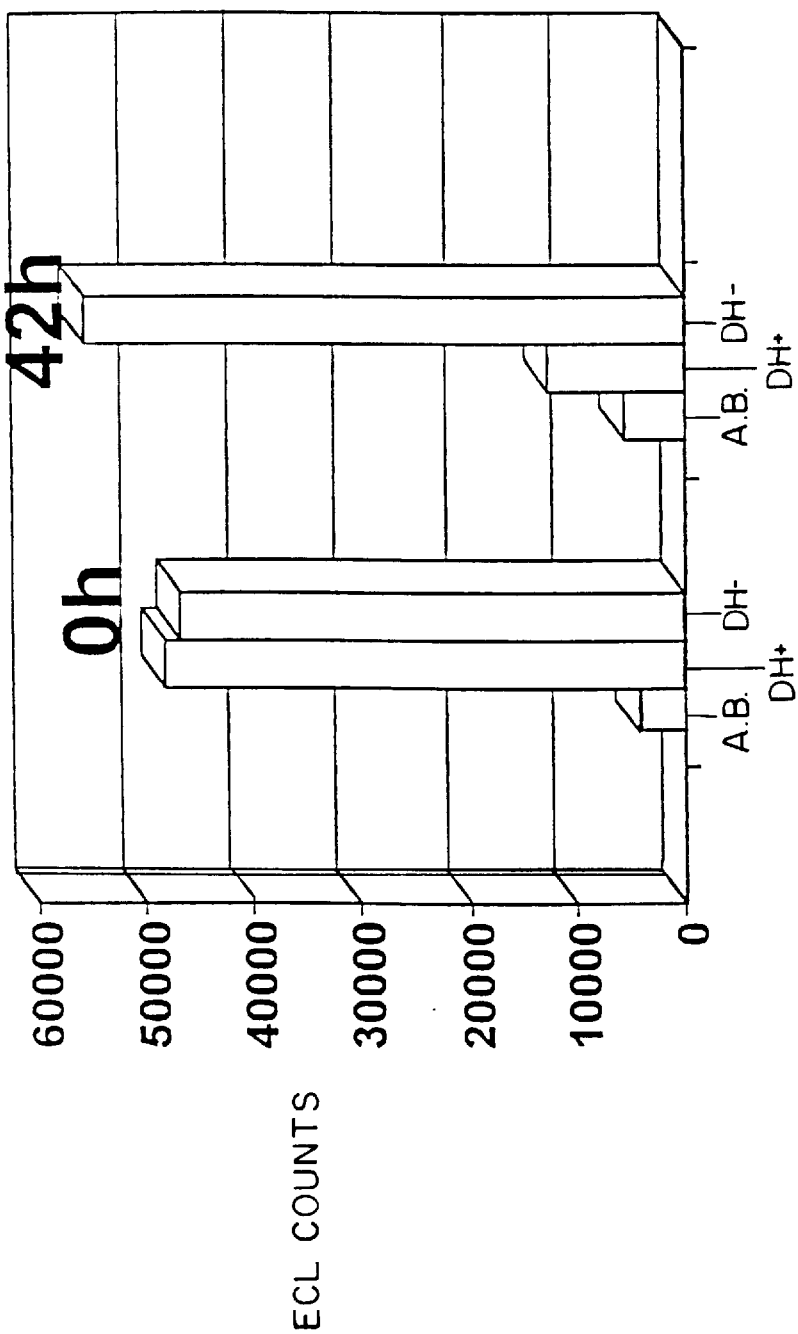
FIG. 9 is a graph showing the ECL detection of glucose-6-phosphate dehydrogenase using a fibril-supported ECL-based biosensor.

Detection of glucose-6-phosphate dehydrogenase (G6PDH) using a fibril supported ECL-based biosensor Fibrils modified with both an NAD$^+$ analog and a Ru(bpy)$_3^{2+}$ analog being covalently attached to a bifunctional adduct (ECL biosensor fibrils) were used to detect the enzyme glucose-6-phosphate dehydrogenase. ECL biosensor fibrils (860 μg/mL) were mixed with a neutral pH buffered solution containing approximately 50 μM glucose-6-phosphate. Into one tube was added G6PDH to a concentration of 3.6 μM. Into a second control tube was added deionized water. Immediately the ECL of the fibrils was measured. FIG. 9 shows that at time zero the ECL of the fibrils with (DH+) and without (DH−) G6PDH was a similar level. The background ECL resulting from the assay buffer (no fibrils) is also shown (A.B.). After 42 hours of incubation (rotation at room temperature) more fibrils were withdrawn and the ECL was measured again. As shown in FIG. 9, the ECL of assay buffer (A.B.) and fibrils in the absence of G6PDH (DH−) was similar to the ECL seen at time zero. However, the ECL of the sample containing G6PDH (DH+) was substantially lower than at time zero. The results indicate that G6PDH activity could be detected using fibril supported ECL biosensors. Separate work with the particular NAD$^+$ analog used here (non-immobilized) and Ru(bpy)$_3^{2+}$ (non-immobilized) in the absence of fibrils confirmed that the reduced (NADH) version of the NAD$^+$ analog is less efficient than the oxidized (NAD$^+$) version at causing Ru(bpy)$_3^{2+}$ to be electrochemiluminescent.

EXAMPLE 12

Use of Carbon Nanotubes as a Support for an ECL-Based Enzyme Biosensor

Figure 10:
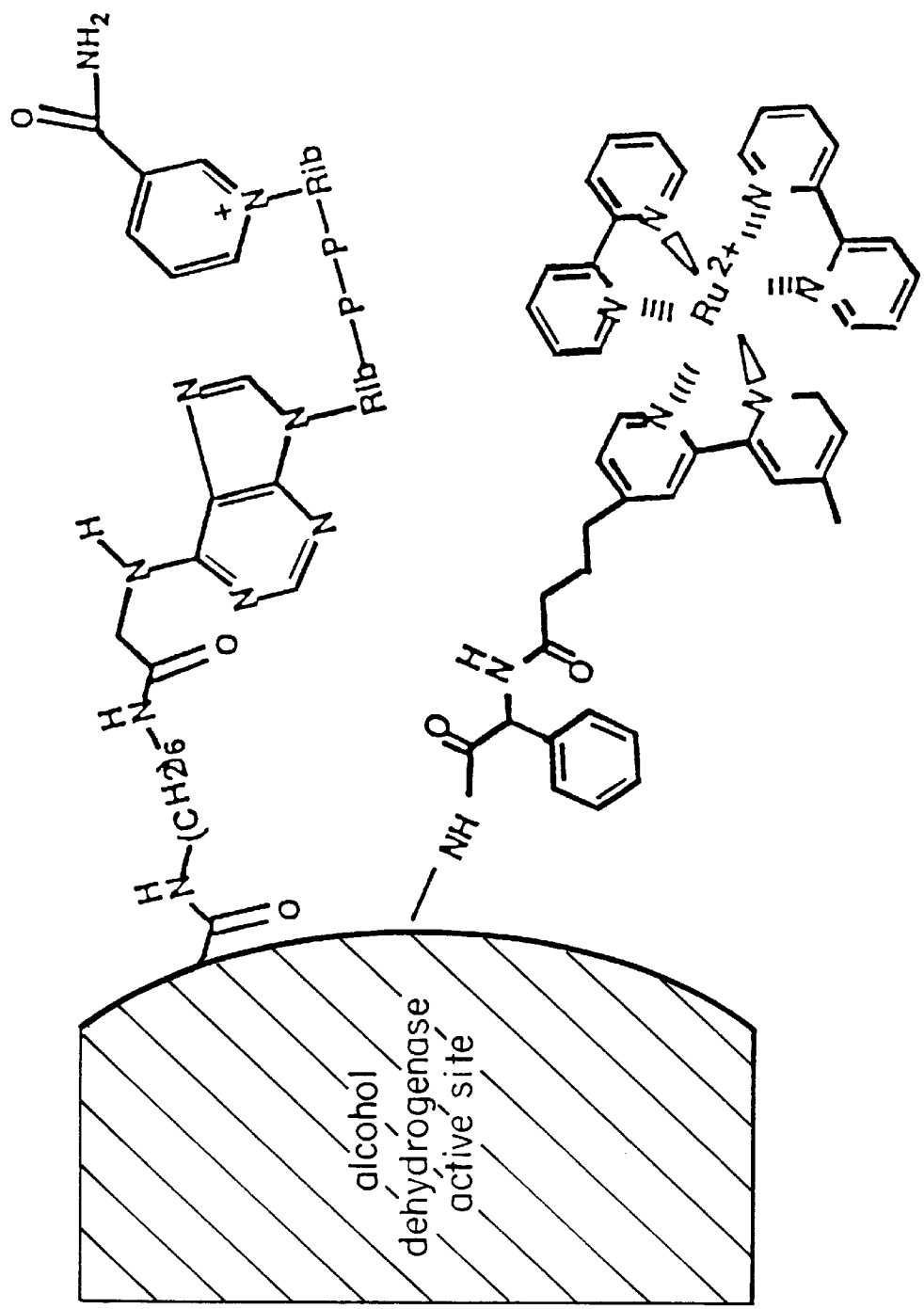
FIG. 10 is a schematic representation of an alcohol dehydrogenase (ADH) based ECL biosensor.

An enzyme biosensor was prepared containing a dehydrogenase enzyme to which has been conjugated both an analog of a nicotinamide adenine dinucleotide (NAD$^+$) enzyme cofactor and an analog of ruthenium (II) trisbipyridine (Ru(bpy)$_3^{2+}$). The NAD$^+$ analog is tethered so that it can bind in the enzyme's cofactor binding site and behave naturally when bound (i.e., it can be reduced by the enzyme by the normal chemical mechanism in the presence of the natural substrate of the enzyme). Moreover, the Ru(bpy)$_3^{2+}$ analog is tethered so that it can come into physical contact with the NAD$^+$ (FIG. 10). In an ECL instrument such as an IGEN Origen® Analyzer (IGEN, Inc., Gaithersburg, Md.), NAD$^+$ and its reduced form, NADH, promote Ru(bpy)$_3^{2+}$ electrochemiluminescence to different extents. Thus, based on the light output, it can be determined whether NAD$^+$, NADH, or some mixture of the two is present in a solution (F. Jameison et al., Analytical Chemistry, in press). Thus, the biosensor uses the differences between the efficiencies of the ECL reactions of Ru(bpy)$_3^+$ to detect the extent of reduction of NAD$^+$ and hence the presence of the enzyme's substrate. As an example, alcohol dehydrogenase catalyzes the reaction shown below; ethanol (reduced)+NAD$^+$ (oxidized)→ acetaldehyde (oxidized)+NADH (reduced). An alcohol dehydrogenase-based ECL biosensor can convert ethanol to acetaldehyde, concomitantly converting NAD$^+$ to NADH. Because the ECL properties of Ru(bpy)$_3^{2+}$ immobilized on the biosensor depend on whether NAD$^+$ or NADH is immobilized, the ECL of the enzyme biosensor can report the presence of ethanol. An attractive feature of the biosensor is that because during the ECL reaction the NADH form of the cofactor is re-oxidized to the NAD$^+$ form, one biosensor molecule can be used repeatedly to detect multiple molecules of analyte.

Figure 11B:
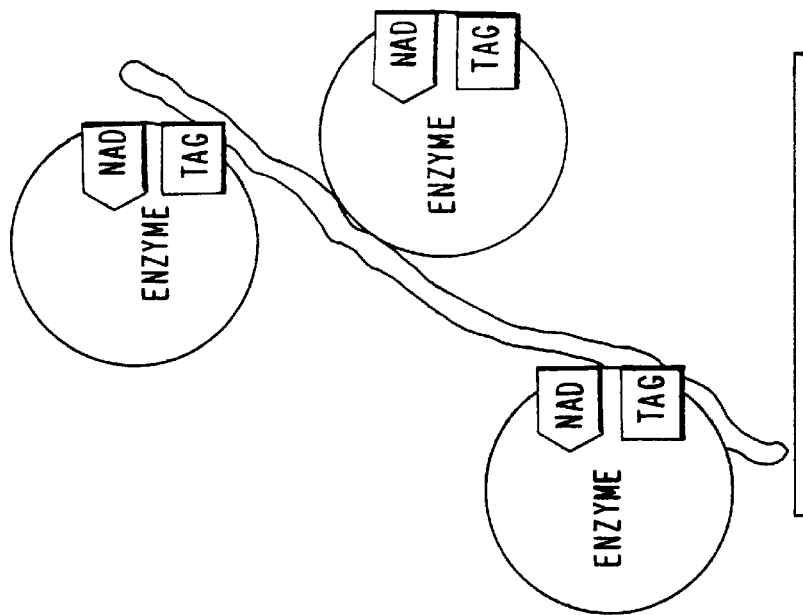
FIG. 11 is a schematic representation of an ADH-based biosensor immobilized on Dynal M450 beads (left) and immobilized on alkyl fibrils (right).
Figure 11A:
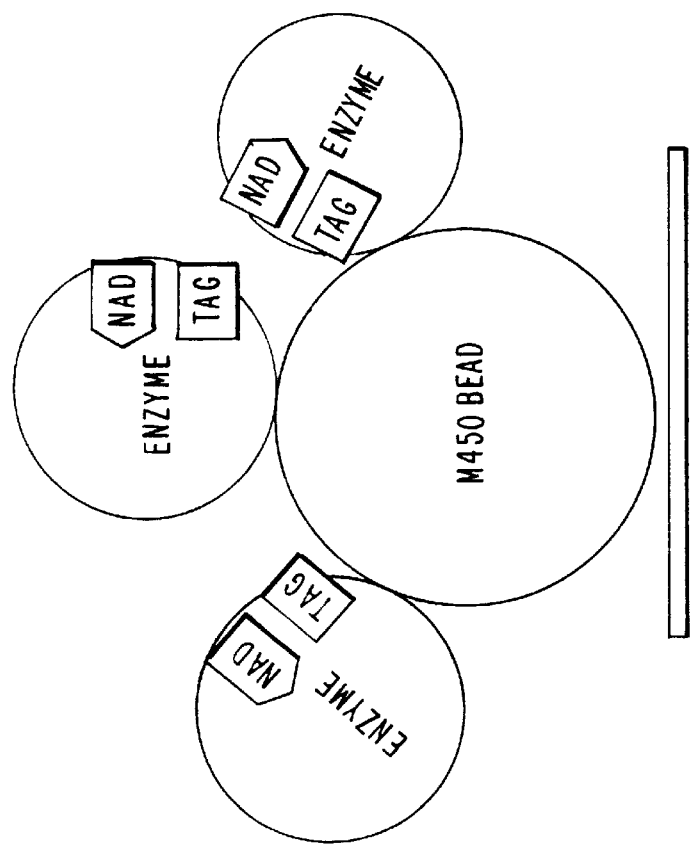

Because the biosensor is based on a soluble enzyme (a dehydrogenase) and the analyte (ethanol for example) is also soluble, it would be beneficial to immobilize the biosensor so that it could be used repetitively to analyze different analyte-containing samples without being washed away with a spent analyte-containing solution. Such immobilization was carried out with an alcohol dehydrogenase (ADH) based ECL biosensor (shown schematically in FIG. 10). FIG. 11 shows immobilization of the ADH-based biosensor on Dynal M450 beads (Lake Success, N.Y.) (left) and immobilization on alkyl fibrils (right). Neither diagram is drawn to scale such that the biosensor molecules are actually much smaller relative to the size of the solid supports. The alkyl fibrils were prepared by the reaction of oxidized fibrils (bearing COOH groups) with 1-aminooctane. In both cases (beads and fibrils) the enzyme biosensor was immobilized by noncovalent adsorption in buffered aqueous solution.

Ethanol was detected using both bead- and fibril-immobilized ECL ADH-based biosensors. The amount of enzyme biosensor adsorbed to beads or fibrils was determined by measuring the amount of remaining (non-absorbed) protein in solution by the UV absorbance at 280 nm (the absorbance at 280 nm indicates the amount of protein in solution). The results showed that 0.308 mg of the ADH biosensor bound per mg of fibrils while 0.015 mg of the ADH biosensor bound per mg of beads. Thus, per unit weight of the solid support, the absorptive capacity of fibrils exceed that of Dynal beads by 20.5 times.

Figure 12B:
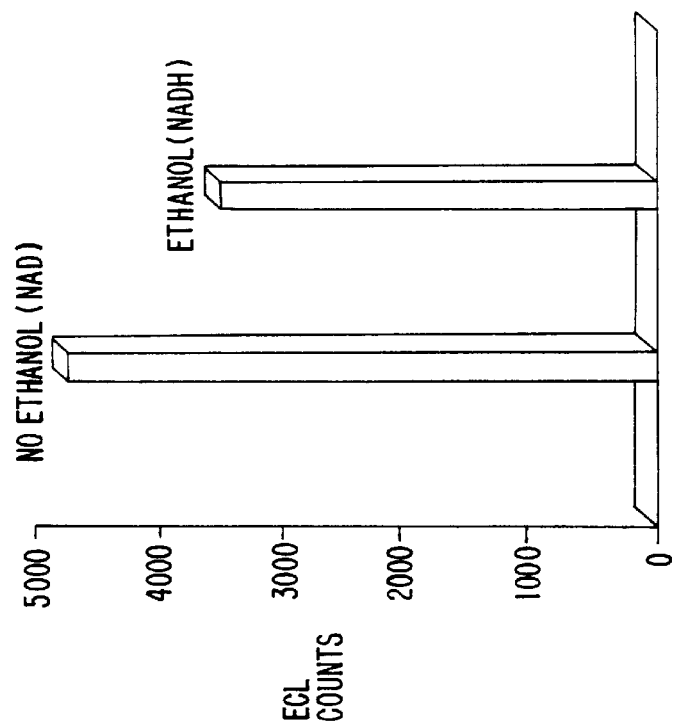
FIG. 12 is a graph showing ECL detection of ethanol using an enzyme biosensor immobilized on beads and fibrils.
Figure 12A:
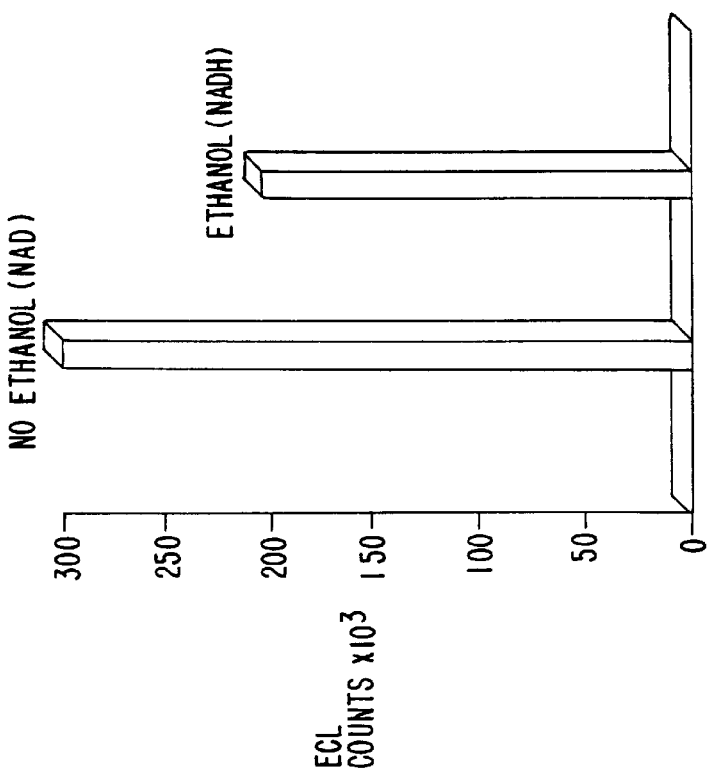

ECL sensing of ethanol was carried out by mixing the ADH biosensor adsorbed beads (0.50–1.25 mg) or fibrils (0.04–0.10 mg) with a solution containing 0.1M sodium phosphate buffer (pH 7.2), 12 mM semicarbizide. Some samples also contained 0.5 mM of the analyte, ethanol. The solid supports coated with the biosensor were drawn into an IGEN Origen® ECL Analyzer (IGEN, Inc., Gaithersburg, Md.) and ECL was measured. Results of one such experiment are shown in FIG. 12. With both beads and fibrils, the ECL signal of the enzyme biosensor decreased in the presence of ethanol. This result is consistent with results obtained in solution studies (using non-immobilized NAD$^+$/NADH and non-immobilized Ru(bpy)$_3^{2+}$) of the effect of the oxidation/reduction state of this NAD$^+$ analog on Ru(bpy)$_3^{2+}$electrochemiluminescence. These results showed that fibrils can be used as a support for enzymes in ECL and in particular as a support for enzyme-based ECL biosensors. It should also be noted that the results seen with fibrils were similar to those seen with Dynal beads even though 20 times less fibrils was used.

EXAMPLE 13

Biotinylated Fibrils and Bifunctional Biotinylated Alkyl Fibrils

It has been found that fibril surfaces can be biotinylated or both alkylated and biotinylated. The fibrils containing such modifications can then bind any streptavidin conjugated substances such as streptavidin beads and streptavidin enzymes.

Fibrils offer great advantages as solid carriers because of their high surface area. Beads, which can be made strongly magnetic, are extremely useful in separation assays. The biotinylated fibrils described herein combine the advantages of both the fibrils and the beads. The biotinylated alkyl fibrils are an extension of the same concept but exhibit the additional protein adsorption property of alkyl fibrils.

The streptavidin- and biotin-coated fibrils can be used in diagnostics and can be used as capture agents for electrochemiluminescence assays.

A novel feature of this invention is the combination of two solid carriers on one fibril to create a bifunctional fibril. Moreover, the disclosed process increases the surface area for beads and magnifies fibril magnetization.

Preparation of Biotinylated Fibrils

Biotinylated fibrils were prepared by mixing 2.4 mg of amino fibrils prepared essentially as described in Preparation O and 9 mg of NHS ester long chain biotin in buffer 0.2M NaHCO$_3$ at a pH of 8.15. The mixture was rotated at room temperature for four hours and washed with the same buffer twice.

Preparation of Biotinylated Alkyl Fibrils

Biotinylated alkyl fibrils were prepared by a two step reaction. First, 4.25 mg of bifunctional fibrils (containing both amino and carboxyl) and 25 mg of NHS ester long chain biotin were mixed. The fibrils were washed and dried under vacuum.

The second reaction was carried out by mixing 4 mg of biotinylated bifunctional fibrils with 11 mg of EDC (1-ethyl-3-(3-dimethylaminopropyl)carbodiimide), 7.5 mg of DMAP (4-dimethylaminopyridine) and 10 µl of NH$_2$(CH$_2$)$_7$CH$_3$ in 0.5 ml of DMF. The mixture was stirred at room temperature overnight. The final biotinylated alkyl fibrils were washed by $CH_2Cl_2$, MeOH, and $dH_2O$.

EXAMPLE 14

Biotinylated Fibrils as a Solid Support in ECL Assays

Biotinylated fibrils can be used in ECL assays involving formats that require streptavidin-biotin or avidin-biotin interactions. Biotinylated fibrils could for example be further derivatized with streptavidin. Biotin covalently linked to fibrils (see Example 13) could form strong non-covalent binding interactions with streptavidin. Because streptavidin is a tetrameric protein with four equivalent binding sites, streptavidin bound to biotinylated fibrils would almost certainly have unoccupied binding sites to which additional biotinylated reagents could bind. Thus, biotinylated fibrils would be converted to streptavidin-coated fibrils.

There are a number of analytical tests that could be performed with such fibril-biotin-streptavidin (FBS) supports. For example, a biotinylated anti-analyte antibody could be captured on the FBS support (either before or after the antibody has complexed to an analyte). Assays using biotinylated anti-analyte antibodies are well established. Such assays include competitive assays where the analyte of interest competes with an introduced $Ru(bpy)_3^{2+}$-labeled analyte for binding to the anti-analyte antibody. Free (unbound) analyte and free (unbound) $Ru(bpy)_3^{2+}$-labeled analyte can be washed from the fibril immobilized antibody. The washing step depends on the fibrils being physically separated from the solution phase by common practices involving centrifugation, filtration, or by attraction to a magnet.

Besides a competition assay, a sandwich type immunoassay could be carried out on FBS supports. Sandwich immunoassays are well known in the field of diagnostics in general and in ECL detection in specific. Such assays involve an analyte being bound simultaneously by two antibodies; a first "primary" antibody which is captured on a solid surface by for example being labeled with biotin, and a "secondary" antibody which is not captured by a solid surface but is labeled with a reporter group, such as $Ru(bpy)_3^{2+}$ in ECL applications. Such a sandwich assay could be carried out using fibrils as a solid capture support whereby the fibrils are captured as described in the previous paragraph. Hence, in such an assay, the fibril would have covalently linked to it biotin, which would be bound to streptavidin, which would in turn be bound to a biotinylated primary antibody, which would be bound to analyte (if present), which would be bound to a $Ru(bpy)_3^{2+}$-labeled secondary antibody.

Similarly, DNA probe assays could be carried out using FBS supports. Biotinylated single stranded DNA can be bound to FBS supports and competitive hybridization can occur between complementary single stranded analyte DNA molecules and complementary $Ru(bpy)_3^{2+}$-labeled oligonucleotides.

Another type of biotinylated fibrils, biotinylated alkylated fibrils, can be used in immunoassays and DNA probe assays. As described in Example 13, bifunctional fibrils can be modified by covalent attachment of biotin to one type of functional group and alkyl chains to the other type of functional group. The resultant alkylated, biotinylated fibrils can be used both in specific association with streptavidin or avidin (via biotin) and also for adsorption of proteins (via the alkyl chains).

Alkyl fibrils could be used in conjuction with other solid supports, such as streptavidin-coated magnetic beads, including Dynal magnetic beads. One advantage of fibrils over such beads is that they have a much higher surface area (per unit weight). Thus, if fibrils could be attached to the outside surface of the magnetic beads, this would dramatically improve the surface area and hence the binding capacity of the beads. It is envisioned that alkylated, biotinylated fibrils could be mixed with streptavidin-coated beads resulting in high affinity streptavidin(bead)-biotin(fibril) interactions and hence fibril-coated beads with an extremely high surface area. Because alkyl fibrils can bind proteins by adsorption, the fibril-coated beads could be further derivatized with adsorbed proteins including streptavidin and antibodies. As described above, streptavidin or antibody coated fibrils can be used in immunoassays and DNA probe assays. Thus, fibril-coated beads could improve the properties of the beads by dramatically increasing their surface area such that fewer beads would be required in a given assay to give the same result.

EXAMPLE 15

Magnetically-Susceptible Carbon Nanotubes

Fibrils may have magnetic properties. The extent to which fibrils can be made magnetic or nonmagnetic is controlled by the amount of catalyst that is in the fibril as a result of the fibril production process. Such processes are disclosed in U.S. Pat. Nos. 4,663,230, 5,165,909 and 5,171,560.

The magnetic property of fibrils was observed after fibrils were functionalized, i.e. alkyl fibrils, protein bound fibrils, etc. The fibrils after certain reactions (e.g., alkylation) migrated notably faster to a magnet than before the reaction. One hypothesis for this phenomena is that some kind of aggregation or salvation may be occurring during the reaction process. However, the true mechanism is presently undetermined.

EXAMPLE 16

Reduction of Non-specific binding of $Ru(Bpy)_3$ with PEG modified Fibrils

Figure 13:
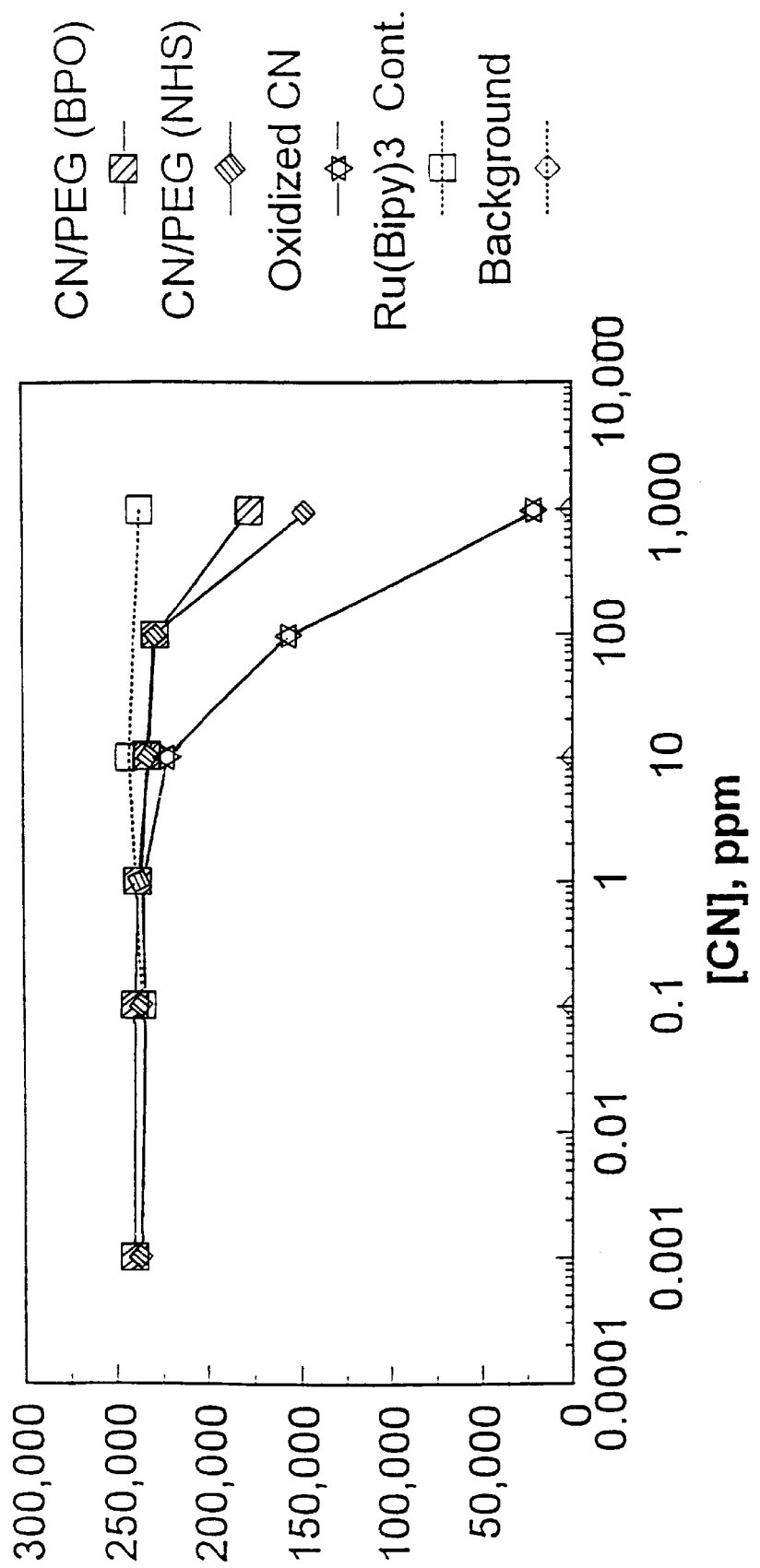
FIG. 13 is a graphical representation of an assay of $Ru(bpy)_3^{2+}$ binding to carboxy fibrils and PEG-modified fibrils prepared by two different methods.

Stock dispersions of chlorate oxidized fibrils, fibrils modified with PEG using benzoyl peroxide and fibrils modified with PEG by NHS ester coupling were prepared at 1.0 mg/ml in 50 mM potassium phosphate buffer, pH 7.0 with sonication. 2 mls of 10-fold serial dilutions of each were placed in each of 5 polypropylene tubes. 50 $\mu$l of a stock solution of $Ru(Bpy)_3$ (approx. 10 $\mu$M) in the same buffer was added to each tube and to 3 buffer blanks. Three bufffer tubes without $Ru(Bpy)_3$ were also prepared. All tubes were mixed on a vortex mixer and allowed to incubate overnight. All tubes were centrifuged to separate the fibrils and 0.1 ml aliquots of the supernatant were transfered to new tubes and diluted with 1.0 mls of Origen® Assay Buffer (IGEN, Inc., Gaithersburg, Md.) and analyzed for $Ru(Bpy)_3$ by ECL using a Magnalyzers (IGEN, Inc., Gaithersburg, Md.). The level of $Ru(Bpy)_3$ remaining in the supernatant was an indirect measure of the amount that had been non-specifically bound to the fibrils (FIG. 13). For both of the PEG modified fibril materials substantially all of the $Ru(Bpy)_3$ remained in the supernatant at fibril levels up to 0.1 mg/ml. There was 20–30% decrease in the $Ru(Bpy)_3$ in the supernatant at 1.0 mgs/ml of these fibrils. In contrast, for the chlorate oxidized fibrils, there was almost no $Ru(Bpy)_3$ remaining in the supernatant at 1.0 mgs/ml and 20–30% decrease in the Ru(Bpy)$_3$ in the supernatant at 0.1 mg/ml of these fibrils without the PEG modification.

REFERENCES

1. Beaucage S L, Caruthers M H. Deoxynucleoside phosphoramidites, a new class of key intermediates for deoxypolynucleotide synthesis. Tetrahedron Lett 1982; 22:1859–62.
2. Shibata D K, Arnheim N, Martin J W. Detection of human papilloma virus in paraffin-embedded tissue using the polymerase chain reaction. J Exp Med 1988; 167:225–30.
3. Yanofsky, C. et al. (1981) Nucleic Acids Res. 24, 6647–6668.
4. Updyke T V, Nicolson G L. Immunoaffinity isolation of membrane antigens with biotinylated monoclonal antibodies and streptavidin-agarose. Methods Enzymol 1986; 121:717–25.
5. Cardullo R A, Agrawal S, Flores C, Zamecnik D C, Wolf D E. Detection of nucleic acid hybridization by nonradiative fluorescence resonance energy transfer. Proc Natl Acad Sci 1988; 85:8790–4.
6. Ngo T T. Procedure for activating polymers with primary and or secondary hydroxyl groups. Makromol Chem Macromol Symp 1988; 17:224–39.
7. Coutlee F, Bobo L, Mayur K, Yoken R H, Viscidi R P. Immunodetection of DNA with biotinylated RNA probes: A study of reactivity of a monoclonal antibody to DNA-RNA hybrids. Anal Biochem 1989; 181:96–105.
8. Casadei J, Powell M J, Kenten J H. Expression and secretion of aequorin as a chimeric antibody using a mammalian expression vector. Proc Natl Acad Sci 1990; 87:2047–51.
9. Molecular cloning, a laboratory manual 2nd Ed Sambrook, J. Cold Spring Harbor Laboratory New York.
10. Heney, G. and Orr, G. A. (1981) Anal Biochem. 114, 92–96.
11. Mullis K B, Faloona F A. Specific synthesis of DNA in vitro via a polymerase-catalyzed chain reaction. Methods Enxymol 1987; 155:335–50.
12. Lyons J, Janssen J W G, Bartram C, Layton M, Mufti G J. Mutation of Ki-ras and N-ras oncogenes in myelodysplastic syndromes. Blood 1988; 71:1707–12.
13. Saiki R K, Gelfand D H, Stoffel S, Scharf S J, Higuchi R, Horn G T, Mullis K B, Erlich H A. Primer-directed enzymatic amplification of DNA with a thermostable DNA polymerase. Science 1988; 239:487–91.
14. Yee C, Krishnan-Hewlett I, Baker C C, Schlegel R, Howley P M. Presence and Expression of Human Papillomavirus sequences in human cervical carcinoma cell lines. Am J Pathol 1985; 119:361–6.
15. Reddy E P, Reynolds R K, Santo E, Barbacid M. A point mutation is responsible for the acquisition of the transforming properties by the T24 humanbladder carcinoma oncogene. Nature 1982; 300:149–52.
16. Marmur, J. (1961) J. Mol. Biol 3, 208.

What is claimed is:

1. A nanotube comprising carbon to which is attached an assay-performance substance, said assay-performance also being linked to a label compound capable of being induced to luminesce.

2. A nanotube according to claim 1, wherein said nanotube is graphitic and said luminescence is electrochemiluminescence.

3. A composition for the detection of an analyte of interest present in a sample, which composition comprises:
   (i) a graphitic nanotube containing a functional group and
   (ii) an assay-performance-substance linked to said functional group, said assay-performance-substance being capable of binding to the analyte-of-interest.

4. A composition for the detection of an analyte of interest present in a sample, which composition comprises:
   (i) a graphitic nanotube containing a functional group and
   (ii) an assay-performance-substance linked to said functional group, said assay-performance-substance being bound to the analyte of interest.

5. A composition according to claim 4, further comprising a second assay-performance-substance bound to the analyte, said second assay-performance-substance being linked to a label compound capable of being induced to luminesce.

6. A composition for the detection of an analyte of interest present in a sample, which composition comprises
   (a) a graphitic nanotube containing a functional group and
   (b) an assay-performance-substance linked to said functional group wherein said assay-performance-substance contains at least one substance selected from the group consisting of
      (i) added analyte of interest or added analogue of said analyte;
      (ii) a binding partner of said analyte or a binding partner of an analogue of said analyte; and
      (iii) a reactive component capable of binding with (i) or (ii).

7. A composition according to claim 5, wherein said assay-performance-substance contains at least one substance selected from the group consisting of
   (i) added analyte of interest or added analogue of said analyte;
   (ii) a binding partner of said analyte or a binding partner of said analogue; and
   (iii) a reactive component capable of binding with (i) or (ii).

8. A method for performing a binding assay for an analyte of interest present in a sample comprising the steps of:
   (a) forming a composition containing
      (i) said sample
      (ii) a first assay-performance-substance linked to a label compound capable of being induced to luminesce, and
      (iii) a plurality of functionalized graphitic nanotubes bound to a second assay-performance-substance;
   (b) incubating said composition to form a complex which includes said graphitic nanotube bound to said second assay-performance-substance and said label compound bound to said first assay-performance-substance;
   (c) collecting said complex in a measurement zone;
   (d) inducing the label compound in said complex to luminesce, and
   (e) measuring the emitted luminescence to measure the presence of the analyte of interest in the sample.

9. A method as recited in claim 8 wherein said complex is collected on the surface of means for inducing luminescence and measuring said luminescence.

10. A method as recited in claim 9 based upon measurement of electrochemiluminescence wherein said complex is collected at an electrode surface.

11. A method for performing a binding assay for an analyte of interest present in a sample based upon measurement of electrochemiluminescence at an electrode surface comprising the steps:
    (a) forming a composition containing
       (i) said sample
       (ii) a first assay-performance-substance linked to a label compound capable of being induced to electrochemiluminesce, and (iii) a plurality of functionalized graphitic nanotubes bound to a second assay-performance-substance;

(b) incubating said composition to form a complex which includes said graphitic nanotube bound to said second assay-performance-substance and said label compound bound to said first assay-performance-substance;

(c) collecting said complex;

(d) causing said collected complex to come in contact with an electrode surface and inducing the label compound in said complex to luminesce by impressing a voltage on said electrode; and (e) measuring the emitted luminescence at the electrode surface to measure the presence of the analyte of interest in the sample.

12. A method for performing a binding assay for an analyte of interest present in a sample based upon measurement of electrochemiluminescence at an electrode surface comprising the steps:

(a) forming a composition containing
   (i) said sample
   (ii) A first assay-performance-substance linked to a label compound capable of being induced to electrochemiluminesce, and
   (iii) a plurality of magnetically responsive suspended graphitic nanotubes bound to a second assay-performance-substance;

(b) incubating said composition to form a complex which includes a graphitic nanotube and said label compound;

(c) collecting said complex by imposition of a magnetic field on said graphitic nanotubes;

(d) causing said collected complex to come in contact with an electrode surface and inducing the label compound in said complex to luminescence by imposing a voltage on said electrode; and (e) measuring the emitted luminescence at the electrode surface to measure the presence of the analyte of interest in the sample.

13. A method as recited in claim 12 wherein the imposition of said magnetic field causes said complex to collect at the surface of said electrode.

14. A composition of matter for use as a reagent in a microparticulate-based binding assay comprising functionalized graphitic nanotubes bound to an assay-performance-substance and at least one other component selected from the group consisting of:

(a) electrolyte;

(b) label compound containing an ECL moiety;

(c) analyte of interest or an analog of the analyte of interest;

(d) a binding partner of the analyte of interest or of its analog;

(e) a reactive component capable of reacting with (c) or (d);

(f) a reductant; and (g) an electrochemiluminescent-reaction enhancer;

provided, however, that no two components contained within any reagent composition are reactive with one another during storage so as to impair their function in the intended assay.

15. A reagent as recited in claim 14 containing magnetically responsive graphitic nanotubes.

16. An assay reagent for an assay based upon a binding reaction and the measurement of an electrochemiluminescent phenomenon comprising:

(a) an electrolyte;

(b) a plurality of magnetically responsive functionalized graphitic nanotubes bound to a first assay-performance-substance; and (c) a second assay-performance-substance bound to a chemical moiety having electrochemiluminescent properties.

17. A method for performing an assay for an analyte of interest present in a sample, which analyte is an enzyme, comprising the steps of:

(a) forming a composition containing
   (i) said sample, and
   (ii) a functionalized graphitic nanotube bound to a component which is bound to a label compound capable of being induced to luminesce, wherein said component is a substrate of the analyte of interest;

(b) incubating said composition under conditions to permit said analyte to cleave said component, whereby a label sub-component free from said nanotube results from said cleavage;

(c) separating said graphitic nanotube from said composition;

(d) inducing the free label sub-component to luminesce; and (e) measuring the emitted luminescence to measure the presence of the analyte of interest in the sample.

18. A graphitic nanotube linked to at least two components selected from the group consisting of (i) an electrochemiluminescent label, (ii) an enzyme and (iii) an enzyme cofactor.

19. A graphitic nanotube linked to an enzyme biosensor, wherein said enzyme biosensor includes a label compound capable of being induced to electrochemiluminesce.

* * * * *